US010435740B2

(12) United States Patent
Kladde et al.

(10) Patent No.: US 10,435,740 B2
(45) Date of Patent: Oct. 8, 2019

(54) DETERMINATION OF METHYLATION STATE AND CHROMATIN STRUCTURE OF TARGET GENETIC LOCI

(71) Applicant: UNIVERSITY OF FLORIDA RESEARCH FOUNDATION, INC., Gainesville, FL (US)

(72) Inventors: Michael P. Kladde, Newberry, FL (US); Nancy H. Nabilsi, Gainesville, FL (US); Carolina E. Pardo, Pacifica, CA (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 796 days.

(21) Appl. No.: 14/773,826

(22) PCT Filed: Apr. 1, 2014

(86) PCT No.: PCT/US2014/032591
§ 371 (c)(1),
(2) Date: Sep. 9, 2015

(87) PCT Pub. No.: WO2014/165549
PCT Pub. Date: Oct. 9, 2014

(65) Prior Publication Data
US 2016/0115530 A1    Apr. 28, 2016

Related U.S. Application Data

(60) Provisional application No. 61/807,223, filed on Apr. 1, 2013.

(51) Int. Cl.
C12Q 1/6858    (2018.01)
C12Q 1/48      (2006.01)
C12Q 1/6886    (2018.01)

(52) U.S. Cl.
CPC .......... C12Q 1/6858 (2013.01); C12Q 1/48 (2013.01); C12Q 1/6886 (2013.01); C12Q 2600/154 (2013.01)

(58) Field of Classification Search
None
See application file for complete search history.

(56) References Cited

U.S. PATENT DOCUMENTS

2010/0129874 A1* 5/2010 Mitra .................. C12P 19/34
                                                     435/91.2
2012/0289414 A1   11/2012 Mitra et al.

FOREIGN PATENT DOCUMENTS

WO    WO-2003/004702    1/2003
WO    WO-2008/096146    8/2008
WO    WO-2009/024019    2/2009

OTHER PUBLICATIONS

Quail et al. Nature Methods 2008; 5: 1005-1010 (Year: 2008).*
(Continued)

Primary Examiner — Angela M. Bertagna
(74) Attorney, Agent, or Firm — Timothy H. Van Dyke; Beusse, Wolter, Sanks & Maire PLLC

(57) ABSTRACT

The subject invention pertains to a method of determining methylation state and chromatin structure of target loci. The method comprises treating the genetic material obtained from the cells with DNA methyltransferase, capturing target genetic loci using a set of oligonucleotides, ligating the target loci with oligonucleotide patches that flank the target loci, treating the target loci flanked by oligonucleotide patches with bisulfite, optionally amplifying the target loci by polymerase chain reaction, sequencing the PCR products, and analyzing the sequences to determine methylation state and chromatin structure of the target loci. The current invention also provides a method to identify genes associated with a disease. The invention also provides a method to (Continued)

detect cells suffering from a disease in a group of cells. The current invention also provides kits suitable for carrying out the method of determining methylation state and chromatin structure of the target loci.

16 Claims, 25 Drawing Sheets

(56) References Cited

OTHER PUBLICATIONS

Dedkov, V.S. Molecular Genetics, Microbiology and Virology 2012; 27: 40-47 (Year: 2012).*
Knapp et al. Methods in Molecular Biology 2012; 840: 155-170 (Year: 2012).*
Zhang, Y. and Jeltsch, A. Genes 2010; 1:85-101 (Year: 2010).*
Deng et al. Cancer Research 2004; 64: 2692-2698 (Year: 2004).*
Darst, R.P., et al., "DNA Methyltransferase Accessibility Protocol for Individual Templates by Deep Sequencing," *Methods in Enzymology*, 2012, vol. 513, pp. 185-204.
Nabilsi, N.H., et al., "Multiplex mapping of chromatin accessibility and DNA methylation within targeted single molecules identifies epigenetic heterogeneity in neural stem cells and glioblastoma," *Genome Research*, 2013, vol. 24, No. 2, pp. 329-339.
Amstutz, U., et al., "Dihydropyrimidine dehydrogenase gene as a major predictor of severe 5-fluorouracil toxicity," *Pharmacogenomics*, Sep. 2011, vol. 12, No. 9, pp. 1321-1336.
Chan, S.H., et al., "Cloning of CviPII nicking and modification system from chlorella virus NYs-1 and application of Nt.CviPII in random DNA amplification," *Nucleic Acids Research*, 2004, vol. 32, No. 21, pp. 6187-6199.
Dallosso, A.R., et al., "Frequent Long-Range Epigenetic Silencing of Protocadherin Gene Clusters on Chromosome 5q31 in Wilms' Tumor," *PLOS Genetics*, Nov. 26, 2009, vol. 5, No. 11, Doc No. e1000745.
Deleyrolle, L.P., et al., "Evidence for label-retaining tumour-initiating cells in human glioblastoma," *Brain*, 2011, vol. 134, No. 5, pp. 1331-1343.
Deleyrolle, L.P., et al., "Isolation, Expansion, and Differentiation of Adult Mammalian Neural Stem and Progenitor Cells Using the Neurosphere Assay," *Methods in Molecular Biology*, 2009, vol. 549, pp. 91-101.
Delmas, A.L., et al., "WIF1 is a frequent target for epigenetic silencing in squamous cell carcinoma of the cervix," *Carcinogenesis*, 2011, vol. 32, No. 11, pp. 1625-1633.
Dieterich, L.C., et al., "Transcriptional profiling of human glioblastoma vessels indicates a key role of VEGF-A and TGFβ2 in vascular abnormalization," *Journal of Pathology*, 2012, vol. 228, No. 3, pp. 378-390.
Elliott, A.M., et al., "ABCB8 Mediates Doxorubicin Resistance in Melanoma Cells by Protecting the Mitochondrial Genome," *Molecular Cancer Research*, Jan. 2009, vol. 7, No. 1, pp. 79-87.
Esteller, M., "Cancer epigenomics: DNA methylomes and histone-modification maps," *Nature Reviews Genetics*, Apr. 2007, vol. 8, No. 4, pp. 286-298.
Fang, G., et al., "Genome-wide mapping of methylated adenine residues in pathogenic *Escherichia coli* using single-molecule real-time sequencing," *Nature Biotechnology*, Dec. 2012, vol. 30, No. 12, pp. 1232-1239.
Felsberg, J., et al., "Promoter methylation and expression of MGMT and the DNA mismatch repair genes MLH1, MSH2, MSH6and PMS2 in paired primary and recurrent glioblastomas," *International Journal of Cancer*, 2011, vol. 129, No. 3, pp. 659-670.
Fuks, F., "DNA methylation and histone modifications: teaming up to silence genes," *Current Opinion in Genetics & Development*, 2005, vol. 15, No. 5, pp. 490-495.

Gal-Yam, E.N., et al., "Constitutive Nucleosome Depletion and Ordered Factor Assembly at the GRP78 Promoter Revealed by Single Molecule Footprinting," *PLOS Genetics*, Sep. 2006, vol. 2, No. 9, Doc No. e160.
Hansen, K.D., et al., "Increased methylation variation in epigenetic domains across cancer types," *Nature Genetics*, Aug. 2011, vol. 43, 8, pp. 768-775.
Herman, J.G., et al., "Gene Silencing in Cancer in Association with Promoter Hypermethylation," *New England Journal of Medicine*, Nov. 20, 2003, vol. 349, No. 21, pp. 2042-2054.
Jiang, C., et al., "Nucleosome positioning and gene regulation: advances through genomics," *Nature Reviews Genetics*, Mar. 2009, vol. 10, No. 3, pp. 161-172.
Katori, S., et al., "Protocadherin-α Family Is Required for Serotonergic Projections to Appropriately Innervate Target Brain Areas," *Journal of Neuroscience*, Jul. 22, 2009, vol. 29, No. 29, pp. 9137-9147.
Kelly, T.K., et al., "Genome-wide mapping of nucleosome positioning and DNA methylation within individual DNA molecules," *Genome Research*, 2012, vol. 22, No. 12, pp. 2497-2506.
Kilgore, J.A., etal., "Single-molecule and population probing of chromatin structure using DNA methyltransferases," *Methods*, 2007, vol. 41, No. 3, pp. 320-332.
Knobbe, C.B., et al., "Genetic alteration and expression of the phosphoinositol-3-kinase/Akt pathway genes PIK3CA and PIKE in human glioblastomas," *Neuropathology and Applied Neurobiology*, 2005, vol. 31, No. 5, pp. 486-490.
Lai, A.Y., etal., "DNA methylation prevents CTCF-mediated silencing of the oncogene BCL6 in B cell lymphomas," *Journal of Experimental Medicine*, Aug. 23, 2010, vol. 207, No. 9, pp. 1939-1950.
Li, Y., et al., "MicroRNA-21 targets LRRFIP1 and contributes to VM-26 resistance in glioblastoma multiforme," *Brain Research*, 2009, vol. 1286, pp. 13-18.
Maekawa, R., et al., "Disease-dependent Differently Methylated Regions (D-DMRS) of DNA are Enriched on the X Chromosome in Uterine Leiomyoma," *Journal of Reproduction and Development*, 2011, vol. 57, No. 5, pp. 604-612.
Martinez, R. et al., "Low-level microsatellite instability phenotype in sporadic glioblastoma multiforme," *Journal of Cancer Research and Clinical Oncology*, 2005, vol. 131, No. 2, pp. 87-93.
Maruya, S.I., et al., "ICAM-5 (telencephalin) gene expression in head and neck squamous carcinoma tumorigenesis and perineural invasion!," *Oral Oncology*, 2005, vol. 41, No. 6, pp. 580-588.
Mashima, T., et al., "Promotion of glioma cell survival by acyl-CoA synthetase 5 under extracellular acidosis conditions," *Oncogene*, 2009, vol. 28, No. 1, pp. 9-19.
Mokarram, P., et al., "Distinct High-Profile Methylated Genes in Colorectal Cancer," *PLOS ONE*, Sep. 2009, vol. 4, No. 9, Doc. No. e7012.
Nabilsi, N.H., et al., "DNA methylation inhibits p53-mediated survivin repression," *Oncogene*, 2009, vol. 28, No. 19, pp. 2046-2050.
Pardo, C., et al., "DNA Methyltransferase Probing of Chromatin Structure Within Populations and on Single Molecules," *Methods in Molecular Biology*, 2009, vol. 523, pp. 41-65.
Pardo, C.E., et al., "MethylViewer: computational analysis and editing for bisulfite sequencing and DNA methyltransferase accessibility protocol for individual templates (MAPit) projects," *Nucleic Acids Research*, 2011, vol. 39, No. 1, Doc. No. e5.
Pardo, C.E., et al., "Simultaneous Single-Molecule Mapping of Protein-DNA Interactions and DNA Methylation by MAPit," *Current Protocols in Molecular Biology*, 2011, Chapter 21, Unit 21 22.
Piao, J.H., "Cellular Composition of Long-Term Human Spinal Cord- and Forebrain-Derived Neurosphere Cultures," *Journal of Neuroscience Research*, 2006, vol. 84, No. 3, pp. 471-482.
Pujadas, E., et al., "Regulated Noise in the Epigenetic Landscape of Development and Disease," *Cell*, Mar. 16, 2012, vol. 148, No. 6, pp. 1123-1131.
Renaud, S., et al., "Dual role of DNA methylation inside and outside of CTCF-binding regions in the transcriptional regulation of the telomerase hTERT gene," *Nucleic Acids Research*, 2007, vol. 35, No. 4, pp. 1245-1256.

(56) References Cited

OTHER PUBLICATIONS

Santosh, V., et al., "Grade-Specific Expression of Insulin-like Growth Factor-Binding Proteins-2,-3, and—5 in Astrocytomas: IGFBP-3 emerges as a Strong Predictor of Survival in Patients with Newly Diagnosed Glioblastoma," *Cancer Epidemiology, Biomarkers & Prevention*, 2010, vol. 19, No. 6, pp. 1399-1408.

Schreiber, S.L., et al., "Signaling Network Model of Chromatin," *Cell*, Dec. 13, 2002, vol. 111, No. 6, pp. 771-778.

Sharma, S.V., et al., "A Chromatin-Mediated Reversible Drug-Tolerant State in Cancer Cell Subpopulations," *Cell*, Apr. 2, 2010, vol. 141, No. 1, pp. 69-80.

Shen, L., et al., "Induction of p53-Dependent, Insulin-Like Growth Factor-Binding Protein-3-Mediated Apoptosis in Glioblastoma Multiforme Cells by a Protein Kinase Cα Antisense Oligonucleotide," *Molecular Pharmacology*, 1999, vol. 55, No. 2, pp. 396-402.

Shen, L., et al., "Induction of Apoptosis in Glioblastoma Cells by Inhibition of Protein Kinase C and Its Association with the Rapid Accumulation of p53 and Induction of the Insulin-like Growth Factor-1-Binding Protein-3," *Biochemical Pharmacology*, 1998, vol. 55, No. 10, pp. 1711-1719.

Shmelkov, S.V., et al., "Alternative promoters regulate transcription of the gene that encodes stem cell surface protein AC133," *Blood*, Mar. 15, 2004, vol. 103, No. 6, pp. 2055-2061.

Siebzehnrubl, F.A., et al., "Isolation and Characterization of Adult Neural Stem Cells," *Methods in Molecular Biology*, 2011, vol. 750, pp. 61-77.

Song, C.X., et al., "Mapping recently identified nucleotide variants in the genome and transcriptome," *Nature Biotechnology*, Nov. 2012, vol. 30, No. 11, pp. 1107-1116.

Sumiyoshi, H., et al., "Ubiquitous Expression of the α1 (XIX) Collagen Gene (Col19a1) during Mouse Embryogenesis Becomes Restricted to a Few Tissues in the Adult Organism," *Journal of Biological Chemistry*, Jul. 4, 1997, vol. 272, No. 27, pp. 17104-17111.

Sun, Y., et al., "CD133 (Prominin) Negative Human Neural Stem Cells Are Clonogenic and Tripotent," *PLoS ONE*, May 2009, vol. 4, No. 5, Doc. No. e5498.

Suriano, A.R., et al., "GCF2/LRRFIP1 Represses Tumor Necrosis Factor Alpha Expression," *Molecular and Cellular Biology*, Oct. 2005, vol. 25, No. 20, pp. 9073-9081.

Swinton, D., et al., "Purification and characterization of the unusual deoxynucleoside, α-N-(9-β-D-2'-deoxyribofuranosylpurin-6-yl)glycinamide, specified by the phage Mu modification function," *Proceedings of the National Academy of Sciences of the USA*, Dec. 1983, vol. 80, No. 24, pp. 7400-7404.

Tavassoli, P., et al., "TAF1 Differentially Enhances Androgen Receptor Transcriptional Activity via Its N-Terminal Kinase and Ubiquitin-Activating and—Conjugating Domains," *Molecular Endocrinology*, Apr. 2010, vol. 24, No. 4, pp. 696-708.

Varley, K.E., et al., "Bisulfite Patch PCR enables multiplexed sequencing of promoter methylation across cancer samples," *Genome Research*, 2010, vol. 20, No. 9, pp. 1279-1287.

Wolff, E.M., et al., "Hypomethylation of a LINE-1 Promoter Activates an Alternate Transcript of the MET Oncogene in Bladders with Cancer," *PLoS Genetics*, Apr. 2010, vol. 6, No. 4, Doc. No. e1000917.

Xu, M., et al., "Cloning, characterization and expression of the gene coding for a cytosine-5-DNA methyltransferase recognizing GpC," *Nucleic Acids Research*, 1998, vol. 26, No. 17, pp. 3961-3966.

Yang, X., et al., "Gene Reactivation by 5-Aza-2'-Deoxycytidine-Induced Demethylation Requires SRCAP-Mediated H2A.Z Insertion to Establish Nucleosome Depleted Regions," *PLoS Genetics*, Mar. 2012, vol. 8, No. 3, Doc. No. e1002604.

You, J.S., et al., "OCT4 establishes and maintains nucleosome-depleted regions that provide additional layers of epigenetic regulation of its target genes," *Proceedings of the National Academy of Sciences of the USA*, Aug. 30, 2011, vol. 108, No. 35, pp. 14497-14502.

Yu, J., et al., "The EPHB6 Receptor Tyrosine Kinase Is a Metastasis Suppressor That Is Frequently Silenced by Promoter DNA Hypermethylation In Non-Small Cell Lung Cancer," *Clinical Cancer Research*, 2010, vol. 16, No. 8, pp. 2275-2283.

Stark, A.M., et al., "The expression of mismatch repair proteins $MLH_1$, $MSH_2$ and MSH6 correlates with the $Ki6_7$ proliferation index and survival in patients with recurrent glioblastoma," *Neurological Research*, 2010, vol. 32, No. 8, pp. 816-820.

Renbaum, P., et al., "Cloning, characterization, and expression in *Escherichia coli* of the gene coding for the CpG DNA methylase from *Spiroplasma* sp. Strain MQ1(M-SssI)," *Nucleic Acids Research*, 1990, vol. 18, No. 4, pp. 1145-1152.

Szybka, M., et al., "Microsatellite instability and expression of DNA mismatch repair genes in malignant astrocytic tumors from adult and pediatric patients," *Clinical Neuropathology*, 2003 vol. 22, No. 4/2003, pp. 180-186.

\* cited by examiner

DETERMINATION OF METHYLATION STATE AND CHROMATIN STRUCTURE OF TARGET GENETIC LOCI

The invention was made with government support under R01CA155390 awarded by the National Institutes of Health. The government has certain rights in the invention.

CROSS-REFERENCE TO RELATED APPLICATIONS

This application is the U.S. national stage application of International Patent Application No. PCT/US2014/032591, filed Apr. 1, 2014, which claims the benefit of U.S. Provisional Application Ser. No. 61/807,223, filed Apr. 1, 2013, the disclosures of which are hereby incorporated by reference in their entirety, including all figures, tables and amino acid or nucleic acid sequences.

BACKGROUND OF THE INVENTION

Human tumors often display substantial intratumoral heterogeneity in both phenotypic and molecular features. This cellular heterogeneity represents a formidable challenge to the discovery of effective and lasting cancer treatments. The frequency and degree of tumor heterogeneity cannot be explained solely by genetic determinants. Additionally, the reversible nature of cancer cell proliferative potential and drug tolerance suggests mechanisms that invoke plasticity, characteristic of epigenetic regulation.

Dynamic control of gene expression is exerted by the interplay between various epigenetic mechanisms, including DNA methylation, histone tail post-translational modifications, and nucleosome positioning and occupancy (Schreiber and Bernstein 2002; Fuks 2005; Esteller 2007). Dysregulation of any of these regulatory layers can alter gene expression and, moreover, such epigenetic perturbations have been established as major determinants of cancer initiation and progression. Epigenetic variability has been strongly implicated in mediating tumor heterogeneity across diverse diseases. However, the extent to which epigenetic differences between individual cells underlie intratumoral heterogeneity remains relatively unexplored.

Aberrant DNA methylation of CpG (or CG) dinucleotides is a well-documented phenomenon in virtually all tumor types studied to date. It is widely accepted that DNA methylation near transcriptional start sites (TSSs) is associated with gene silencing. Hypermethylation of promoters of tumor-suppressive genes and hypomethylation of tumor-promoting genes is commonly observed, even in early stages of carcinogenesis (Herman and Baylin 2003). Though it is often evaluated in isolation, DNA methylation exerts control over gene expression within the context of chromatin. Expressed and poised genes are usually unmethylated and depleted of nucleosomes near their TSSs, thereby exhibiting increased accessibility to trans-activating factors (reviewed in Jiang and Pugh 2009). Conversely, the TSSs of inactive genes tend to be associated with high nucleosome occupancy, conferring chromatin inaccessibility, but can be either unmethylated or methylated. Thus, integrated evaluation of DNA methylation within the context of chromatin accessibility is likely to be more informative than evaluating each epigenetic feature separately. Notably, the extent of cell-to-cell heterogeneity in chromatin accessibility at gene promoters in either disease-free or tumor cells remains ill defined.

Assessing intratumoral epigenetic heterogeneity necessitates the use of methods able to query chromatin structure at the level of single molecules, thereby avoiding population averaging. A high-resolution DNA footprinting technique, termed MAPit (DNA methyltransferase accessibility protocol for individual templates) was previously developed which exploits exogenous addition of DNA methyltransferases (DNMTs), such as the GC DNA methyltransferase (M.CviPI) to probe accessibility of GC sites in chromatin (Xu et al. 1998; Pardo et al. 2009). Following bisulfite conversion of isolated genomic DNA and sequencing of clonally amplified molecules, that is, bisulfite genomic sequencing (BGS), the positions of nucleosomes and DNA-bound non-histone proteins are inferred based on footprints or spans of protection against methylation by M.CviPI. Furthermore, because M.CviPI modifies GC, endogenous CG methylation is concurrently mapped, allowing for direct correlation of two distinct epigenetic features along a single strand of DNA (molecule). This technique has been used to simultaneously map DNA methylation and nucleosome positions in many gene-specific studies (Kilgore et al. 2007; Wolff et al. 2010; Delmas et al. 2011; You et al. 2011; Yang et al. 2012), and more recently, genome wide (Kelly et al. 2012).

Cells that are drug-tolerant or have tumor-initiating capabilities are of high biological interest and are estimated to represent 1-5% of bulk tumor cells. Study of this or other minority subpopulations by genome-wide BGS is currently precluded due to requirements for large amounts of input DNA and prohibitive costs associated with obtaining the needed depth in sequencing coverage. The latter problem is compounded as the number of samples to be analyzed increases. A further limitation of present genome-wide BGS approaches is the short sequencing reads typically employed. Short-read sequences destroy the structural integrity or phasing of epigenetic information present on a continuous DNA strand, which is essential for determining if epigenetic features map to the same or different molecules. Maintaining the continuity of epigenetic information is of increased importance in complex samples with abundant inherent diversity.

To circumvent these limitations, the current invention provides a method of simultaneously determining chromatin structure and DNA methylation state of one or more (or a plurality of) genetic loci using deep sequencing techniques that provided for high sequencing coverage and long reads of genetic material.

BRIEF SUMMARY OF THE INVENTION

Current invention provides a method for determining chromatin structure and methylation state at high resolution on target genetic loci of interest. The current invention provides a method for determining whether the target loci are 1) unmethylated and inaccessible; 2) unmethylated and accessible; 3) methylated and inaccessible; or 4) methylated and accessible, wherein the sites within nucleosomes or those occluded by DNA-bound non-histone proteins are inaccessible and sites outside nucleosomes or those free of non-histone proteins are accessible. The method of the current invention is called MAPit-patch. MAPit-patch can be used to analyze chromatin structure and methylation state of target loci, for example, promoters of genes encoding cancer-associated functions. MAPit-patch is highly scalable and enables multiplexed processing of samples with limiting input quantities of starting genomic DNA. MAPit-patch also provides long-read sequences of targeted regions, maintains continuity of epigenetic information along contiguous DNA strands, and provides substantial depth of coverage. Thus, MAPit-patch identifies subpopulations of epigenetic configurations previously obscured by existing genome-wide and population-ensemble methodologies.

MAPit-patch can be used to compare chromatin structures and methylation states of target loci between different cells. For example, MAPit-patch can be used to compare chromatin structure and methylation state of promoters associated the genes that are expressed differently between neural stem cell (NSC) and glioblastoma (GBM) cells.

In an embodiment of the invention endogenous methylation state and chromatin structure of target loci is identified by analyzing the genetic material with or without treatment with exogenous DNA methyltransferase. Comparison of the sequence of genetic material obtained with or without exogenous DNA methyltransferase after bisulfite treatment can be used to elucidate endogenous methylation state and chromatin structure of target loci.

Another embodiment of the invention provides a method of identifying cells suffering from a disease in a group of cells by determining methylation state and chromatin structure of promoters of the genes known to be associated with the disease. For example, the method of the current invention can be used to detect a presence of a cancerous cell in a tissue sample.

The current invention also provides a kit for carrying out MAPit-patch method. The kit for the MAPit-patch method comprises of a set of oligonucleotides designed to determine chromatin structure and methylation state of target loci. The set of oligonucleotides in the MAPit-patch kit can be customized based on user requirements. The kit can further comprise reagents for isolating genetic material from cells, DNA methyltransferase, reagents for purifying genetic material treated with DNA methyltransferase enzyme, one or more DNA restriction endonucleases, one or more exonucleases, ligase, bisulfite, reagents for PCR amplifying the target loci of interest, and/or reagents for sequencing the amplified target loci of interest using a variety of DNA sequencing platforms.

Figure 1:
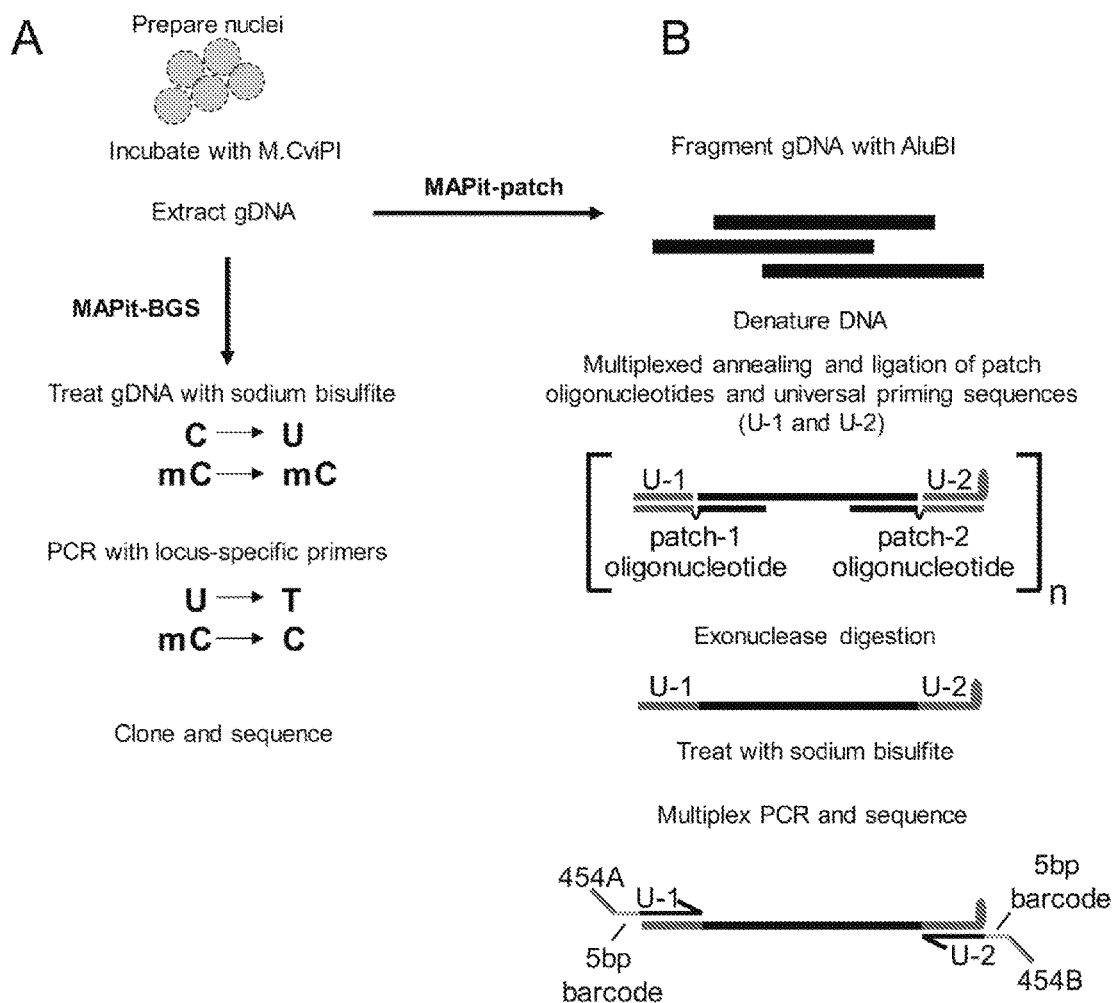
FIGS. 1A-1B. MAPit and MAPit-patch workflow.

Both MAPit and MAPit-patch begin with preparation of nuclei and incubation with M.CviPI under conditions that maintain chromatin integrity. Upon termination of the reaction, genomic DNA (gDNA) is extracted and then processed either by BGS or MAPit-patch workflow. (A) For MAPit-BGS, genomic DNA is bisulfite treated such that unmethylated "C" is converted to "U" while methylated "C" (mC) is protected from deamination and remains methylated "C." Bisulfite-treated DNA is then amplified using locus-specific primers and reaction products are purified and cloned. Individual clones are subsequently sequenced and data are aligned and analyzed to map the methylation status of CG and GC sites. (B) For MAPit-patch, gDNA is fragmented using restriction enzyme AluBI (or other suitable enzyme or enzymes) insensitive to methylation of both CG and GC sites. Fragmented DNA is then subjected to target selection whereby patch-1 and patch-2 oligonucleotides hybridize and thus "patch" universal priming sequences to both ends of one DNA strand of each targeted locus. Complementary, universal priming sequences (U-1 and U-2) hybridize to their respective patch oligonucleotide and are ligated to each targeted locus. Note that the U-2 primer contains phosphorothioates and a 3-carbon spacer at its 3' end. These modifications serve to protect the targeted DNA molecule from subsequent exonuclease digestion that removes any unhybridized oligonucleotides and all non-targeted gDNA. Selected DNA is then bisulfite converted and amplified using universal primers (complementary to U-2 and same sequence as U-1) appended with sequencing-platform-specific adapter sequences (for example, 454-adapters). These primers also typically contain 5-bp "barcodes" to facilitate multiplexing samples in a single sequencing reaction. Amplified products are then purified and sequenced.

FIGS. 2A-2G. MAPit identifies expected epigenetic patterns and detects chromatin heterogeneity. (A) Schematic of the proximal MLH1 promoter (an expressed gene) with TSSs indicated with bent arrows and a gray ellipse scaled to the length of a nucleosome core particle is shown. (B) MethylMapper plots display MAPit-BGS data for MLH1 in NSCs probed with 0 U (top), 30 U (middle) or 100 U (bottom) of M.CviPI activity. Each row represents a sequenced molecule. Two or more consecutive methylated CG sites are connected by red while two or more consecutive unmethylated CG sites are connected by black (see key, FIG. 2E, left). Gray connects the borders between methylated and unmethylated CG sites. Similarly, two or more consecutive accessible GC sites are connected by yellow while two or more consecutive inaccessible GC sites are connected by black (see key, FIG. 2E, right). Gray connects the borders between accessible and inaccessible GC sites. CG methylation and GC accessibility are depicted on left and right panels, respectively. The same format is used to depict data at (C, D) the TMS1 promoter (a silent gene) and (F, G) the PROM1 promoter, a gene that is heterogeneously expressed in NSCs.

FIGS. 3A-3D. MAPit-patch does not alter bisulfite patch PCR performance and reproducibility. (A) The number of sequencing reads obtained is plotted as a function of amplicon length. Sequence coverage is decreased as amplicon length increases indicating length bias as previously reported. (B) Fraction of CG methylation from cells treated with 0 U M.CviPI is plotted against fraction of CG methylation from cells treated with 100 U M.CviPI. Linear regression and Pearson's correlation indicate that M.CviPI activity does not affect quantification of CG methylation. DNA methylation and chromatin accessibility at the imprinted locus H19 are shown for NSC treated with 0 U (C) and 100 U (D) M.CviPI.

Figure 4:
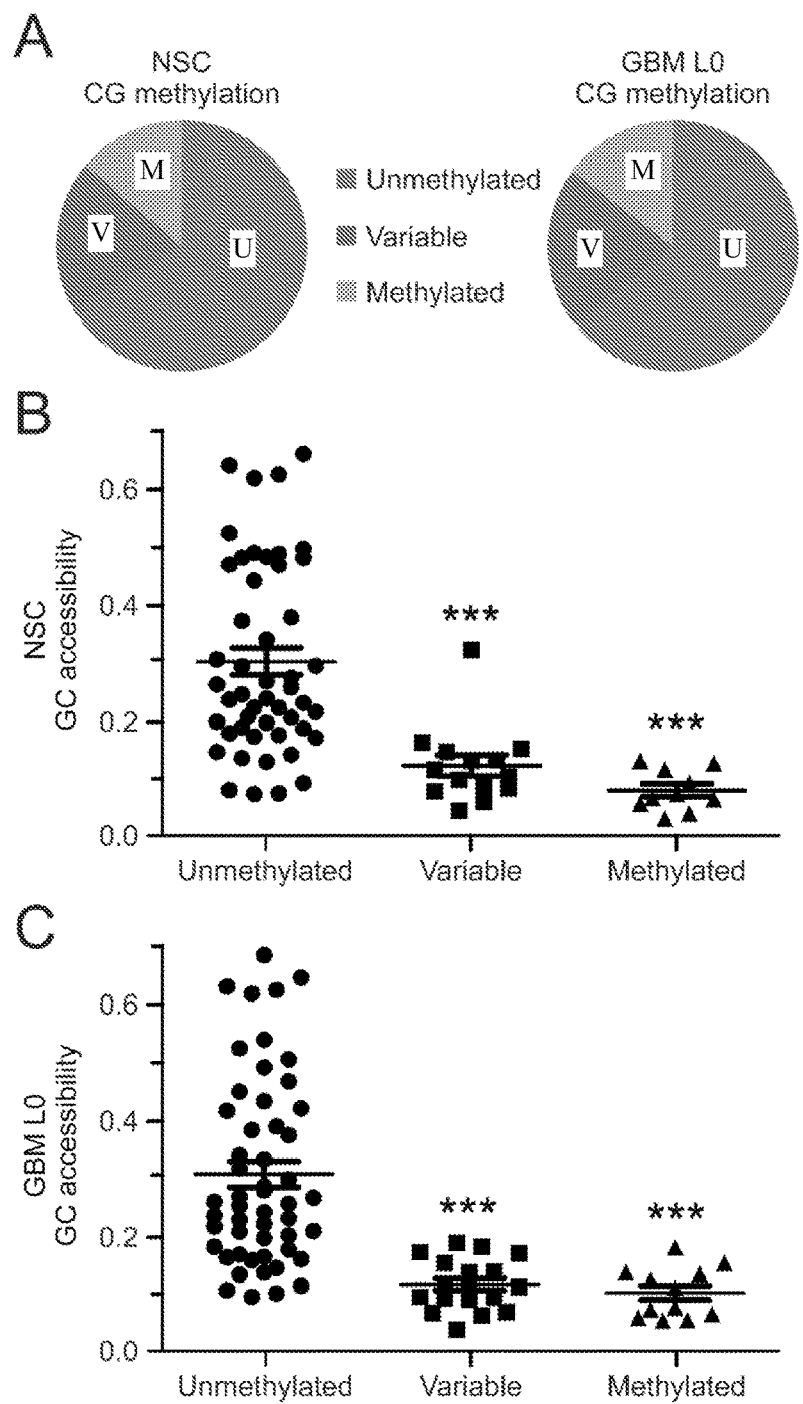

FIGS. 4A-4C. Promoter distribution of CG methylation is similar in NSC and GBM L0 and is inversely associated with GC accessibility. (A) The distribution of promoters that are unmethylated (U), variably methylated (V) or methylated (M) in NSC (left) and GBM (right) is shown. The fraction of GC accessibility within each promoter methylation class was quantified for NSC (B) and GBM (C). A dot plot with mean fraction GC accessibility±one standard deviation of the mean (SDM) is plotted. P<0.01, *P<0.001 compared to GC accessibility from unmethylated promoters for each sample.

FIGS. 5A-5C. Differential epigenetic features identify differentially expressed genes in NSC and GBM L0. Fraction CG methylation and GC accessibility was compared at each locus between NSC and GBM. Loci exhibiting statistically significant (Fisher's exact test P<0.01) differences in CG methylation (A) or GC accessibility (B) are shown. Note that the last 9 promoters plotted in (A) are also the first 9 promoters plotted in (B) and constitute dual differentially methylated and differentially accessible promoters. Gene expression values for a randomly selected subset of genes from (A) and (B) are shown in (C). Each bar represents the mean expression for each transcript relative to NSC±SDM (n=2). All data are normalized to 18S rRNA expression. Note that GBM L0 is the sample for which MAPit-patch data is obtained while GBM L2 is a second, independent sample.

FIGS. 6A-6E. Chromatin accessibility in NSC and GBM L0 is heterogeneous and inversely associated with CG methylation. (A) Representative promoters exhibiting the five different GC accessibility patterns. Scale bars in base pairs included at bottom are 147 bp in length unless indicated otherwise. (B) Distribution of all analyzed promoters into the five accessibility classes, accessible (A), mostly accessible (MA), half accessible (HA), mostly inaccessible (MI) and inaccessible (I), for NSC (left) and GBM L0 (right). (C) Quantitative confirmation of different classes of chromatin accessibility identified by MAPit-patch obtained by measuring protection of SacI sites in the indicated promoters from 0, 40, or 60 U SacI activity. Each bar represents the mean protection for each promoter relative to 0 U SacI±0.5 of the range (n=2), normalized to a control locus lacking a SacI site. Dot plots for NSC (D) and GBM L0 (E) of CG methylation in each GC accessibility class. Mean fractions of CG methylation±SEM are plotted. *$P<0.05$, $P<0.01$, and *$P<0.001$ relative to fraction CG methylation in inaccessible promoters for each sample.

FIGS. 7A-7F. A subset of variably methylated promoters exhibits distinct subpopulations of M.CviPI-accessible and M.CviPI-inaccessible molecules. MAPit-patch CG methylation data is shown for variably methylated promoters that exhibit distinct epigenetic populations (A, B), compared to others that show a more stochastic distribution of methylation (C, D). Note that a given molecule in each subpopulation tends to be mostly methylated or unmethylated as in A, B. By contrast, in C, D, every possible combination of methylation for the given number of CG sites is observed and distributed with similar frequencies across all molecules. Linked GC accessibility data is shown in (E, F), note that GC accessibility is largely restricted to the hypomethylated molecules in the promoter exhibiting subpopulations (E) but not in the promoter with more random CG methylation (F).

FIGS. 8A-8L. A subpopulation of molecules with relatively inaccessible chromatin at the MLH1 promoter is associated with Mlh1-negative GBM cells. (A) Schematic of 1.4 Kb of the MLH1 promoter. The three co-regulated TSSs in this region are shown with bent arrows. Half-arrows indicate the primer binding regions for MLH1 distal (black) and proximal (gray) MAPit-BGS amplicons. Asterisks indicate the boundaries of the MAPit-patch amplicons for the distal (black) and proximal (gray) MLH1 promoter. MAPit-patch GC accessibility data is shown for the distal (B) and proximal (C) MLH1 promoter. Both amplicons show a subpopulation of relatively inaccessible molecules (within cyan rectangles). (D) Schematic of the MAPit-BGS amplicon for the distal MLH1 promoter obtained using locus-specific primers (i.e., black half-arrows in A). An ellipse is shown scaled to the length of a nucleosome core particle (147 bp). GC accessibility at MLH1 is plotted for GBM L0 (E) and GBM L2 (F) and relatively inaccessible molecules are enclosed by a cyan rectangle. GC accessibility is also shown for the PMS2 promoter (G) in GBM L0 (H) and GBM L2 (I) cells. Note that PMS2 is highly accessible across all molecules (except 1 on GBM L2), with no discernible inaccessible subpopulation of significance. Immunostaining with an anti-Mlh1 antibody and flow cytometry showed the isotype background control (J; expected to approach 100%) as well as differing percentages of Mlh1-negative cells for GBM L0 (K; 13.6%) and GBM L2 (L; 28.5%).

Figure 9:
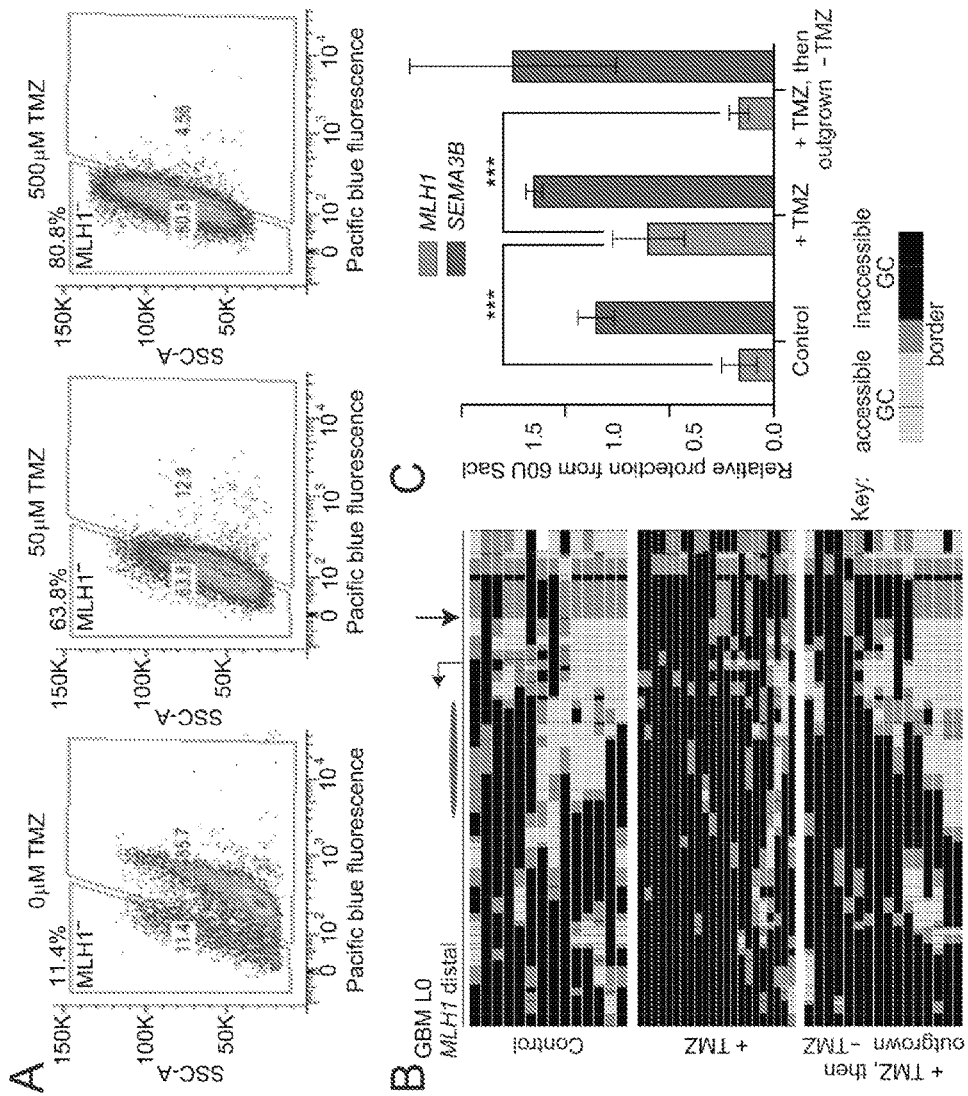

FIGS. 9A-9C. Cells with inaccessible chromatin at MLH1 are enriched upon treatment with temozolomide (TMZ). (A) Immunostaining with anti-Mlh1 antibody and flow cytometry were conducted on GBM cells treated with the indicated doses of TMZ after 72 hrs. (B) Chromatin accessibility at MLH1 was measured in control, TMZ-treated (+TMZ) and TMZ-treated cells expanded in drug-free media (+TMZ, then outgrown −TMZ) by MAPit-BGS and by protection from SacI activity (C). Note in (B), an arrow next to the TSS indicates the queried SacI site. Bars represent the mean protection from SacI activity for each locus±one standard error of the mean (SEM) (Control and TMZ, n=5, expanded n=3). Data is normalized to a control locus lacking a SacI site. ***$P<0.001$.

Figure 10:
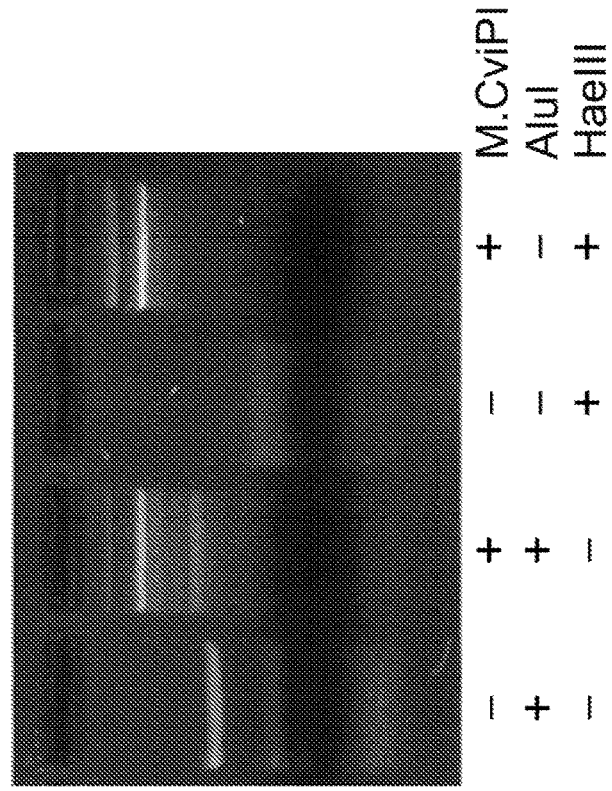
Figure 10:
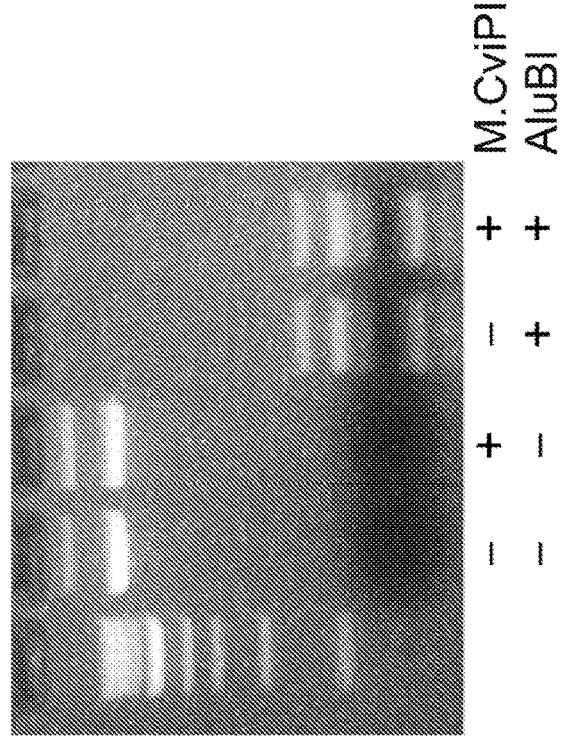

FIG. 10. AluBI is insensitive to GC methylation. Plasmid DNA was methylated in vitro with M.CviPI. Methylated and unmethylated DNA was digested with two GC methylation sensitive enzymes (AluI and HaeIII) and AluBI. Products were visualized by ethidium bromide staining and agarose electrophoresis. M, marker, 1 kb ladder.

FIGS. 11A-11D. Optimization of SacI chromatin accessibility assay. (A) Nuclei were prepared as described for MAPit then probed with multiple doses of SacI activity. Genomic DNA was extracted and amplified with QPCR primers flanking a SacI site in the indicated promoters. MLH1 is accessible while CDH5 is inaccessible in these cells. Bars represent mean protection from SacI activity±SDM of 3 technical replicates (n=1). Note that a residual population of molecules is not digested even at the highest dose of SacI activity at MLH1. To determine if the MLH1 molecules inaccessible to SacI digestion are the same as those inaccessible to MAPit probing, SacI digested nuclei were probed with M.CviPI and deaminated for BGS (B-D). The SacI site in the MLH1 promoter lies within the MAPit BGS amplicon as indicated in B. Thus, amplification of MLH1 is only possible across molecules that are not digested by SacI. Note that the SacI-inaccessible molecules are also largely inaccessible to M.CviPI in D. Thus inaccessibility to SacI and M.CviPI are observed in the same cellular subpopulation.

Figure 12:
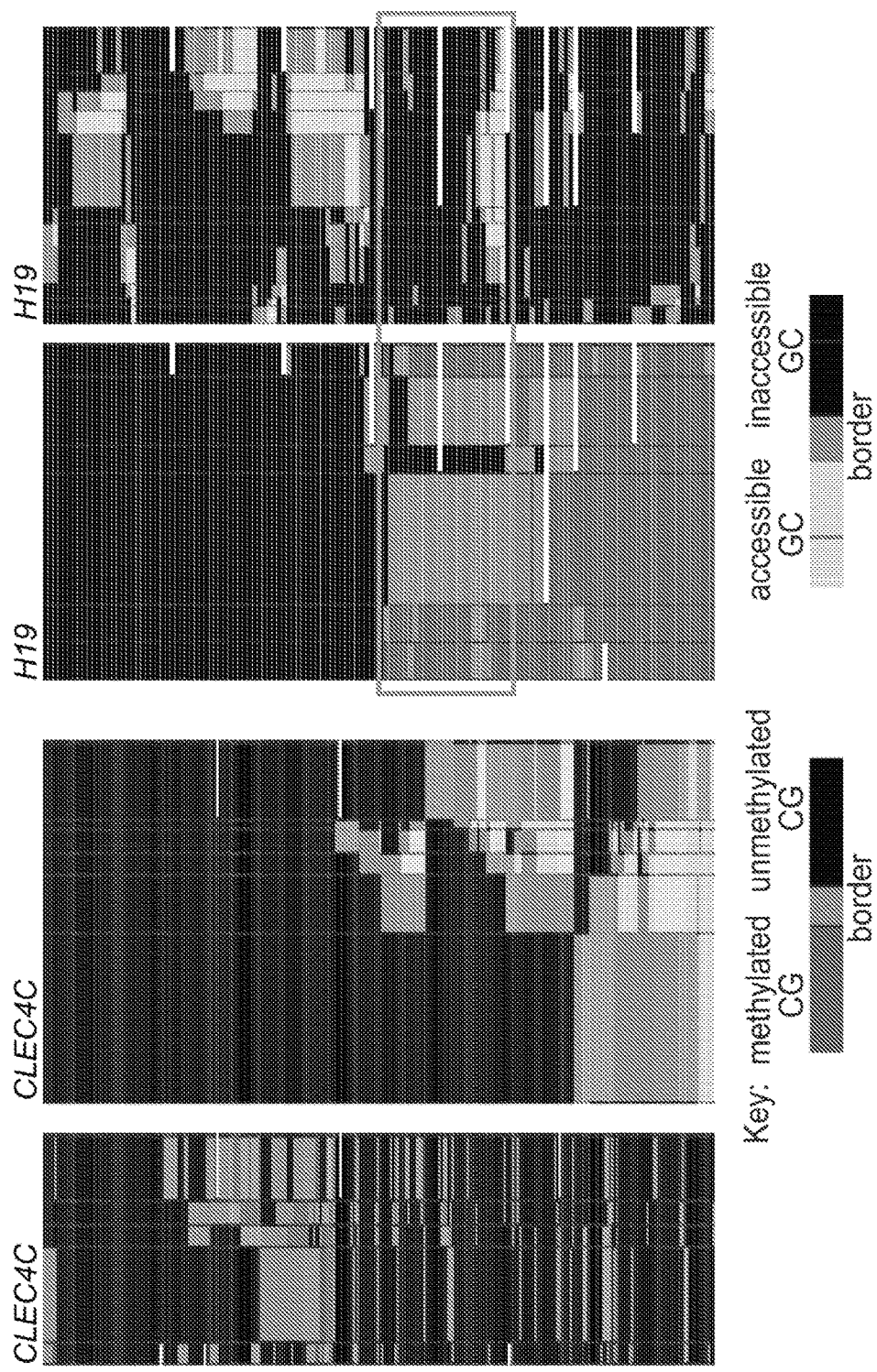

FIG. 12. GC accessibility is restricted to unmethylated molecules in a subset of variable methylated promoters. CG methylation (left) and GC accessibility (right) are shown for the H19 and CLEC4C promoters. Parsing of the molecules according to CG methylation status shows that GC accessibility is largely restricted to unmethylated molecules. Note that the accessibility seen for methylated molecules at H19 occurs within a subset of the molecules that exhibit a local depletion of DNA methylation in the center of the amplicon.

Figure 8:
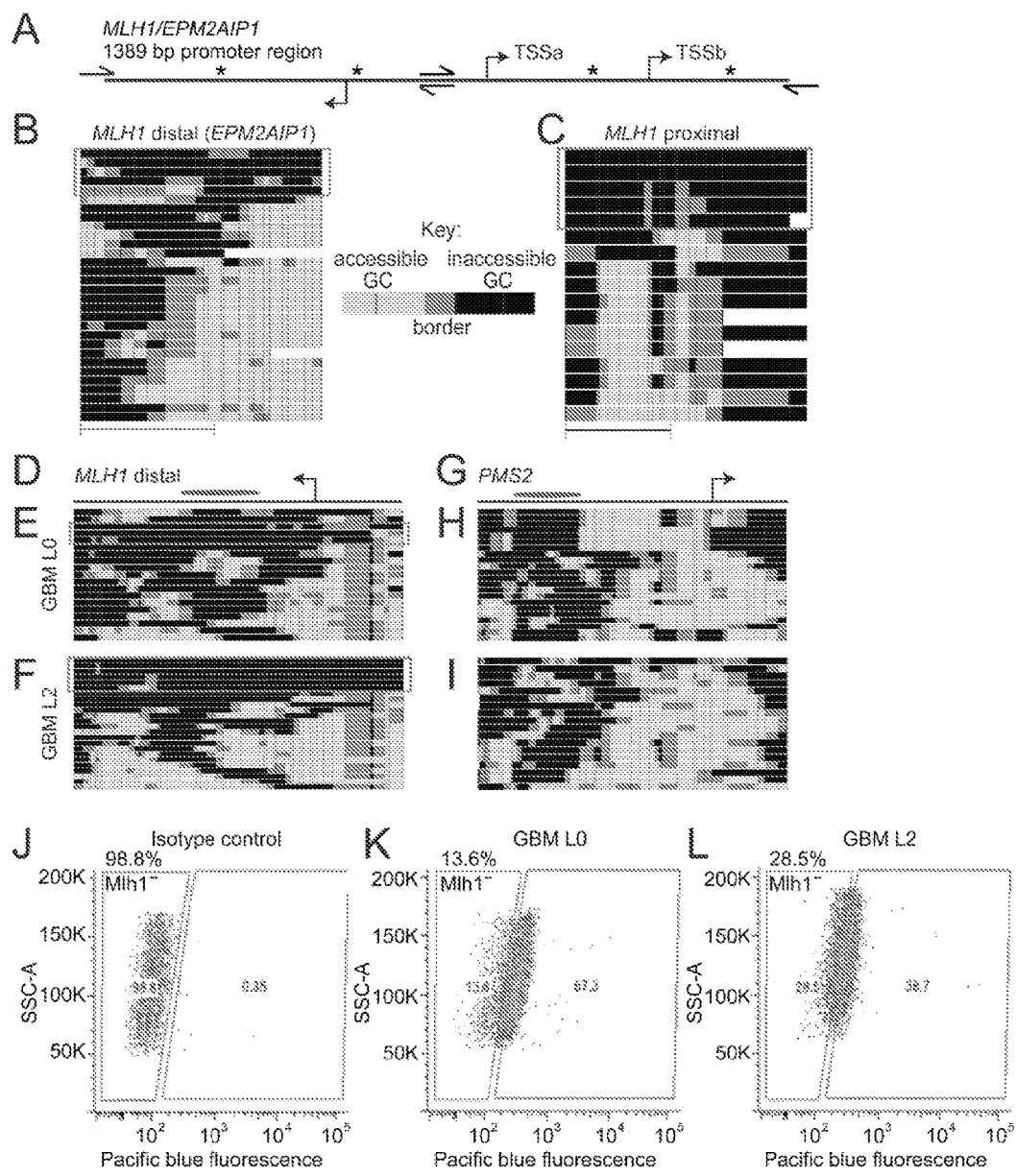

FIGS. 13A-13F. DNA methylation and chromatin accessibility at the proximal MLH1 promoter. Diagrams of the proximal (A) and distal (D) MLH1 promoter are shown with TSSs indicated with bent arrows and gray ellipses indicating 147 bp. MAPit-BGS CG methylation (B) and GC accessibility (C) data for GBM L0 and GBM L2 are shown. Both samples exhibit inaccessible molecules that are highlighted with a cyan rectangle (15% of GBM L0 and 25% GBM L2). These patterns are consistent with those observed at the distal promoter (FIG. 8). In contrast, GC accessibility data from NSC (E) shows only one molecule with inaccessible chromatin (5% of molecules). Immunostaining with anti-Mlh1 antibody and flow cytometry of expanded TMZ-tolerant cells is shown (F).

Figure 14:
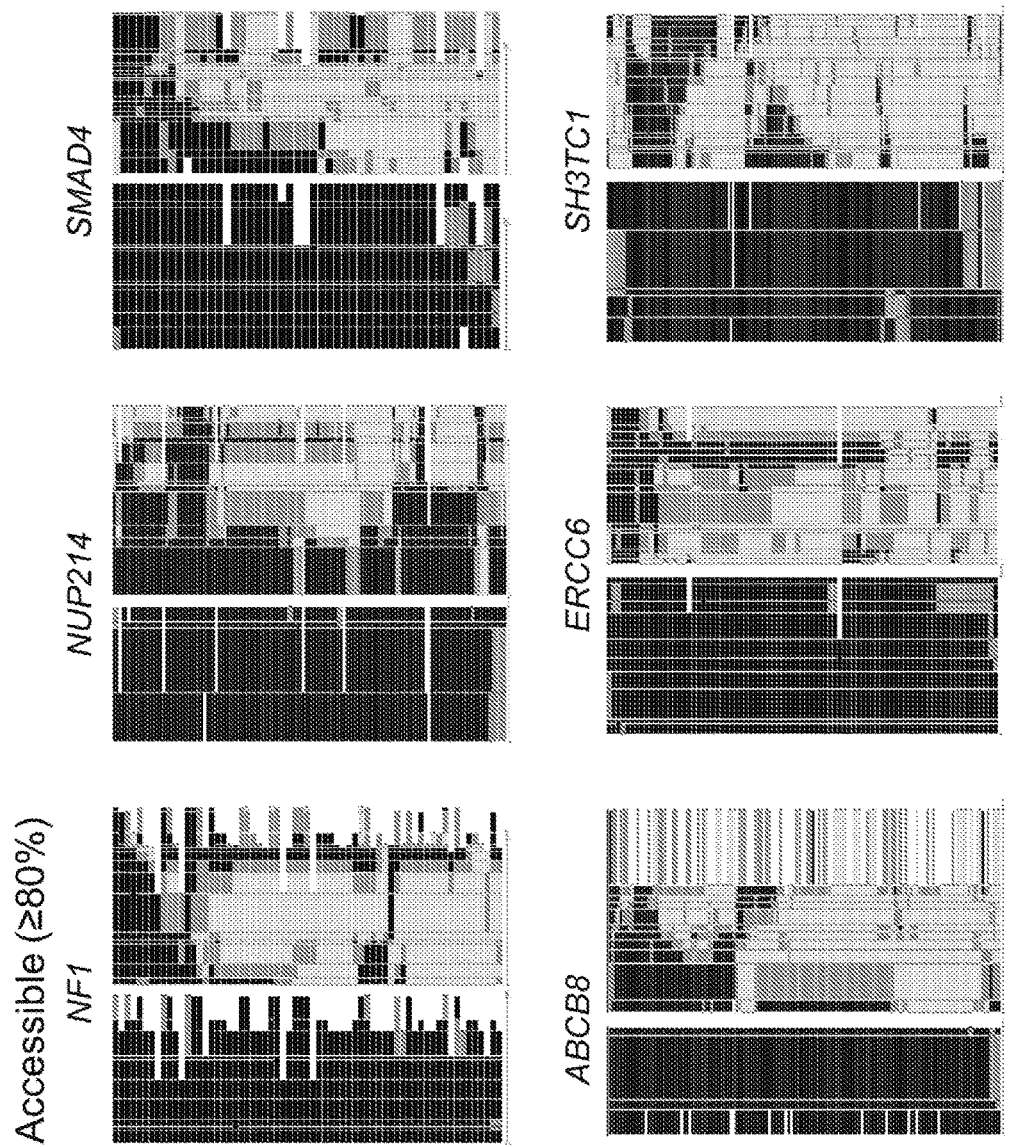
Figure 14:
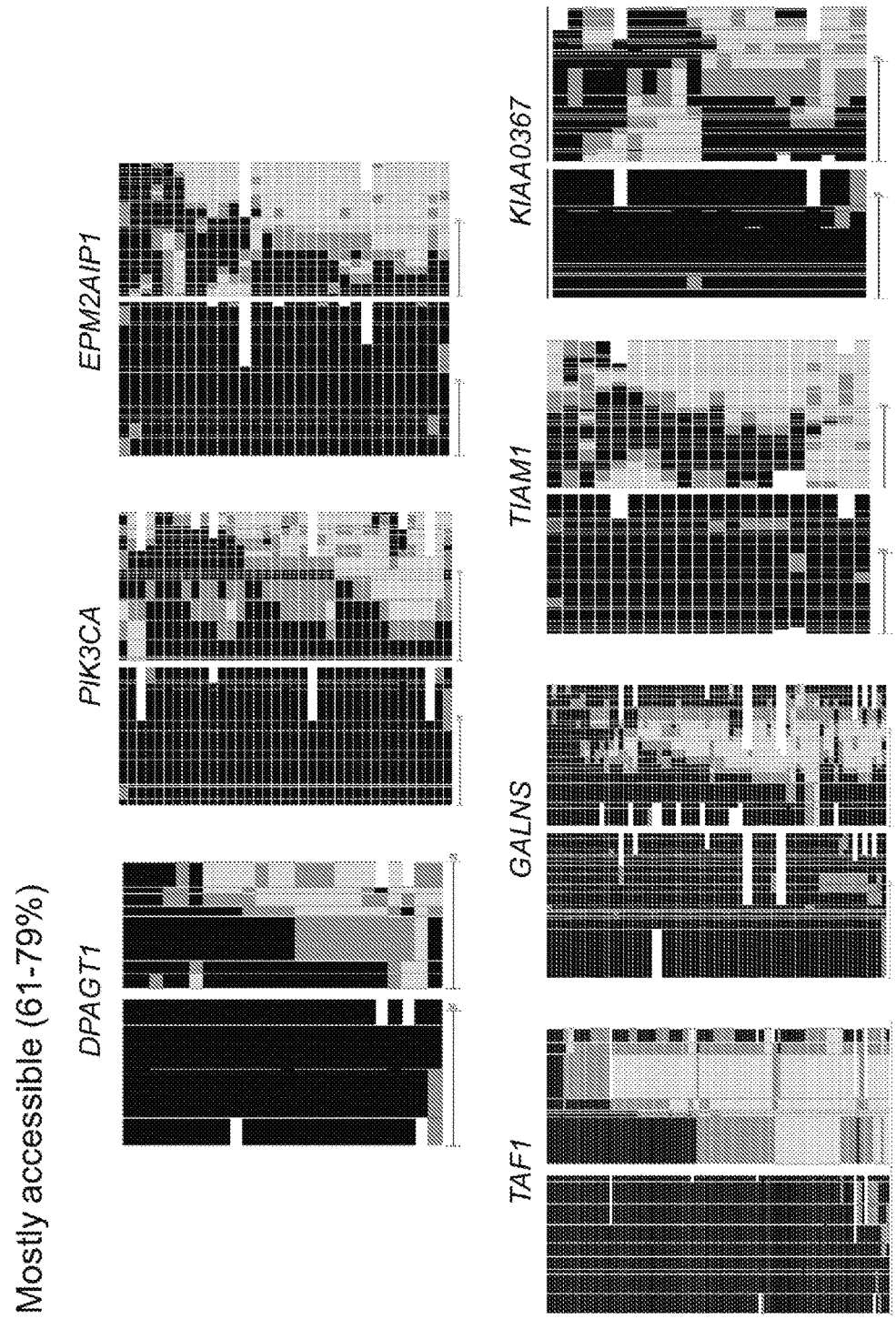
Figure 14:
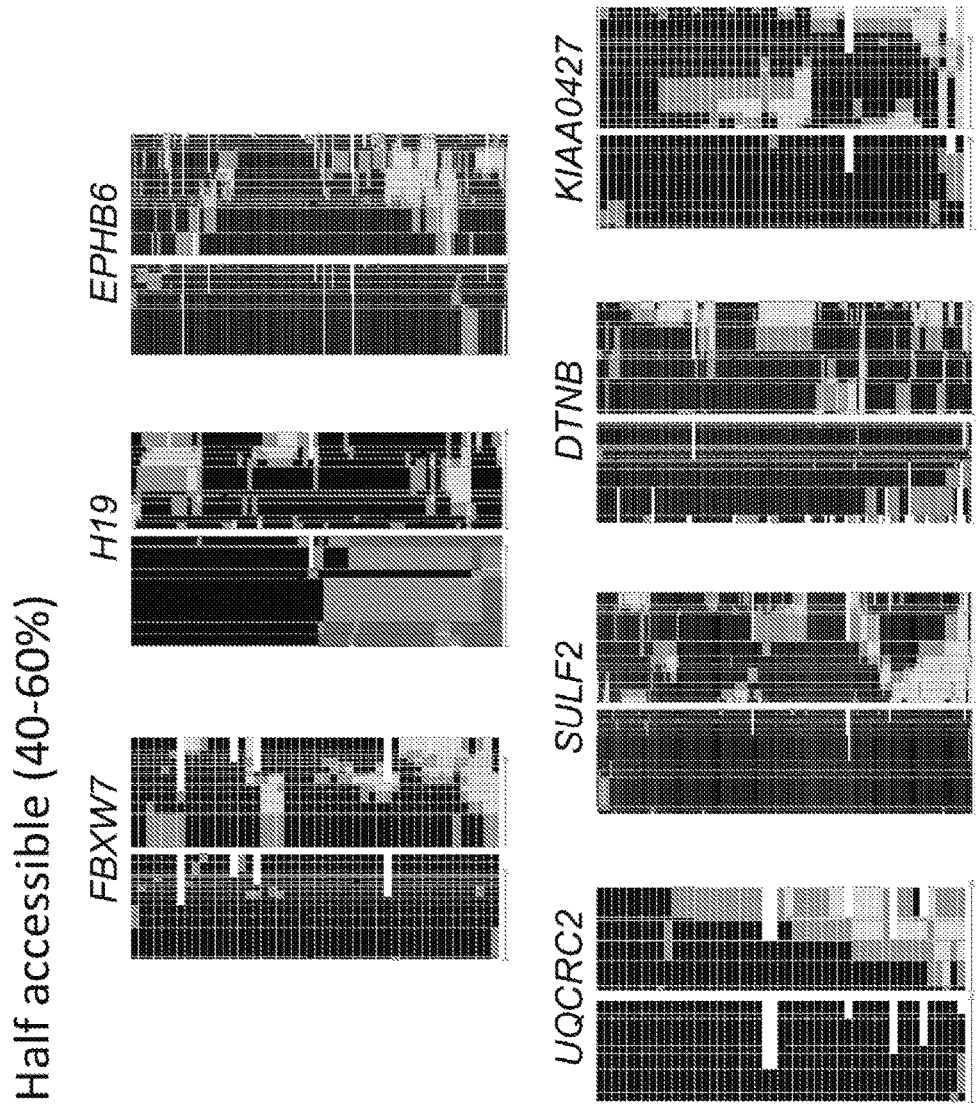
Figure 14:
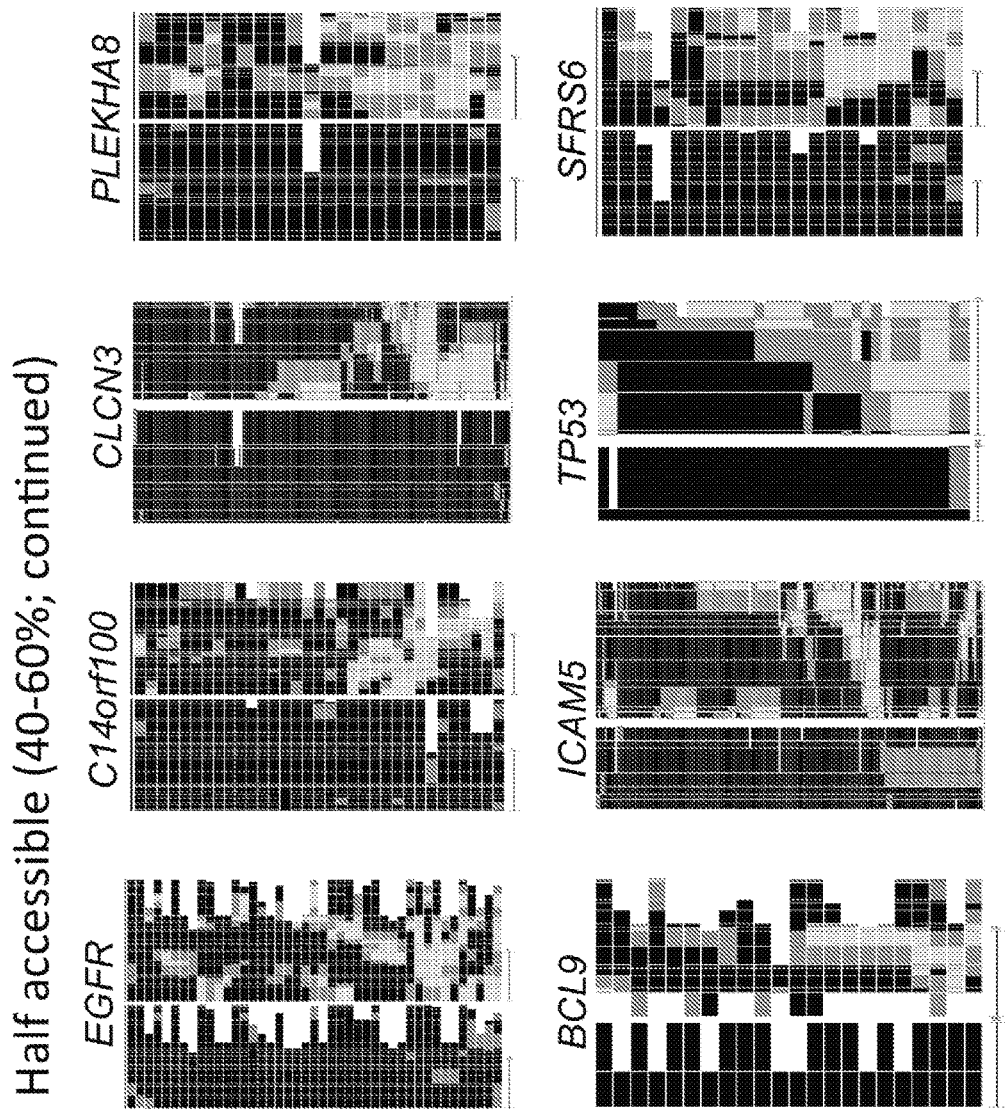
Figure 14:
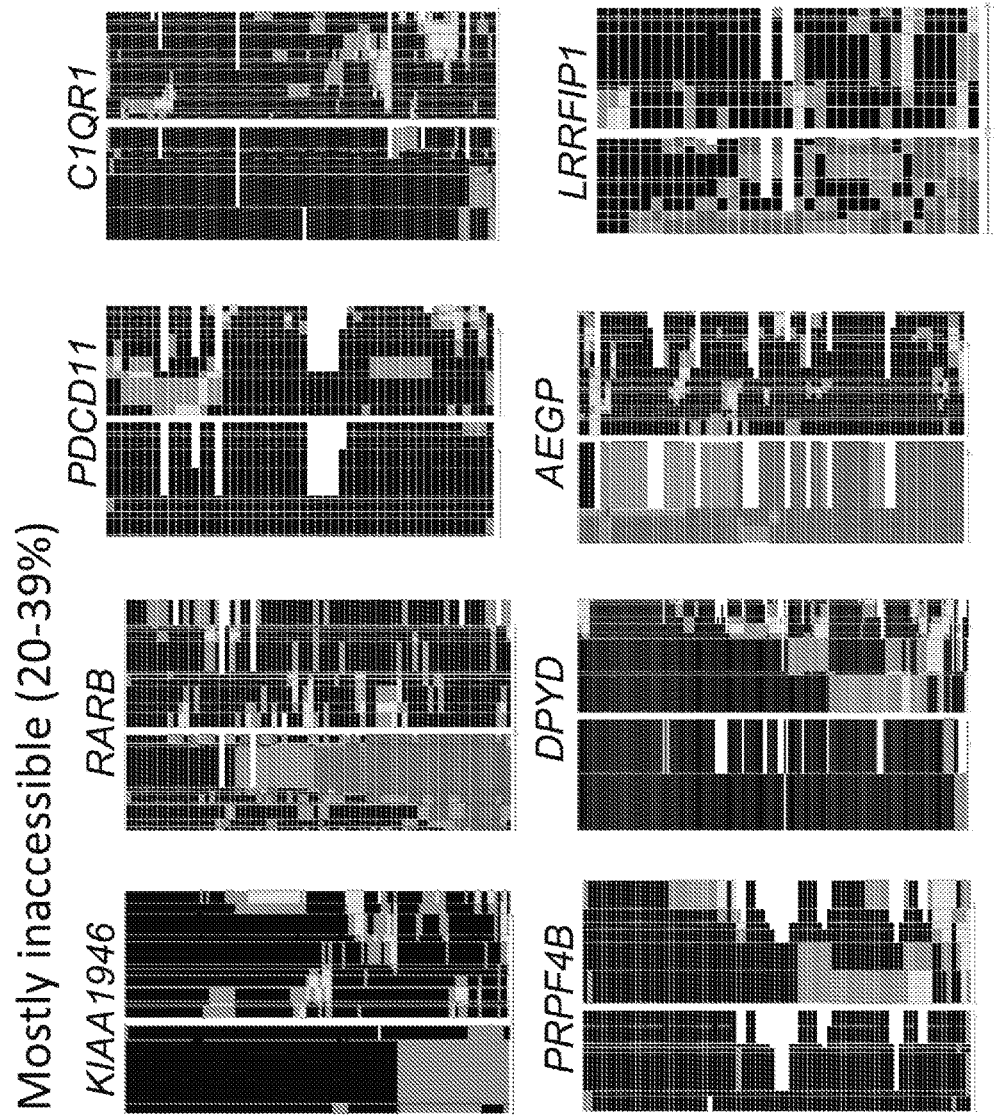
Figure 14:
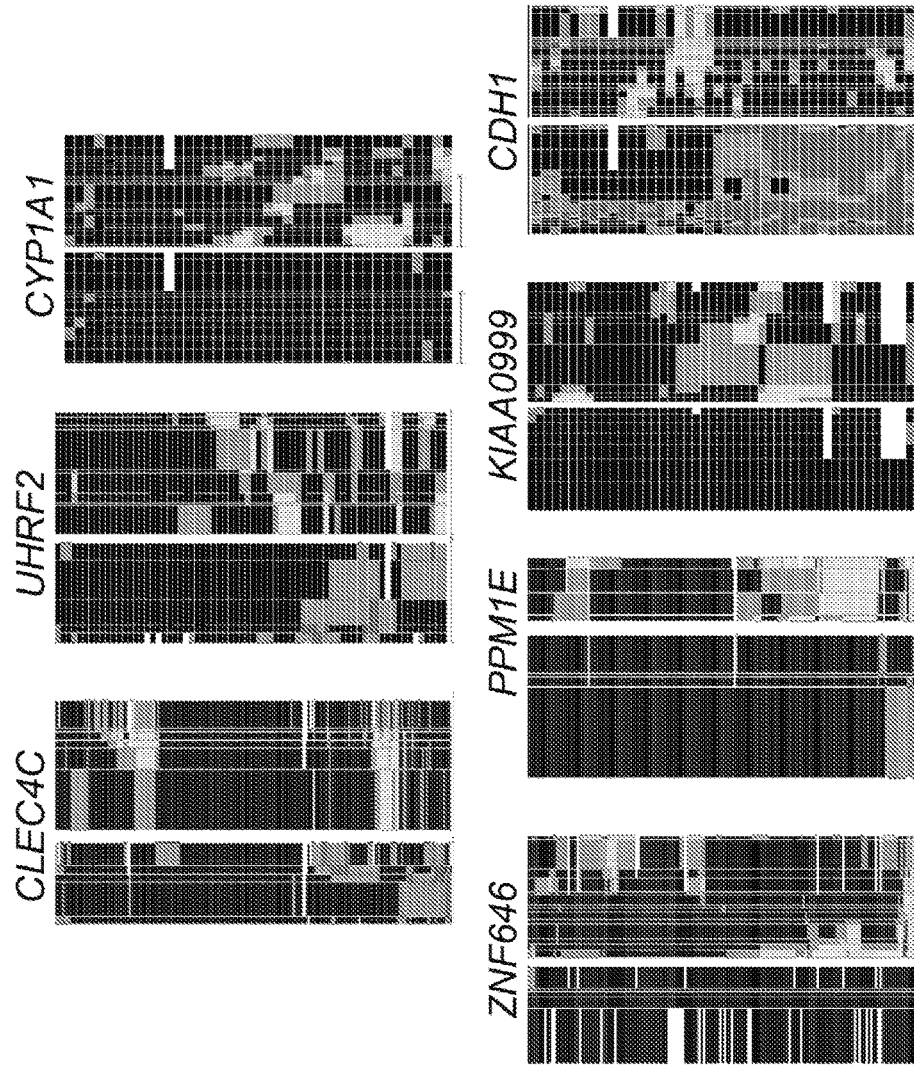
Figure 14:
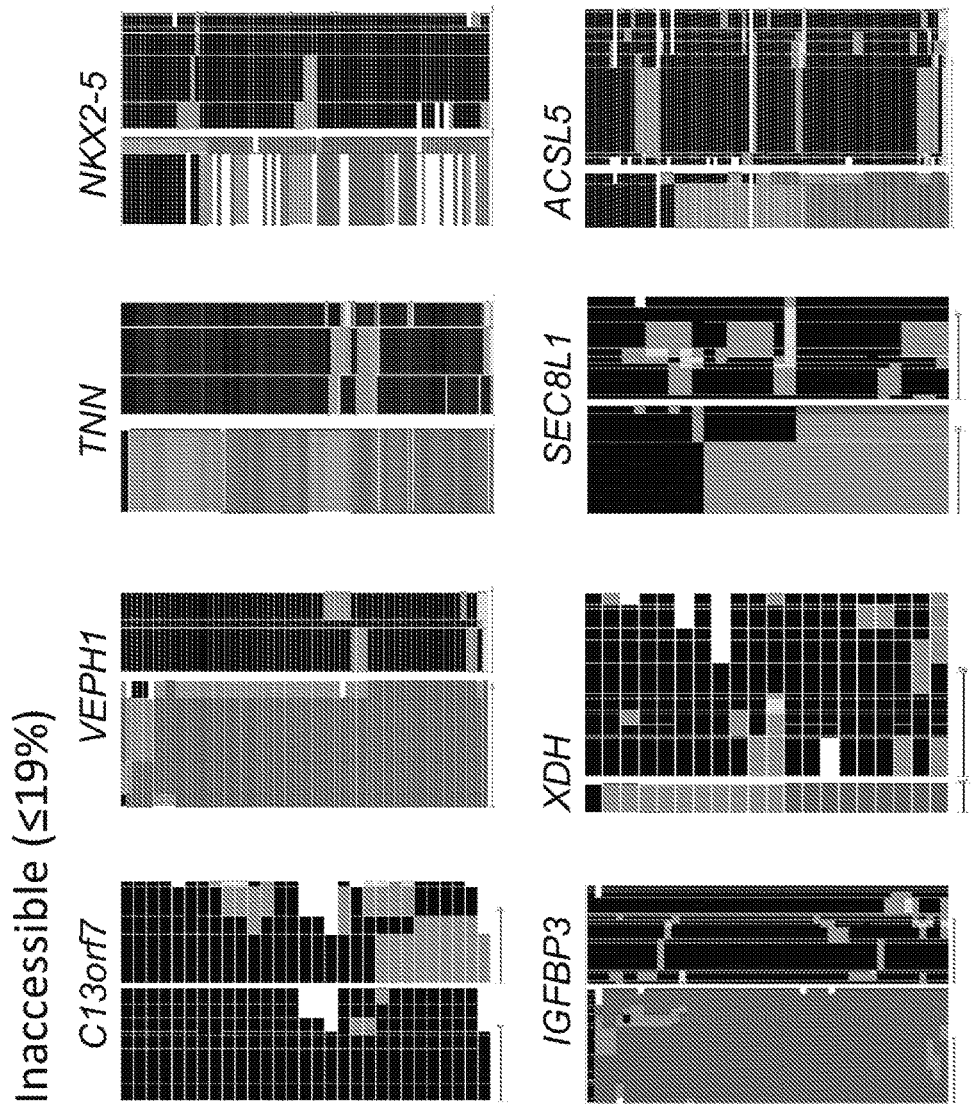
Figure 14:
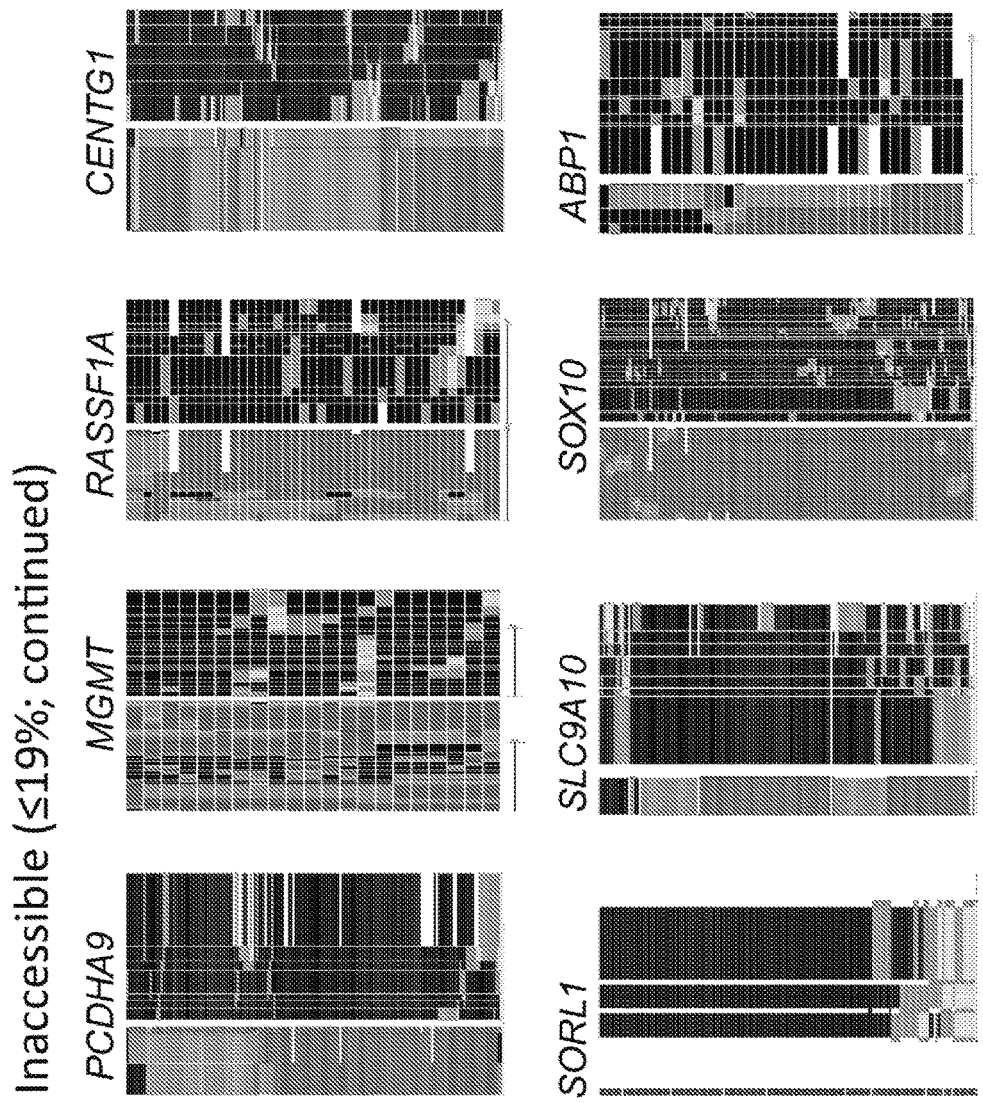
Figure 14:
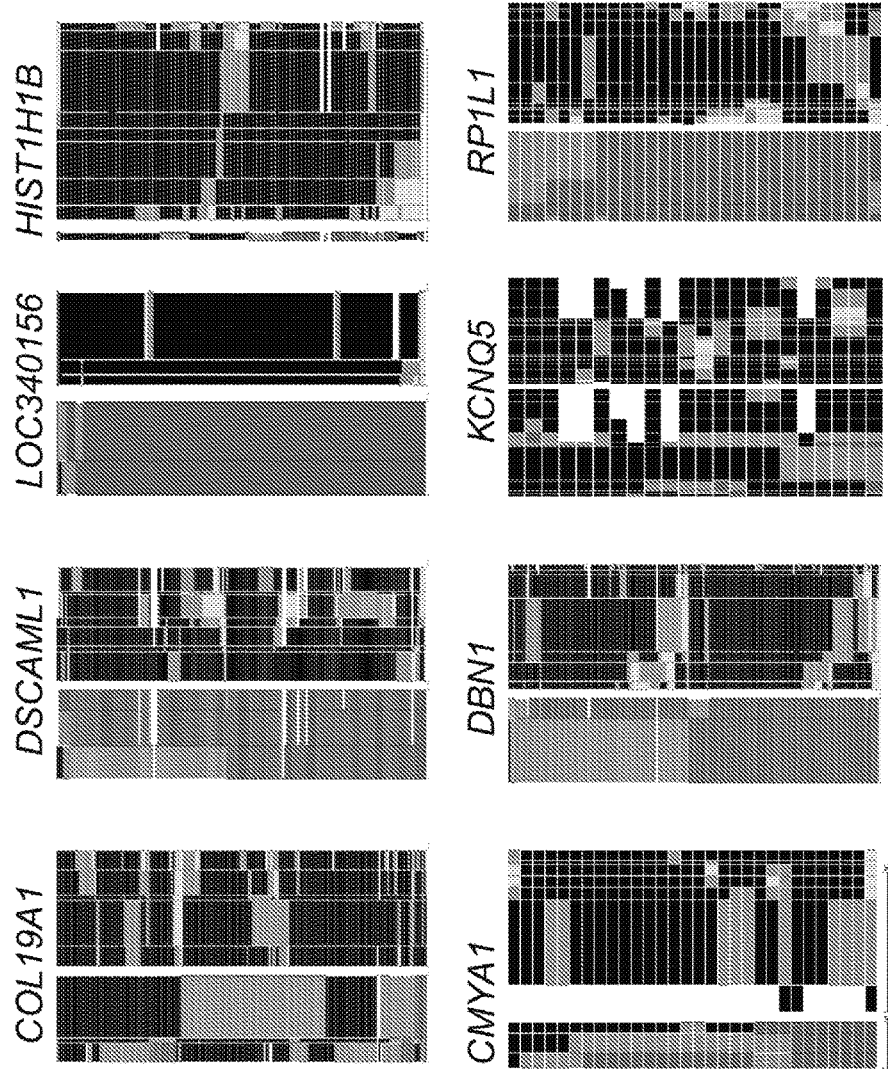

FIG. 14. MAPit-patch images showing CG methylation (left) and GC accessibility (right) of target loci in each of the five classes defined in FIG. 6B.

Figure 15:
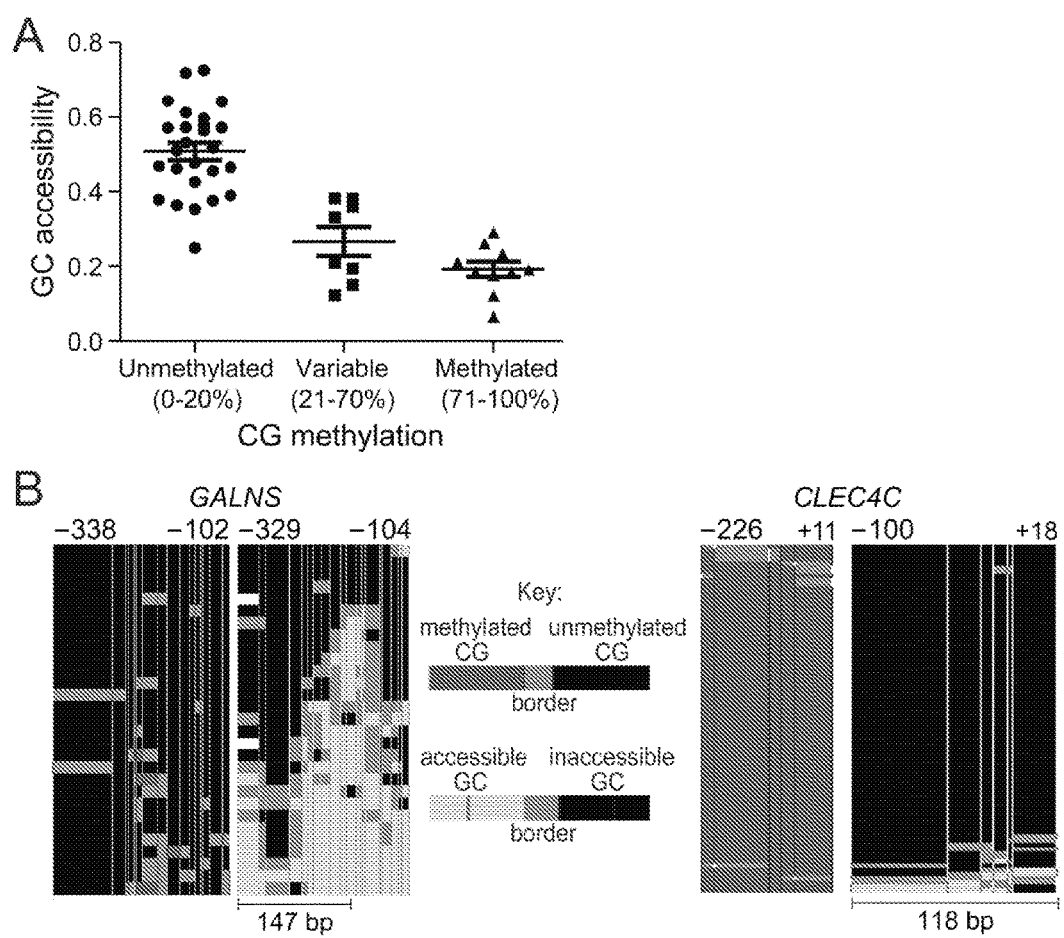

FIGS. 15A-15B. MAPit-patch using delivery of a DNA methyltransferase probe in live cells identifies accessible and inaccessible promoters. HCT116 colorectal cancer cells were transiently transfected with vector pLenti CMV/TO GFP-Zeo (Addgene plasmid 17431) containing separate genes encoding M.CviPI (with C-terminal Myc tag) and green fluorescent protein (GFP), both optimized for human codon preferences and expression driven by the strong, constitutive cytomegalovirus promoter. Cells were harvested 24 hrs post-transfection by trypsinization and subjected to fluorescence-activated cell sorting to collect cells expressing GFP, and by extension, M.CviPI. Genomic DNA was extracted, processed, sequenced, and data analyzed according to the MAPit-patch protocol. Inverse correlation between GC accessibility and endogenous CG methylation in (A) the overall set of MAPit-patch amplicons analyzed and (B) hypomethylated and highly accessible GALNS promoter (left) and hypermethylated and relatively inaccessible CLEC4C promoter (right). The inverse correlation between GC accessibility and endogenous CG methylation in A and B indicate that delivery of M.CviPI to live cells accurately identifies accessible and inaccessible chromatin.

Figure 16:
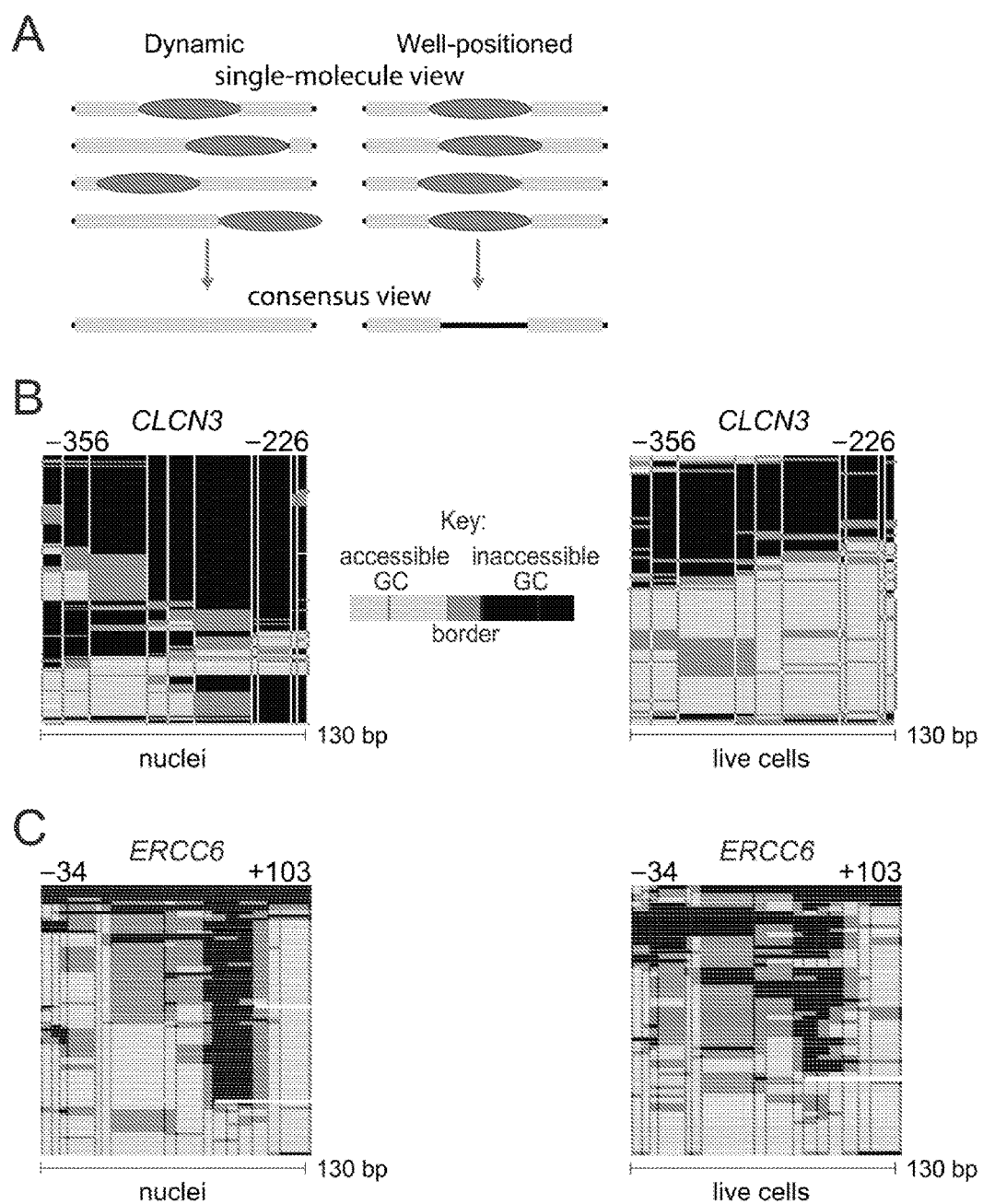

FIGS. 16A-16C. MAPit-patch using delivery of a DNA methyltransferase probe in live cells reveals dynamic chromatin. (A) Probing of chromatin in live cells offers a means by which to identify regions of dynamic occupancy by DNA-binding factors. The example shows depicts four single molecules and the overall consensus view of chromatin accessibility at two different hypothetical loci. In the case where a nucleosome (blue oval) is highly dynamic (left), i.e., occupies several distinctly different positions, on average, molecules will exhibit accessibility over a broader region. By contrast, in the case where a nucleosome is well-positioned, i.e., occupies a fairly constant position, the central region of the nucleosome will be protected against exogenous methylation. Comparison of chromatin accessibility data at promoters exhibiting either (B) dynamically moving nucleosomes, for example at the CLCN3 promoter, or (C) a fairly well-positioned DNA-binding factor, for example at the ERCC6 promoter, obtained from probing either nuclei with purified M.CviPI in the presence of methyl donor cofactor (S-adenosyl methionine) for 15 min (left) versus in live cells 24 hrs post-transfection of pLenti CMV/ TO M.CviPI-Myc (right). Note that at the less dynamic ERCC6 locus, probing either in nuclei or in live cells yields similar results, whereas the more dynamic CLCN3 locus exhibits increased overall chromatin accessibility in live cells compared with nuclei.

FIGS. 17A-17B. Accessible chromatin is modified in live cells after delivery of either of two additional DNA methyltransferases. Quantitative Methylation-sensitive Restriction Enzyme (qMSRE) analysis indicates that transient transfection of (A) M.CviPII (recognition sequence CCD, first C modified, where D is A, G or T) and (B) M.CviQII (recognition sequence RAG, where R is A or G) leads to methylation of accessible target sites. Cells were transfected with vector pcDNA3.1+encoding either M.CviPII-Myc or M.CviQII-His$_6$ and collected after 24 hrs. Cells transfected with M.CviPI-Myc and non-transfected cells were also collected as positive and negative controls, respectively. Genomic DNA was extracted and digested with either R.HaeIII (for M.CviPI and M.CviPII transfections) or R.AluI (for M.CviQII transfection). These restriction enzymes are sensitive to DNA methylation; R.HaeIII activity is blocked by overlapping methylation by M.CviPI or M.CviPII and R.AluI activity is blocked by methylation by M.CviQII. Thus quantitative measurement of DNA methyltransferase activity can be determined following restriction digest and qPCR with primers flanking a restriction enzyme target site at an accessible promoter. Protection against restriction enzyme activity is observed following transfection with the DNA methyltransferases but no protection is observed in non-transfected controls.

DETAILED DISCLOSURE OF THE INVENTION

The current invention provides a method of simultaneously determining methylation state and chromatin structure of target loci, the method comprising the following steps:
a. providing a cell containing genetic material,
b. isolating or preparing the genetic material (e.g., chromosomes or chromatin) from the cell,
c. treating the genetic material with a DNA methyltransferase,
d. purifying the genetic material treated with the DNA methyltransferase,
e. digesting the purified genetic material with a DNA restriction enzyme,
f. optionally purifying the digested genetic material or inactivating the DNA restriction enzyme,
g. contacting the digested genetic material in conditions that allow hybridization of complementary DNA with a set of oligonucleotides, wherein the set of oligonucleotides comprise:
   a. patch-1 which can hybridize with a first universal priming sequence (U-1),
   b. patch-2 which can hybridize with a second universal priming sequence (U-2), U-2 also having one or more exonuclease-resistant 3' end modifications and 5' end phosphate modification,
   c. an upstream patch having a DNA sequence, from 3' to 5' end, comprising: a sequence which hybridizes with a first universal priming sequence (U-1) and a sequence which hybridizes with a region at the 5' end of one DNA strand of the target loci,
   d. a downstream patch having a DNA sequence, from 5' to 3' end, comprising: a sequence which hybridizes with a second universal priming sequence (U-2) and a sequence which hybridizes with a region at the 3' end of one DNA strand of the target loci,
h. ligating a first universal priming sequence (U-1) and a second universal priming sequence (U-2) with the target loci to form DNA strands, each comprising: one DNA strand of the target loci flanked by a first universal priming sequence (U-1) at the 5' end and a second universal priming sequence (U-2) at the 3' end,
i. purifying the target loci ligated with a first universal priming sequence (U-1) and a second universal priming sequence (U-2) by digesting the reaction mixture with one or more exonucleases that cleave DNA molecules from 3' end to 5' end,
j. treating the purified target loci ligated with a first universal priming sequence (U-1) and a second universal priming sequence (U-2) with bisulfite,
k. purifying the bisulfite-treated target loci ligated with a first universal priming sequence (U-1) and a second universal priming sequence (U-2),
l. amplifying the bisulfite-treated target loci ligated with a first universal primer and a second universal primer using polymerase chain reaction (PCR), wherein the primers for the PCR comprise:

a. a first PCR amplification primer having a DNA sequence from 3' to 5' end comprising, the first universal primer sequence (U-1), optionally, a sample-specific barcode and a first adapter sequence specific for a sequencing platform, and
b. a second PCR amplification primer having a DNA sequence from 3' to 5' end comprising, a complementary sequence to the second universal primer sequence (U-2), optionally, a sample-specific barcode, and a second adapter sequence specific for a sequencing platform, m. purifying the PCR amplification products (e.g., using PCR purification spin columns and/or agarose gel extraction), and n. sequencing the PCR amplification product by the sequencing platform to determine the methylation state and chromatin structure of the target loci.

The current invention provides a method for determining whether the target loci are 1) unmethylated and inaccessible; 2) unmethylated and accessible; 3) methylated and inaccessible; or 4) methylated and accessible, wherein the sites within nucleosomes or those occluded by DNA-bound non-histone proteins are inaccessible and sites outside nucleosomes or those free of non-histone proteins are accessible.

In an aspect of the invention, methylation state and chromatin structure of target loci is compared between different cells by treating the cells according to MAPit-patch method and analyzing the sequence of the target loci to elucidate the differences in the methylation state and chromatin structure of different cells. In an embodiment of the invention, methylation state and chromatin structure of a plurality of gene promoters is compared between cells. For example, methylation state and chromatin structure of promoters of a plurality of genes can be compared in cancerous cells and non-cancerous cells to identify genes associated with cancer. The difference in the chromatin structure and methylation state in the promoters of these genes can be associated with the difference in the expression of these genes in cancerous cells versus non-cancerous cells. Alternately, the method of the current invention can be used to analyze methylation state and chromatin structure of promoters of genes known to be involved in cancer to identify the presence of a cancerous cell in a group of cells or to identify the presence of a drug-tolerant cell in a group of cells.

Chromatin structure indicates the state of genetic material with respect its packaging and accessibility. Epigenetic modifications such as phosphorylation, acetylation, methylation and ubiquitination at specific amino acid residues on the histone tails influence higher-order chromatin structure that regulates the nuclear processes, such as transcription, chromosome packaging and DNA damage repair. Transcriptionally active chromatin is generally accessible, whereas transcriptionally inactive chromatin is generally inaccessible to DNA methyltransferase enzymes.

Mononucleosomes refers to a single monomer of the nucleosome array. Due to the number of potential binding interactions on the histone tails, histone globular domain and the nucleosomal DNA, mononucleosomes can offer a simplified substrate for chromatin analysis. Understanding the position of nucleosomes can help provide information about chromatin context and gene regulation. Traditional methods used to identify nucleosome positioning include nuclease digestions methods which rely on the fact that a nucleosome bound to DNA will protect the DNA from enzymatic digestions. However, these techniques destroy the physical linkages between binding sites and therefore are designed to look at average distribution across a panel of remodeled nucleosomes and not to determine the status of a single DNA molecule. The current invention provides information about nucleosome occupancy, binding of non-histone proteins to DNA, methylation state, and transcriptional activity at target loci in greater detail.

The genetic material which can be used for the current invention comprises methylated DNA. In certain embodiments, the genetic material is chromatin that is prepared or isolated from the cell. The methods of isolating the genetic material from cells are well known to a person of ordinary skill in the art. In an embodiment of the invention, the amount of genetic material used per reaction is about 10 ng to about 800 ng, preferably about 100 ng to about 700 ng, more preferably about 200 ng to about 600 ng, and even more preferably about 300 ng to about 500 ng.

Treatment of the genetic material with one or more DNA methyltransferases methylates substantially all of the genetic material capable of being methylated. The genetic material can be methylated after preparation or isolation from a cell. Alternatively, the genetic material may be methylated prior to preparation or isolation from a cell (e.g., the genetic material is isolated from cells expressing DNA methyltransferases).

DNA methyltransferase used in the current invention can methylate cytosine residues or adenine residues in target sites. In an aspect of the invention the DNA methyltransferase used in the method of current invention methylates cytosine residues on the N4 or C5 position; in the case of C5, within the double-stranded dinucleotide recognition sequence 5' . . . GC . . . 3'. Thus, examples of target sites for DNA methyltransferases include, but are not limited to, CpG, GpC, CpHpG, CpHpH, CpCpD, etc., where H represents A, G or T, and D represents A, G or T. For the purposes of this invention "C-methylation site" refers to a site that can be methylated by a DNA methyltransferase.

The C-methylation site referred to in the present invention may be associated with nucleosomes or tight-binding factors. A term "C-methylation site capable of being methylated" refers to a C-methylation site that the DNA methyltransferase can access and methylate. A term "C-methylation site not capable of being methylated" refers to a C-methylation site that the DNA methyltransferase cannot access and methylate because the site is protected by (or associated with) either a nucleosome, or a tight binding factor. In connection with the present invention, the C-methylation sites not capable of being methylated thus provide a "footprint" of the position of the nucleosome and/or the tight binding factors in the chromatin.

Treatment with DNA methyltransferase is carried out under conditions that maintain chromatin integrity. Maintaining chromatin integrity involves avoiding changes in physical and chemical properties of the genetic material. Maintaining chromatin integrity ensures that DNA methyltransferase acts on the genetic material as it exists in living cells. Therefore, the conditions are controlled to avoid fragmentation of DNA, dissociation of histones and non-histone proteins bound to DNA, changes in nucleosome structures, changes in endogenous methylation status, and other changes to DNA strands that can affect the ability of DNA methyltransferases to methylate a site on DNA strand. Appropriate conditions for DNA methyltransferase treatment without affecting the integrity of the genetic material involve controlling temperature, pH, presence and/or concentration of salts, presence and/or concentration of reducing agents, etc. Various conditions that are appropriate for carrying out DNA methyltransferase treatment are within the knowledge of a person of ordinary skill in the art.

Various DNA methyltransferases can be used for the method of current invention. As indicated above, any methyltransferase that introduces methyl groups into cytosines (e.g., N4-methylcytosine, 5-methylcytosine, etc.), and that can be detected by patch bisulfite PCR can be used. Examples of DNA methyltransferases that can be used in the method of current invention include, but are not limited to, CpG DNA methyltransferase (M.SssI; Renbaum et al. 1990) and GpC DNA methyltransferase (M.CviPI; Xu et al. 1998), both commercially available from New England Biolabs. CpCpD DNA methyltransferase (M.CviPII) has also been reported (Chan et al. 2004). Other DNA methyltransferases suitable for use in the context of this disclosure can be identified in the Restriction Enzyme Database (REBASE) (see web site: rebase.neb.com, Roberts et al. 2010, Nucleic Acids Res., 28:D234-D236). M.CviPI is isolated from a recombinant strain of *E. coli* that contains the DNA methyltransferase gene cloned from *Chlorella* virus. This construct is fused to the maltose binding protein (MBP). A person of ordinary skill in the art recognizes that any DNA methyltransferase capable of selectively methylating nucleotides can be used in the method of the current invention. In other embodiments, DNA methyltransferases that introduce methyl groups into other residues, such as adenine (e.g., N6-methyladenine) can be used in the method of the current invention. For example, DNA methyltransferases that methylate RAG (M.CviQII; Chan et al. 2004) or non-specifically methylate A in most sequence contexts (M.EcoGI and M.EcoGII (Fang et al. 2012) have been reported. In further embodiments, 5-methylcytosine can be oxidized to 5-hydroxymethylcytosine (5hmC) and, optionally, covalently linked to a sugar (e.g., glucose), or oxidized fully to 5-carboxylcytosine (5caC) prior to detection of residues modified in the genetic material (reviewed in Song et al. 2012).

Reaction conditions for DNA methylation according to the current invention are maintained so that the DNA methyltransferase methylates substantially all of the sites in the genetic material capable of being methylated by the DNA methyltransferase and does not methylate almost any of the sites in the genetic material not capable of being methylated. Maintaining reaction conditions for the current invention comprise providing an "effective amount" of DNA methyltransferase and methyl-donating agent. An example of methyl donor is S-adenosyl methionine. An "effective amount" of the DNA methyltransferase and methyl-donating reagent is an amount necessary to methylate substantially all the C-methylation sites capable of being methylated but also sufficiently low to avoid methylation of almost any of C-methylation sites not capable of being methylated.

For purposes of the invention, methylation of substantially all of the C-methylation sites capable of being methylated indicates that the DNA methyltransferase methylates at least 80%, more preferably 90%, even more preferable 99%, and most preferably 100% of all the C-methylation sites capable of being methylated. More particularly, methylation of substantially all of the C-methylation sites capable of being methylated indicates that the DNA methyltransferase methylates at least 80, 81, 82, 83, 84, 85, 86, 87, 88, 89, 90, 91, 92, 93, 94, 95, 96, 97, 98, 99, or 100% of all the C-methylation sites capable of being methylated. For purposes of the invention, methylation of almost none of the C-methylation sites not capable of being methylated indicates that the DNA methyltransferase methylates less than 20%, more preferably 10%, even more preferable 1%, and most preferably 0% of all the C-methylation sites not capable of being methylated. More particularly, methylation of almost none of the C-methylation sites not capable of being methylated indicates that the DNA methyltransferase methylates less than 20, 19, 18, 17, 16, 15, 14, 13, 12, 11, 10, 9, 8, 7, 6, 5, 4, 3, 2, 1, or 0% of all the C-methylation sites not capable of being methylated.

In an embodiment of the invention, about 50 and 500 units of C-methylation methyltransferase are used in a reaction as a function of the number of cells containing genetic material that will be methylated. As an example, a unit is defined as the amount of GpC DNA methyltransferase required to protect 1 µg of lambda DNA in a total reaction volume of 20 µl in 1 hour at 37° C. against cleavage by HaeIII restriction endonuclease. In another embodiment of the current invention, 100 U C-methylation DNA methyltransferase is used in a reaction.

In an aspect of the invention, the methylated genetic material is purified after treatment with DNA methyltransferase. Any method which does not substantially affect the methylation state or sequence of the DNA can be used. In an embodiment of the invention the genetic material is purified after methylation by phenol/chloroform extraction and ethanol precipitation. Other methods of purifying the methylated DNA are within the purview of a person of ordinary skill in the art.

Digesting the methylated genetic material refers to treating the methylated genetic material with restriction endonucleases. Various restriction endonucleases can be used in the current invention. The restriction endonucleases that can be used in the current invention provide abundant recognition sequence frequency (for example, a 4-base pair recognition sequence), insensitivity to methylated cytosine, ability to efficiently digest DNA, and be inactivated by heat to avoid additional purification steps.

In an embodiment of the invention, enzyme AluBI is used to digest the genetic material treated with DNA methyltransferase. AluI is isolated from *Arthrobacter luteus* and AluBI is an isoschizomer of AluI isolated from *Arthrobacter luteus* B and is insensitive to the presence of 5-methylcytosine in the recognition sequence "AGCT." Additional enzymes that can be used in the current invention include, but are not limited to, MseI and DpnII.

In another embodiment of the invention, the methylated and digested genetic material can be purified from the reaction mixture. In another embodiment of the invention, the restriction enzyme is inactivated, for example, by heat or other agents that can inactivate proteins.

Methylated nucleotides can be identified directly or indirectly. For example, $m^5C$ can be indirectly identified using the bisulfite sequencing methods (bisulfite conversion followed by PCR and DNA sequencing) disclosed herein. Other indirect methods of detecting methylated nucleotides can also be used. Methylated nucleotides can also be directly detected, for example, by using single-molecule real-time (SMRT) sequencing (on, for example, a Pacific Biosciences RSII instrument) or by Oxford nanopore sequencing.

This disclosure also embraces detecting modified nucleotides by other known methods. For example, one may chemically or enzymatically convert any modified (methylated) nucleotide to a second modification and detect the second modification of the on the nucleotide. For example, $m^5C$ can be sequentially oxidized by Ten-eleven translocation (TET) family dioxygenases to 5-hydroxymethylcytosine (5hmC), 5-formylcytosine (5fC) and ultimately to 5-carboxylcytosine (5caC) which is then detected. Alternatively, 5hmC can be enzymatically coupled to glucose by beta-glucosyltransferase activity as is done in the TAB-seq protocol, which could enhance its detection properties SMRT sequencing. 5hmC is also oxidized by $KRuO_4$ in oxidative bisulfite sequencing. 5hmC can also be deaminated by AID or APOBEC to 5hmU, which can be detected as is routinely done by bisulfite sequencing (see, for example, Song et al. 2012). In addition, bacteriophage Mu contains an enzyme that modifies DNA to dA'x=alpha-N-(9-beta-D-2'-deoxyribofuranosylpurin-6-yl)-glycinamide, which can be degraded by acid hydrolysis to N6-carboxymethyladenine and then detected (Swinton et al. 1983). In a further aspect of the invention, the methylated and digested genetic material is contacted, under conditions that allow hybridization of complementary DNA, with a set of oligonucleotide molecules, wherein the set of oligonucleotide molecules comprise:

1. patch-1 which can hybridize with a first universal priming sequence (U-1),
2. patch-2 which can hybridize with a second universal priming sequence (U-2) and U-2 being modified with one or more exonuclease-resistant 3' end modifications and 5' phosphate modification,
3. a plurality of upstream patches, each having a DNA sequence, from 3' to 5' end, comprising: a sequence which hybridizes with a first universal priming sequence (U-1) and a sequence which hybridizes with a region at the 5' end of one of the target loci,
4. a plurality of downstream patches, each having a DNA sequence, from 5' to 3' end, comprising: a sequence which hybridizes with a second universal priming sequence (U-2) and a sequence which hybridizes with a region at the 3' end of one of the target loci.

The first and the second universal priming sequences (U-1 and U-2) are designed to be resistant to bisulfite conversion. For example, U-1 and U-2 may be devoid of cytosine (to prevent bisulfite conversion). Alternatively, U-1 and U-2 may contain methylated cytosine residues (methylated, for example, at C5 or the exocyclic nitrogen atom N4). Further, at least one of U-1 or U-2 is modified with one or more end modifications that render at least one of U-1 or U-2 resistant to exonucleases. These modifications may include, but are not limited to, adding a carbon spacer (e.g., a spacer of 3, 4, 5, 6, 7, 8, 9, 10 carbons, or in some embodiments a higher number of carbon atoms) on the 3' end and/or one or more phosphorothioate modifications at one or both ends of U-2 or one or both ends of U-1. In certain embodiments, the 5' end of U-1 and the patch oligonucleotides may modified to provide resistance to exonucleases (e.g., by the addition of a carbon spacer and/or phosphorothioates) and the 3' end of U-1 is left unmodified. In certain embodiments, up to 10 phosphorothioate modifications are added to the 5' and/or 3' end of the U-1 or U2 oligonucleotides. Other embodiments provide that the patch oligonucleotides are also rendered exonuclease resistant to exonucleases (e.g., by the incorporation of phosphorothioates at one or both ends of the patch oligonucleotides).

During the hybridization step, the upstream patches and the downstream patches bind to the 5' ends and 3' ends, respectively, of their corresponding target loci and provide overhangs which can hybridize with first universal priming sequence (U-1) and second universal priming sequence (U-2), respectively. First universal priming sequence (U-1) and second universal priming sequence (U-2) hybridize with the corresponding overhangs provided by upstream and downstream patches. Thus, the upstream and downstream patches capture the target loci and bring first universal priming sequence (U-1) and second universal priming sequence (U-2) immediately adjacent to the target loci.

The conditions that allow hybridization comprise proper temperature, salt concentration, presence/absence of detergents, concentration of detergent if present, pH, presence/absence and concentration of formamide, and presence/absence and concentration of other agents that affect binding ability of complementary DNA. The hybridization conditions can be adjusted to allow hybridization between DNA molecules having high complementarity (85-100% complementary), moderate complementarity (60-85% complementary), or low complementarity (below 60%). In an embodiment of the invention, the hybridization conditions are adjusted to allow hybridization between DNA molecules having high complementarity of about 95, 96, 97, 98, 99, or 100%.

In a further aspect of the invention, first universal priming sequence (U-1) and second universal priming sequence (U-2), which are brought to the 5' and 3' ends, respectively, of the target loci, are ligated to the target loci. In an aspect of the invention, ligase enzyme is used for such ligation. Different choices of ligase enzymes and ligation reaction conditions are well known to a person of ordinary skill in the art and are within the purview of this invention. Ligation produces target loci each with first universal priming sequence (U-1) at the 5' end and second universal priming sequence (U-2) at the 3' end.

In an embodiment of the invention, the genetic material after ligation reaction can be purified from the reaction mixture. In another embodiment of the invention, the ligase is inactivated, for example, by heat or other agents that can inactivate proteins.

In another aspect of the invention, the reaction mixture after ligation or purified genetic material after ligation is treated with one or more exonucleases. In an aspect of the invention, the one or more exonucleases digest DNA strands from 3' to 5' end. Different choices of 3' to 5' exonucleases and the reaction conditions for exonuclease treatment are well known to a person of ordinary skill in the art and are within the purview of this invention. Exonuclease treatment of the genetic material after ligation reaction degrades unhybridized oligonucleotides and the genetic material except the captured and ligated target loci. The target loci ligated with first universal priming sequence (U-1) and second universal priming sequence (U-2) are protected from the exonuclease digestion due to 3' modification of second universal priming sequence (U-2).

A further aspect of the method of the current invention involves purifying the target loci ligated with first universal priming sequence (U-1) and second universal priming sequence (U-2) after exonuclease digestion of unhybridized oligonucleotides and non-targeted genetic material. In another embodiment of the invention, the exonuclease is inactivated, for example, by heat or other agents that can inactivate proteins.

In an even further aspect of the invention, purified target loci ligated with first universal priming sequence (U-1) and second universal priming sequence (U-2) are treated with bisulfite. Bisulfite treatment according to the present invention can be done using methods known to those of ordinary skill in the art. C-methylation sites are subjected to bisulfite conversion using standard methods or commercially available kits, such as the EZ DNA methylation Kit, Cat. Nos. D5001 and D5002, commercially available from Zymo Research.

Treatment of purified target loci with sodium bisulfite converts unmethylated cytosines to uracils; whereas, methylated cytosines remain essentially unchanged. Therefore, bisulfite treatment essentially changes the sequence of unmethylated DNA which includes C-methylation sites not capable of being methylated; whereas, the sequence of methylated DNA, which includes endogenously methylated DNA and C-methylation sites capable of being methylated remain essentially unchanged.

In a further step of PCR amplification, the converted uracil bases are replaced by thymines. Therefore, during sequencing of the bisulfite-treated genetic loci, the unmethylated cytosines appear as thymines, whereas methylated cytosines appear as cytosines.

In an embodiment of the invention endogenous methylation state and chromatin structure of target loci is identified by analyzing the genetic material with or without treatment with exogenous DNA methyltransferase. Comparison of the sequence of genetic material treated with exogenous DNA methyltransferase and after bisulfite treatment can be used to simultaneously elucidate endogenous methylation state and chromatin structure of target loci.

The target genetic loci can be purified after the bisulfite treatment.

In another aspect of the invention, the target genetic loci after bisulfite treatment are amplified by using PCR. The primers for PCR comprise:
  1. a first PCR amplification primer having a DNA sequence from 3' to 5' end comprising, the first universal primer sequence (U-1), optionally a 4-10 bp barcode, and a first adapter sequence specific for a sequencing platform, and
  2. a second PCR amplification primer having a DNA sequence from 3' to 5' end comprising, the second universal primer sequence complementary to U2, optionally a 4-10 bp barcode, and a second adapter sequence specific for the sequencing platform.

The PCR amplification product can be sequenced by a sequencing platform that allows high throughput and multiplexed sequencing of large number of DNA molecules in a single reaction. Examples of sequencing platforms that can be used according to the current invention include, but are not limited to, Roche 454 sequencing platform, Illumina multiplex sequencing platform, Oxford nanopore, and NuGEN Encore 384 multiplex platform.

In an embodiment of the invention, Roche 454 sequencing platform is used to sequence the bisulfite-treated target loci. When Roche 454 sequencing platform is used, the adapter sequences used in the PCR amplification primers comprise a barcode. A barcode is a sequence of about 4 to about 10 nucleotides that are used to distinguish between different samples during sequence analysis.

In a further aspect of the invention, the sequence data obtained from the multiplex sequencing platform is used to determine the methylation state and chromatin structure of the target loci. This can involve comparing sequence information obtained from several different samples and treatment options, for example, sequence obtained with or without DNA methyltransferase treatment, sequence obtained with or without bisulfite treatment, and known sequence of the target loci.

Integrating two potential methylation states with two potential chromatin accessibility states yields four potential combinations: 1) unmethylated and inaccessible; 2) unmethylated and accessible; 3) methylated and inaccessible; and 4) methylated and accessible.

The method of the current invention has varied applications and a person of ordinary skill in the art can design embodiments to use the method for different purposes. Examples of the embodiments that can use MAPit-patch method are discussed below.

In an embodiment of the invention, MAPit-patch is used to determine the differences in the chromatin structure and methylation state of the target loci between a first group of cells and a second group of cells by:
  a. determining methylation state and chromatin structure of the target loci in the first group of cells by treating the first group of cells according to MAPit-patch method,
  b. determining methylation state and chromatin structure of the target loci in the second group of cells by treating the second group of cells according to MAPit-patch method, and
  c. comparing the methylation state and chromatin obtained in steps a and b to determine the differences in the chromatin structure and methylation state of the target loci between the first group of cells and the second group of cells.

This embodiment of the invention can be used to identify target loci associated with a disease, for example, cancer. Determining the target loci associated with a disease in an individual provides information which can be used in individualized medicine. For example, knowing specific genes that are expressed abnormally in a subject can be used to design therapies directed to those genes.

In another embodiment of the invention MAPit-patch is used to determine endogenous methylation state and chromatin structure of target loci in a group of cells of a subject suspected of having a disease by:
  a. determining methylation state and chromatin structure of the target loci in cells obtained from a subject by treating the cells according to MAPit-patch method,
  b. determining methylation state and chromatin structure of the same target loci in a group of cells obtained from a control/normal (a disease free) subject by treating the cells according to MAPit-patch method,
  c. comparing the methylation state and chromatin structure of the same target loci of the subject to the methylation state and chromatin structure of the control/normal subject.

This embodiment of the invention can be used to identify transcription state of the genes of interest in a group of cells, for example, in a tissue sample from a subject suffering from a disease. Depending on the function of the gene and transcription activity state identified by the method of the current invention, therapies can be designed to modify the transcription activity of the genes of interest to treat the disease. This aspect of the invention also provides applications in individualized medicine.

In a further embodiment of the invention, MAPit-patch method is used to identify genes associated with a disease by:
  a. determining the methylation state and chromatin structure of the promoters of a set of genes and/or other loci in normal cells by treating the normal cells according to MAPit-patch method,
  b. determining methylation state and chromatin structure of the promoters of the set of genes and/or other loci in cells suffering from the disease by treating the cells suffering from the disease according to MAPit-patch method, and
  c. comparing the methylation state and chromatin structure of promoters of the genes and/or other loci in the normal cells and the cells suffering from the disease to identify genes associated with the disease.

This embodiment of the invention can be used to identify genes associated with a disease which can be used as drug targets to develop new therapies. This embodiment is also applicable in individualized medicine.

In a further embodiment of the invention, MAPit-patch method is used to identify the presence of abnormal cells or cells that can initiate a disease or prevent treatment of a disease by determining the methylation state and chromatin structure of the target loci known to be associated with a disease by:

a. determining the methylation state and chromatin structure of the promoters of a set of genes and/or other loci in a group of disease cells by treating the disease cells according to MAPit-patch method, b. determining methylation state and chromatin structure of the promoters of the set of genes and/or other loci in a group of cells that has been enriched for a disease phenotype, for example: drug-tolerant and/or cancerous cells, by treating the disease-phenotype enriched (for example, drug-tolerant and/or cancerous) cells according to MAPit-patch method, and c. comparing the methylation state and chromatin structure of promoters of the genes and/or other loci in the group of disease cells (a) and the cells enriched for drug tolerance and/or tumorigenicity (b) to identify epigenetic signatures associated with the phenotype of drug tolerance or tumor initiation.

This embodiment can be used to diagnose a disease, for example, detect presence of cancerous cells in a tissue sample from a subject or detect presence of drug-tolerant cells within a tumors sample from a subject. Due to high sensitivity offered by the MAPit-method, it can detect the presence of a small number of cancerous cells in a tissue sample, thereby aiding early detection of cancer which greatly increases treatment options and prognosis of cancer.

In another aspect of the invention, DNA methyltransferases (such as N4-C methyltransferases, C5-C methyltransferases, N6-A methyltransferases, etc.) can be used to probe chromatin structure in live cells. Delivery of DNA methyltransferases into the cell may be required if a purified enzyme is not available for probing chromatin structure in nuclei. The DNA methyltransferase gene product may be delivered using any standard method for delivery of transgenes to live cells, including but not limited to lipid-complex transfection, electroporation, liposomes, targeting using peptides or antibodies that cause internalization into a cell, particle bombardment, and viral particle transduction. Delivery of the DNA methyltransferase(s) to live cells may also be preferable to probing chromatin structure in nuclei. Probing chromatin in nuclei offers a "snapshot" of chromatin structure that is relatively static compared with that in live cells. By contrast, delivery of the DNA methyltransferase to live cells offers a more dynamic view of chromatin structure. Thus one can visualize for the first time at high resolution the extent to which a particular genomic region is accessible or occupied for the duration of enzyme expression in a live mammalian cell.

Materials and Methods

Cell Culture

NSC and GBM spheroid cultures were derived and maintained as described in (Deleyrolle et al. 2009). HCT116 colon cancer cells (a generous gift from Dr. Bert Vogelstein) were maintained in McCoy's 5A modified growth medium (Gibco) supplemented with 10% FBS and 1 unit/ml penicillin plus 1 µg/ml streptomycin. All cells were maintained in a humidified 37° C. incubator with 5% $CO_2$.

MAPit

Nuclei were prepared and probed with 0-100 units of M.CviPI (New England Biolabs) as indicated. Reactions were carried out, quenched and genomic DNA extracted as previously described (Pardo et al. 2011). For single-locus experiments, genomic DNA was deaminated and amplified in triplicate using HotStar Taq reagents (Qiagen). Triplicates were pooled, gel purified and TA-cloned using T-easy vector and reagents (Promega). Individual clones were sequenced and analyzed as previously described (Pardo et al. 2011). For MAPit-patch experiments, genomic DNA was processed under bisulfite patch PCR protocols.

MAPit in Live Cells

HCT116 cells were transfected with vector pLenti CMV/TO GFP-Zeo (Addgene plasmid 17431) using Lipofectamine LTX according to manufacturer protocol (Invitrogen). Cells were trypsinized 24 hrs post-transfection and subjected to fluorescence-activated cell sorting to collect cells expressing GFP, and by extension, M.CviPI. Genomic DNA was extracted, processed, sequenced, and data analyzed according to the MAPit-patch protocol.

MAPit-Patch

DNA was processed as previously described with the following modifications. 500 ng of genomic DNA was digested in a 20 µl reaction with 10 U AluBI and manufacturer provided buffer and bovine serum albumin (BSA). Reactions were incubated at 37° C. for 2 hrs then heat inactivated for 20 min at 65° C. The patch oligonucleotide hybridization and ligation reaction was carried out as described (Varley and Mitra 2010) except that the 3' U-1 oligonucleotide that contains a 3-carbon spacer was also synthesized with 5 phosphorothioate bonds to further protect target loci from exonuclease digestion. Reactions were then treated with exonucleases and bisulfite-converted as described. Amplification of target loci was carried out in 50 µl reactions with the following components: 10 µl of bisulfite-converted DNA, 1× HotStar Taq buffer (Qiagen), 500 µM $MgCl_2$, 50 µM each dNTP, 250 nM each barcoded primer and 10 U HotStar Taq DNA polymerase (Qiagen). Successful amplification of multiple products was confirmed by visualizing 15 µl of the reaction on a 2.5% agarose gel stained with ethidium bromide. A smear of products between 200-900 bp is observed. Remaining reaction products are pooled and PCR purified. Initially, we observed substantial primer dimer products upon sequencing analysis. This was improved by adding a gel purification step following PCR purification. Purified products were sequenced at the University of Florida Interdisciplinary Center for Biotechnology Research using the Roche 454 GS-FLX Plus according to manufacturer protocols.

Sequencing Data Analysis

Basic data processing was with custom Python code. First, sequences were divided by barcode, using Fastools (genome.ufl.edu/rivalab/fastools/). Next, sequences were aligned to the MAPit-patch reference library by BLAST. To prevent bias from enhanced recovery of methylated or non-deaminated sequences, both read and reference sequences were fully deaminated in silico before alignment. After restoration of cytosine information, sequences were scored for percent deamination of HCH, i.e., cytosines neither CG nor GC. Sequences with less than 95% conversion of HCH to HTH were discarded. The remaining sequences were then scored for percent methylation. MAPit-patch images were produced using MethylMapper (genome.ufl.edu/methyl/, Darst et al. 2012). All GCG sites were removed from analysis. Genome-wide, GCGs represent only 5.6% of all GC dinucleotides and removal of these sites does not strongly affect chromatin accessibility information (Kelly, Liu et al. 2012).

For methylation quantification, only promoters that obtained ≥10 reads were analyzed. CG methylation data are expressed as fraction methylated and calculated as the total number of methylated CGs divided by the total number of CGs for each amplicon. For GC accessibility quantification, two parameters were counted: 1) the number of reads per locus that exhibited ≥126 bp of unmethylated GC sites (i.e., consistent with nucleosome occupancy) divided by the total number of reads and subtracted from 1; and 2) the number of reads per locus that contain a nucleosome-depleted region (≥3 consecutive methylated GC sites) divided by the total number of reads. The average of these two values gives the fraction GC accessibility, reflecting the fraction of molecules that are nucleosome-depleted and highly accessible at each locus. CG methylation and GC accessibility values for each sample and locus are reported Tables 1 and 2 and MAPit-patch images for each locus are shown in FIG. 14, separated according to their accessibility classification. Parameters for classifying promoters according to CG methylation and/or GC accessibility are reported in the results section.

TABLE 1

Methylation state and chromatin structure of target loci from GBM L0 cells.

| GBM L0 Gene | reads | #_nuc occupied[a] | 1-fraction nuc occ[b] | #3_consecutive_G-m$^5$C[c] | fraction_3_consecutive G-m$^5$C[d] | GC score[e] | Chromatin class[f] | fraction CG methylation | Methylation Class[g] |
|---|---|---|---|---|---|---|---|---|---|
| RNF219 (C13orf7) | 29 | 28 | 0.03 | 0 | 0.00 | 0.02 | I | 0.01 | U |
| VEPH1 | 67 | 65 | 0.03 | 1 | 0.01 | 0.02 | I | 0.84 | M |
| TNN | 316 | 300 | 0.05 | 3 | 0.01 | 0.03 | I | 0.79 | V |
| NKX2-5 | 81 | 75 | 0.07 | 0 | 0.00 | 0.04 | I | 0.79 | V |
| IGFBP3 | 54 | 51 | 0.06 | 2 | 0.04 | 0.05 | I | 0.95 | M |
| XDH | 20 | 19 | 0.05 | 1 | 0.05 | 0.05 | I | 0.70 | V |
| EXOC4 (SEC8L1) | 35 | 32 | 0.09 | 2 | 0.06 | 0.07 | I | 0.38 | V |
| ACSL5 | 102 | 94 | 0.08 | 7 | 0.07 | 0.07 | I | 0.51 | V |
| PCDHA9 | 176 | 147 | 0.16 | 4 | 0.02 | 0.09 | I | 0.87 | M |
| MGMT | 21 | 20 | 0.05 | 3 | 0.14 | 0.10 | I | 0.57 | V |
| RASSF1 | 43 | 39 | 0.09 | 5 | 0.12 | 0.10 | I | 0.74 | V |
| AGAP2 (CENTG1) | 314 | 263 | 0.16 | 18 | 0.06 | 0.11 | I | 0.53 | V |
| SORL1 | 219 | 191 | 0.13 | 21 | 0.10 | 0.11 | I | 0.96 | M |
| SLC9C1 (SLC9A10) | 180 | 154 | 0.14 | 15 | 0.08 | 0.11 | I | 0.75 | V |
| SOX10 | 127 | 112 | 0.12 | 14 | 0.11 | 0.11 | I | 0.97 | M |
| AOC1 (ABP1) | 35 | 28 | 0.20 | 1 | 0.03 | 0.11 | I | 0.64 | V |
| COL19A1 | 216 | 175 | 0.19 | 11 | 0.05 | 0.12 | I | 0.30 | V |
| DSCAML1 | 172 | 137 | 0.20 | 10 | 0.06 | 0.13 | I | 0.88 | M |
| MYLK4 (LOC340156) | 178 | 126 | 0.29 | 3 | 0.02 | 0.15 | I | 0.98 | M |
| HIST1H1B | 99 | 83 | 0.16 | 16 | 0.16 | 0.16 | I | 0.39 | V |
| XIRP1 (CMYA1) | 30 | 22 | 0.27 | 2 | 0.07 | 0.17 | I | 0.60 | V |
| DBN1 | 216 | 166 | 0.23 | 27 | 0.13 | 0.18 | I | 0.80 | M |
| KCNQ5 | 22 | 17 | 0.23 | 3 | 0.14 | 0.18 | I | 0.16 | U |
| RP1L1 | 30 | 27 | 0.10 | 8 | 0.27 | 0.18 | I | 0.93 | M |
| FAM171B (KIAA1946) | 136 | 104 | 0.24 | 23 | 0.17 | 0.20 | MI | 0.09 | U |
| RARB | 74 | 59 | 0.20 | 15 | 0.20 | 0.20 | MI | 0.44 | V |
| PDCD11 | 50 | 37 | 0.26 | 8 | 0.16 | 0.21 | MI | 0.01 | U |
| CD93 (C1QR1) | 105 | 76 | 0.28 | 19 | 0.18 | 0.23 | MI | 0.03 | U |
| PRPF4B | 81 | 54 | 0.33 | 11 | 0.14 | 0.23 | MI | 0.01 | U |
| DPYD | 188 | 142 | 0.24 | 48 | 0.26 | 0.25 | MI | 0.02 | U |
| MAMDC4 (AEGP) | 73 | 50 | 0.32 | 14 | 0.19 | 0.25 | MI | 0.88 | M |
| LRRFIP1 | 35 | 22 | 0.37 | 6 | 0.17 | 0.27 | MI | 0.43 | V |
| CLEC4C | 226 | 132 | 0.42 | 40 | 0.18 | 0.30 | MI | 0.13 | U |
| UHRF2 | 70 | 47 | 0.33 | 19 | 0.27 | 0.30 | MI | 0.13 | U |
| CYP1A1 | 39 | 29 | 0.26 | 17 | 0.44 | 0.35 | MI | 0.01 | U |
| ZNF646 | 166 | 113 | 0.32 | 62 | 0.37 | 0.35 | MI | 0.00 | U |
| PPM1E | 194 | 98 | 0.49 | 39 | 0.20 | 0.35 | MI | 0.02 | U |
| SIK3 (KIAA0999) | 47 | 29 | 0.38 | 15 | 0.32 | 0.35 | MI | 0.01 | U |
| CDH1 | 40 | 23 | 0.43 | 13 | 0.33 | 0.38 | MI | 0.52 | V |
| FBXW7 | 48 | 28 | 0.42 | 18 | 0.38 | 0.40 | H | 0.02 | U |
| H19 | 80 | 42 | 0.48 | 26 | 0.33 | 0.40 | H | 0.36 | V |
| EPHB6 | 221 | 118 | 0.47 | 79 | 0.36 | 0.41 | H | 0.03 | U |
| UQCRC2 | 49 | 21 | 0.57 | 13 | 0.27 | 0.42 | H | reported | U |
| SULF2 | 175 | 113 | 0.35 | 90 | 0.51 | 0.43 | H | 0.01 | U |
| DTNB | 130 | 69 | 0.47 | 53 | 0.41 | 0.44 | H | 0.05 | U |
| CTIF (KIAA0427) | 43 | 26 | 0.40 | 22 | 0.51 | 0.45 | H | 0.02 | U |
| EGFR | 43 | 31 | 0.28 | 28 | 0.65 | 0.47 | H | 0.03 | U |
| JKAMP (C14orf100) | 33 | 20 | 0.39 | 21 | 0.64 | 0.52 | H | 0.01 | U |
| CLCN3 | 185 | 74 | 0.60 | 85 | 0.46 | 0.53 | H | 0.01 | U |
| PLEKHA8 | 22 | 12 | 0.45 | 14 | 0.64 | 0.55 | H | 0.02 | U |
| BCL9 | 22 | 7 | 0.68 | 9 | 0.41 | 0.55 | H | 0.00 | U |
| ICAM5 | 185 | 76 | 0.59 | 94 | 0.51 | 0.55 | H | 0.05 | U |
| TP53 | 87 | 6 | 0.93 | 17 | 0.20 | 0.56 | H | 0.01 | U |
| SFRS6 | 21 | 12 | 0.43 | 15 | 0.71 | 0.57 | H | 0.01 | U |
| DPAGT1 | 38 | 5 | 0.87 | 15 | 0.39 | 0.63 | MA | 0.01 | U |
| PIK3CA | 37 | 16 | 0.57 | 27 | 0.73 | 0.65 | MA | 0.01 | U |
| EPM2AIP1 | 30 | 13 | 0.57 | 26 | 0.87 | 0.72 | MA | 0.02 | U |
| TAF1 | 126 | 20 | 0.84 | 76 | 0.60 | 0.72 | MA | 0.01 | U |
| GALNS | 71 | 21 | 0.70 | 53 | 0.75 | 0.73 | MA | 0.02 | U |
| TIAM1 | 20 | 8 | 0.60 | 19 | 0.95 | 0.78 | MA | 0.02 | U |

TABLE 1-continued

Methylation state and chromatin structure of target loci from GBM L0 cells.

| GBM L0 Gene | reads | #_nuc occupied[a] | 1-fraction nuc occ[b] | #3_consecutive_G-m$^5$C[c] | fraction_3_consecutive G-m$^5$C[d] | GC score[e] | Chromatin class[f] | fraction CG methylation | Methylation Class[g] |
|---|---|---|---|---|---|---|---|---|---|
| PRUNE2 (KIAA0367) | 30 | 7 | 0.77 | 25 | 0.83 | 0.80 | MA | 0.02 | U |
| NF1 | 65 | 7 | 0.89 | 47 | 0.72 | 0.81 | A | 0.02 | U |
| NUP214 | 135 | 24 | 0.82 | 111 | 0.82 | 0.82 | A | 0.02 | U |
| SMAD4 | 49 | 6 | 0.88 | 44 | 0.90 | 0.89 | A | 0.02 | U |
| ABCB8 | 143 | 3 | 0.98 | 126 | 0.88 | 0.93 | A | 0.01 | U |
| ERCC6 | 83 | 5 | 0.94 | 77 | 0.93 | 0.93 | A | 0.02 | U |
| SH3TC1 | 186 | 10 | 0.95 | 172 | 0.92 | 0.94 | A | 0.04 | U |
| ITGAE | 19 | 19 | 0.00 | 1 | 0.05 | 0.03 | N/A | 0.93 | M |
| GUCY1A2 | 10 | 8 | 0.20 | 0 | 0.00 | 0.10 | N/A | 0.05 | U |
| FHIT | 13 | 12 | 0.08 | 2 | 0.15 | 0.12 | N/A | 0.11 | U |
| SLC8A3 | 12 | 11 | 0.08 | 2 | 0.17 | 0.13 | N/A | 0.02 | U |
| SCN3B | 11 | 11 | 0.00 | 3 | 0.27 | 0.14 | N/A | 0.16 | U |
| SZT2 (KIAA0467) | 13 | 12 | 0.08 | 4 | 0.31 | 0.19 | N/A | 0.97 | M |
| CSPP1 | 19 | 15 | 0.21 | 5 | 0.26 | 0.24 | N/A | 0.53 | V |
| TMEM123 | 13 | 11 | 0.15 | 5 | 0.38 | 0.27 | N/A | 0.12 | U |
| SEMA3B | 18 | 17 | 0.06 | 9 | 0.50 | 0.28 | N/A | 0.19 | U |
| GPR158 | 12 | 8 | 0.33 | 8 | 0.67 | 0.50 | N/A | 0.00 | U |
| MLH1 | 17 | 12 | 0.29 | 12 | 0.71 | 0.50 | N/A | 0.01 | U |
| KIAA0556 | 10 | 5 | 0.50 | 7 | 0.70 | 0.60 | N/A | 0.02 | U |
| ZMYM4 (ZNF262) | 16 | 7 | 0.56 | 12 | 0.75 | 0.66 | N/A | 0.04 | U |
| NOTCH1 | 12 | 4 | 0.67 | 8 | 0.67 | 0.67 | N/A | 0.03 | U |
| GSTP1 | 18 | 2 | 0.89 | 18 | 1.00 | 0.94 | N/A | 0.01 | U |

For GC quantification expressed as percent accessible molecules, only promoters that obtained ≥20 reads were analyzed. Two parameters were counted:

[a] the number of reads per locus that exhibited ≥126 bp of unmethylated GC sites (i.e. consistent with nucleosome (nuc) occupancy); and

[c] the number of reads per locus that contain ≥3 consecutive methylated GC sites (i.e. a nuc free region). These values are used to calculate the fraction of molecules accessible at each locus ([b] and [d]).

[e] The GC score is the average of these two values, reflecting the fraction of molecules that are nucleosome depleted and highly accessible at each locus.

[f] I, inaccessible; MI, mostly inaccessible; H, half inaccessible; MA, mostly accessible; A, accessible; N/A, not applicable, i.e. <20x sequencing coverage

[g] M, methylated; V, variably methylated; U, unmethylated

TABLE 2

Methylation state and chromatin structure of target loci from NSC cells.

| NSC Gene | reads | #_nuc occupied[a] | 1-fraction nuc occ[b] | #3_consecutive_G-m$^5$C[c] | fraction_3_consecutive G-m$^5$C[d] | GC score[e] | Chromatin class[f] | fraction CG methylation | Methylation Class[g] |
|---|---|---|---|---|---|---|---|---|---|
| TNN | 180 | 176 | 0.02 | 0 | 0.00 | 0.01 | I | 0.86 | M |
| RNF219 (C13orf7) | 23 | 22 | 0.04 | 0 | 0.00 | 0.02 | I | 0.01 | U |
| VEPH1 | 130 | 124 | 0.05 | 4 | 0.03 | 0.04 | I | 0.70 | V |
| RP1L1 | 24 | 24 | 0.00 | 2 | 0.08 | 0.04 | I | 0.92 | M |
| PCDHA9 | 195 | 173 | 0.11 | 0 | 0.00 | 0.06 | I | 0.32 | V |
| XIRP1 (CMYA1) | 59 | 54 | 0.08 | 2 | 0.03 | 0.06 | I | 0.87 | M |
| SLC9C1 (SLC9A10) | 202 | 185 | 0.08 | 8 | 0.04 | 0.06 | I | 0.91 | M |
| ACSL5 | 87 | 81 | 0.07 | 5 | 0.06 | 0.06 | I | 0.73 | V |
| DSCAML1 | 189 | 168 | 0.11 | 8 | 0.04 | 0.08 | I | 0.90 | M |
| AGAP2 (CENTG1) | 310 | 271 | 0.13 | 9 | 0.03 | 0.08 | I | 0.73 | V |
| NKX2-5 | 76 | 65 | 0.14 | 2 | 0.03 | 0.09 | I | 0.07 | U |
| SOX10 | 105 | 90 | 0.14 | 7 | 0.07 | 0.10 | I | 0.91 | M |
| SORL1 | 340 | 293 | 0.14 | 30 | 0.09 | 0.11 | I | 0.81 | M |
| COL19A1 | 281 | 221 | 0.21 | 7 | 0.02 | 0.12 | I | 0.47 | V |
| MYLK4 (LOC340156) | 186 | 142 | 0.24 | 1 | 0.01 | 0.12 | I | 0.95 | M |
| FAM171B (KIAA1946) | 75 | 62 | 0.17 | 7 | 0.09 | 0.13 | I | 0.12 | U |
| HIST1H1B | 104 | 90 | 0.13 | 15 | 0.14 | 0.14 | I | 0.38 | V |
| DBN1 | 211 | 155 | 0.27 | 18 | 0.09 | 0.18 | I | 0.59 | V |
| PRPF4B | 52 | 38 | 0.27 | 5 | 0.10 | 0.18 | I | 0.05 | U |
| CYP1A1 | 32 | 30 | 0.06 | 10 | 0.31 | 0.19 | I | 0.01 | U |
| RASSF1 | 39 | 27 | 0.31 | 5 | 0.13 | 0.22 | MI | 0.34 | V |
| H19 | 93 | 67 | 0.28 | 15 | 0.16 | 0.22 | MI | 0.50 | V |
| CD93 (C1QR1) | 68 | 46 | 0.32 | 13 | 0.19 | 0.26 | MI | 0.39 | V |
| SIK3 (KIAA0999) | 26 | 20 | 0.23 | 8 | 0.31 | 0.27 | MI | 0.04 | U |
| RARB | 101 | 75 | 0.26 | 30 | 0.30 | 0.28 | MI | 0.02 | U |
| PDCD11 | 45 | 32 | 0.29 | 12 | 0.27 | 0.28 | MI | 0.01 | U |
| MAMDC4 (AEGP) | 55 | 36 | 0.35 | 14 | 0.25 | 0.30 | MI | 0.93 | M |
| CLEC4C | 378 | 209 | 0.45 | 78 | 0.21 | 0.33 | MI | 0.09 | U |
| CTIF (KIAA0427) | 50 | 40 | 0.20 | 23 | 0.46 | 0.33 | MI | 0.03 | U |
| UHRF2 | 62 | 38 | 0.39 | 17 | 0.27 | 0.33 | MI | 0.10 | U |
| PPM1E | 158 | 80 | 0.49 | 31 | 0.20 | 0.34 | MI | 0.01 | U |
| LRRFIP1 | 34 | 17 | 0.50 | 8 | 0.24 | 0.37 | MI | 0.03 | U |
| FBXW7 | 51 | 31 | 0.39 | 20 | 0.39 | 0.39 | MI | 0.01 | U |

TABLE 2-continued

Methylation state and chromatin structure of target loci from NSC cells.

| NSC Gene | reads | #_nuc occupied[a] | 1-fraction nuc occ[b] | #3_con-secutive_G-m$^5$C[c] | fraction_3_con-secutive G-m$^5$C[d] | GC score[e] | Chromatin class[f] | fraction CG methylation | Methylation Class[g] |
|---|---|---|---|---|---|---|---|---|---|
| ICAM5 | 142 | 81 | 0.43 | 52 | 0.37 | 0.40 | H | 0.01 | U |
| UQCRC2 | 26 | 12 | 0.54 | 7 | 0.27 | 0.40 | H | 0.00 | U |
| ZNF646 | 180 | 115 | 0.36 | 83 | 0.46 | 0.41 | H | 0.01 | U |
| CDH1 | 45 | 26 | 0.42 | 22 | 0.49 | 0.46 | H | 0.05 | U |
| TAF1 | 190 | 90 | 0.53 | 77 | 0.41 | 0.47 | H | 0.29 | V |
| DTNB | 124 | 64 | 0.48 | 56 | 0.45 | 0.47 | H | 0.05 | U |
| DPYD | 111 | 54 | 0.51 | 48 | 0.43 | 0.47 | H | 0.01 | U |
| TP53 | 142 | 27 | 0.81 | 20 | 0.14 | 0.48 | H | 0.01 | U |
| SULF2 | 105 | 56 | 0.47 | 57 | 0.54 | 0.50 | H | 0.01 | U |
| EPHB6 | 146 | 67 | 0.54 | 69 | 0.47 | 0.51 | H | 0.01 | U |
| JKAMP (C14orf100) | 30 | 18 | 0.40 | 20 | 0.67 | 0.53 | H | 0.02 | U |
| CLCN3 | 213 | 76 | 0.64 | 110 | 0.52 | 0.58 | H | 0.00 | U |
| PRUNE2 (KIAA0367) | 24 | 7 | 0.71 | 14 | 0.58 | 0.65 | MA | 0.01 | U |
| SH3TC1 | 216 | 36 | 0.83 | 157 | 0.73 | 0.78 | MA | 0.09 | U |
| GALNS | 88 | 21 | 0.76 | 73 | 0.83 | 0.80 | MA | 0.02 | U |
| NF1 | 63 | 10 | 0.84 | 50 | 0.79 | 0.82 | A | 0.02 | U |
| NUP214 | 166 | 31 | 0.81 | 139 | 0.84 | 0.83 | A | 0.01 | U |
| ABCB8 | 139 | 7 | 0.95 | 105 | 0.76 | 0.85 | A | 0.01 | U |
| PIK3CA | 44 | 5 | 0.89 | 39 | 0.89 | 0.89 | A | 0.01 | U |
| SMAD4 | 49 | 3 | 0.94 | 47 | 0.96 | 0.95 | A | 0.02 | U |
| ERCC6 | 73 | 3 | 0.96 | 69 | 0.95 | 0.95 | A | 0.04 | U |
| ITGAE | 11 | 11 | 0.00 | 1 | 0.09 | 0.05 | N/A | 0.97 | M |
| FHIT | 18 | 18 | 0.00 | 2 | 0.11 | 0.06 | N/A | 0.13 | U |
| AOC1 (ABP1) | 16 | 15 | 0.06 | 1 | 0.06 | 0.06 | N/A | 0.75 | V |
| KCNQ5 | 16 | 15 | 0.06 | 1 | 0.06 | 0.06 | N/A | 0.02 | U |
| CSPP1 | 19 | 18 | 0.05 | 3 | 0.16 | 0.11 | N/A | 0.61 | V |
| XDH | 15 | 13 | 0.13 | 2 | 0.13 | 0.13 | N/A | 0.60 | V |
| IGFBP3 | 14 | 12 | 0.14 | 3 | 0.21 | 0.18 | N/A | 0.03 | U |
| BCL9 | 12 | 8 | 0.33 | 2 | 0.17 | 0.25 | N/A | 0.00 | U |
| DPAGT1 | 15 | 6 | 0.60 | 2 | 0.13 | 0.37 | N/A | 0.03 | U |
| SLC8A3 | 12 | 10 | 0.17 | 8 | 0.67 | 0.42 | N/A | 0.00 | U |
| LAMA1 | 18 | 5 | 0.72 | 7 | 0.39 | 0.56 | N/A | 0.07 | U |
| GEN1 (FLJ40869) | 12 | 5 | 0.58 | 9 | 0.75 | 0.67 | N/A | 0.02 | U |
| EPM2AIP1 | 12 | 6 | 0.50 | 10 | 0.83 | 0.67 | N/A | 0.01 | U |
| TIAM1 | 16 | 6 | 0.63 | 13 | 0.81 | 0.72 | N/A | 0.03 | U |
| GPR158 | 13 | 6 | 0.54 | 13 | 1.00 | 0.77 | N/A | 0.03 | U |
| PLEKHA8 | 14 | 5 | 0.64 | 13 | 0.93 | 0.79 | N/A | 0.03 | U |
| ZMYM4 (ZNF262) | 12 | 5 | 0.58 | 12 | 1.00 | 0.79 | N/A | 0.04 | U |
| SFRS6 | 17 | 5 | 0.71 | 15 | 0.88 | 0.79 | N/A | 0.02 | U |
| GSTP1 | 19 | 1 | 0.95 | 19 | 1.00 | 0.97 | N/A | 0.02 | U |

For GC quantification expressed as percent accessible molecules, only promoters that obtained ≥20 reads were analyzed. Two parameters were counted:
[a]the number of reads per locus that exhibited ≥126 bp of unmethylated GC sites (i.e. consistent with nucleosome (nuc) occupancy); and
[c]the number of reads per locus that contain ≥3 consecutive methylated GC sites (i.e. a nuc free region). These values are used to calculate the fraction of molecules accessible at each locus ([b] and [d]).
[e]The GC score is the average of these two values, reflecting the fraction of molecules that are nucleosome depleted and highly accessible at each locus.
[f]I, inaccessible; MI, mostly inaccessible; H, half inaccessible; MA, mostly accessible; A, accessible; N/A, not applicable, i.e. <20x sequencing coverage
[g]M, methylated; V, variably methylated; U, unmethylated Immunostaining and Flow Cytometry Cells were seeded in spheroid culture conditions, grown for four days then treated with the indicated doses of temozolomide. Three days after drug treatment, cells were harvested for downstream immunolabeling using antibody against Mlh1 (1/500, Santa Cruz). Staining was quantified by flow cytometry (BD LSRII).

Statistical Analysis

All statistical analyses were performed using GraphPad Prism software. Pearson's correlation was used to determine statistical correlations and coefficients between samples and between amplicon length and abundance. For reproducibility measures, reads per locus for each sample were plotted in a correlation matrix for pairwise comparisons as previously described. Comparisons between groups were tested using two-way ANOVA followed by Bonferroni ad hoc test. Significance values for differentially regulated promoters, allele-restricted signatures and enrichment for methylation states were obtained using two-sided Fisher's exact test.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

MAPit-Patch to Determine Epigenetic Heterogeneity

MAPit-patch was used to determine the extent to which epigenetic heterogeneity exists in human GBM. Starting with 500 ng of input genomic DNA, we have concurrently profiled DNA methylation and chromatin accessibility at 71 promoters from a panel of genes with cancer-associated functions and identified several different classes of epigenetic heterogeneity in human GBM and control neural stem cells (NSCs). Additionally, 29 differentially methylated and/or differentially accessible promoters were discovered. Gene expression was measured for a subset of these 29 differentially regulated promoters and found to correlate with the epigenetic features identified. Finally, we tested the relevance of epigenetic subpopulations to GBM phenotypic heterogeneity. Strikingly, a subpopulation of cells exhibiting inaccessible chromatin at the MLH1 promoter was negative for Mlh1 immunostaining and enriched in drug-tolerant GBM cells. Epigenetic heterogeneity is therefore a common feature within a given GBM or NSC cell line and may contribute to diverse cellular phenotypes, including drug tolerance. MAPit-patch is a robust method that can query multiple targeted genetic loci with extensive coverage and detect epigenetic variability within heterogeneous cellular populations using low input amounts of DNA.

EXAMPLE 2

MAPit-Patch: A Cost-Effective, Multiplexed, Targeted Method for Simultaneous Mapping of Chromatin Accessibility and DNA Methylation on Single Molecules To obtain combined DNA methylation and chromatin accessibility data on individual DNA strands or molecules, nuclei are probed with M.CviPI, which methylates cytosine in accessible GC dinucleotides. GC sites within nucleosomes or those occluded by DNA-bound non-histone proteins are inaccessible to M.CviPI activity and remain unmethylated. For MAPit-BGS (FIG. 1A), genomic DNA is then bisulfite converted to discriminate between methylated (accessible) or unmethylated (inaccessible) GCs and, concomitantly, between endogenously methylated or unmethylated CGs (GCGs are removed from analysis). Bisulfite-treated genomic DNA is then amplified using locus-specific primers and reaction products are purified and cloned. Sanger sequences from individually cloned molecules are aligned and analyzed to map the methylation status of all CG and GC sites at single-nucleotide resolution. Spans of methylated and unmethylated GC sites indicate accessible regions and protein-DNA footprints, respectively, present in the isolated nuclei. For studies requiring interrogation of multiple targets with greater than 10x coverage, MAPit-BGS would be laborious as well as material-prohibitive and cost-prohibitive.

Bisulfite patch PCR is a robust method for targeted next-generation bisulfite sequencing (FIG. 1B) (Varley and Mitra 2010). Briefly, purified genomic DNA is first digested by a restriction enzyme with a frequently occurring recognition sequence into fragments with defined sizes and ends. After denaturation, in a multiplexed reaction, both defined single-stranded ends of selected target loci are hybridized and ligated to specific patch oligonucleotides (patch-1 and patch-2) and oligonucleotides with universal priming sequences (U-1 and U-2), respectively. The U-1 and U-2 oligonucleotides are C-less to resist bisulfite conversion; U-2 also contains a 5' phosphate to enable ligation and a 3-carbon addition to its 3' hydroxyl and incorporated phosphorothioates at its 3' end, which protects the targeted fragment against digestion with 3' exonucleases used to enrich for the fragments of interest for bisulfite conversion. PCR is performed using the universal primers with platform-specific adapter sequences and optionally barcodes at their 5' ends. Amplified products are then purified and sequenced using the appropriate platform.

The original bisulfite patch PCR study used the restriction enzyme AluI (recognizes AGCT) for fragmentation of genomic DNA and targeted 94 loci in a single reaction. AluI creates blunt ends and is well-suited for patch selection as it occurs frequently in CG islands, which are present in 70% of mammalian promoters. However, as digestion by AluI is blocked by C5 methylation, its use is not compatible with M.CviPI-modified DNA. The isoschizomer AluBI also produces blunt ends at AGCT sites, but is not affected by C5 methylation (Sibenzyme.com and FIG. 10). Thus, AluBI can accommodate genomic DNA isolated from M.CviPI-probed chromatin in the bisulfite patch PCR protocol, a method hereafter referred to as MAPit-patch.

Integrating two potential methylation states with two potential chromatin accessibility states yields four potential combinations: 1) unmethylated and inaccessible; 2) unmethylated and accessible; 3) methylated and inaccessible; and 4) methylated and accessible. It should be noted that state 4 is seldom observed. Furthermore, we and others have observed that promoters classified as state 1 are repressed, state 2 are expressed and/or poised for expression (i.e., initiated and paused RNA polymerase II), and state 3 are epigenetically silenced (Kelly et al., 2012).

Figure 2:
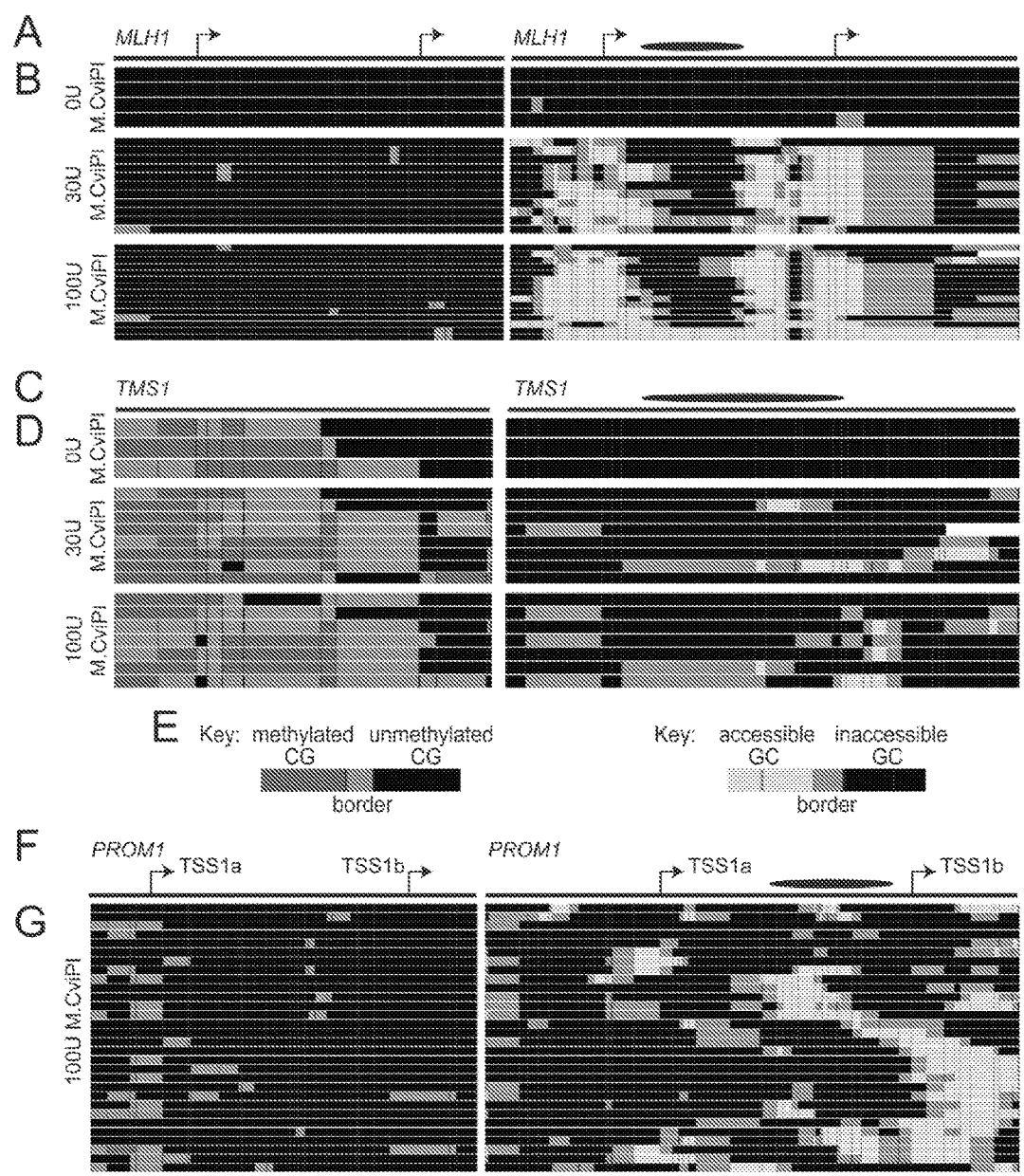

To identify probing conditions that would allow for detection of differing chromatin states, nuclei from NSCs were probed with 0, 30 and 100 U M.CviPI and analyzed by MAPit-BGS (FIG. 2). NSCs were harvested from serum-free, suspension culture (hereafter, spheroid culture), which maintains these cells in an undifferentiated state and preserves their phenotypic heterogeneity (Deleyrolle and Reynolds 2009). To facilitate pattern recognition, aligned sequences are uploaded into a web-based hierarchical clustering program called MethylMapper (genome.ufl.edu/methyl). MethylMapper generates 3-color images of clustered CG methylation (FIG. 2B,D left panels) or GC accessibility (FIG. 2B,D right panels, and G). Each row represents one sequenced molecule. Two or more consecutively methylated CG and GC sites are connected by red and yellow, respectively, whereas two or more consecutively unmethylated sites are connected by black (see keys in FIG. 2E). Note that CG and GC information are clustered end-to-end, so the presentation order of the molecules is linked in the left and right panels of FIGS. 2B and D.

MAPit-BGS of the proximal promoter of MLH1, an expressed gene encoding a mismatch repair protein, shows that this region is unmethylated and highly accessible (state 2) around the two TSSs (FIG. 2A,B). The protected region (i.e., inaccessible to M.CviPI) between the two accessible regions is consistent with the size of a nucleosome core particle (147 bp). Conversely, analysis of the TMS1 promoter, driving a silent gene that encodes a protein involved in apoptosis, shows that this region is methylated and largely inaccessible (state 3) (FIG. 2C,D). Since both 30 U and 100 U showed equivalent and saturated levels of probing at both the MLH1 and TMS1 promoters, we opted to use 100 U in all further reactions. To determine if epigenetic heterogeneity is also observed in these cultures, we amplified the promoter of PROM1 (FIG. 2F,G), which encodes the cell surface antigen CD133, expressed in up to 40% of cells in a given NSC culture (Piao et al. 2006; Sun et al. 2009. All analyzed PROM1 promoter sequences were largely unmethylated (FIG. 2G, left panel); however, substantial heterogeneity in chromatin accessibility was observed across the locus, especially at TSS1b where transcription is initiated in neural tissue (Shmelkov et al. 2004) (FIG. 2F,G). Approximately 50% of the promoters in the NSC population exhibit substantial accessibility around TSS1b (state 2) indicating nucleosome depletion, whereas the remaining half are unmethylated but inaccessible (state 1) and exhibit a nucleosome-sized footprint spanning across TSS1b. In conclusion, probing with 100 U M.CviPI enables interrogation of diverse, heterogeneous chromatin states in spheroid cultured cells.

Figure 3:
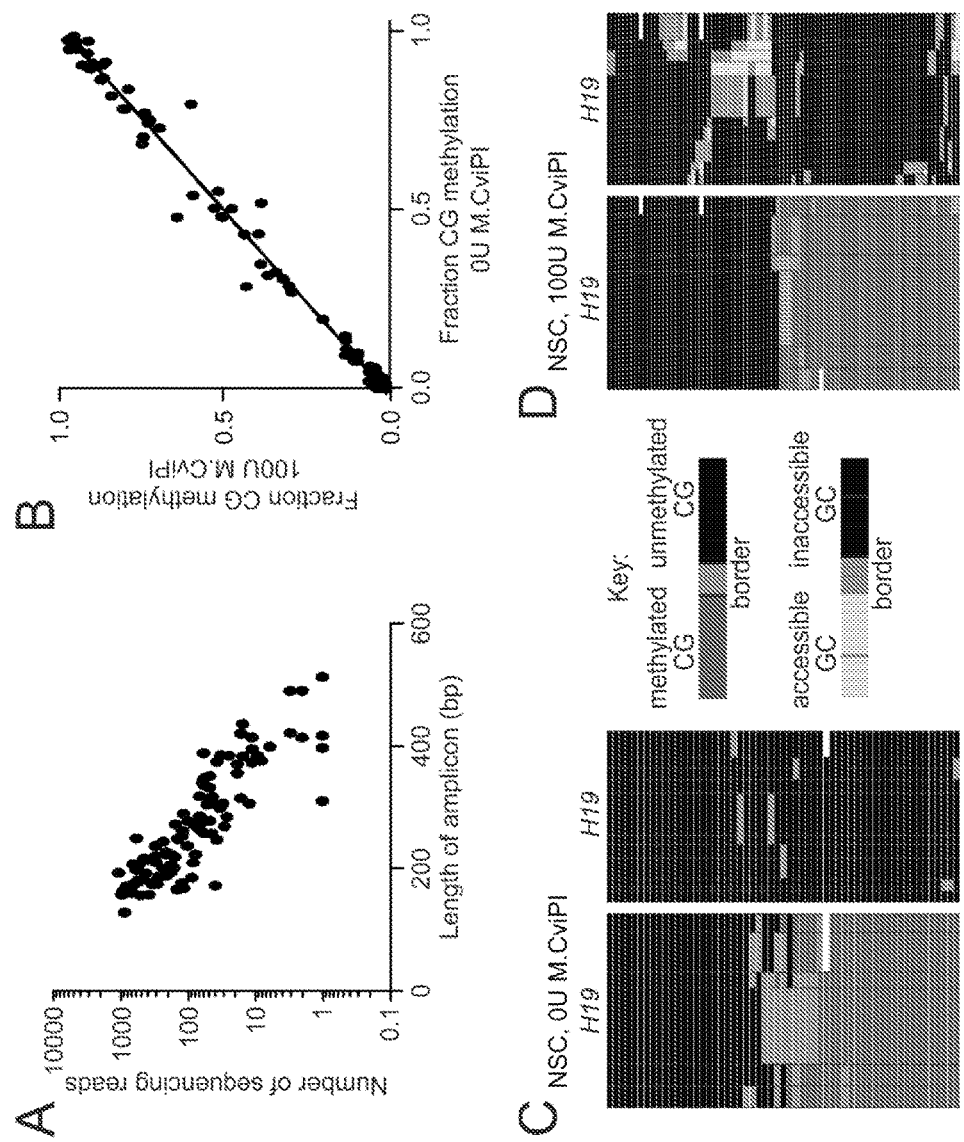

We sought to confirm that M.CviPI probing of chromatin structure and hence GC methylation would not affect the coverage and reproducibility results obtained by the original bisulfite patch PCR protocol. Target sequence enrichment was therefore performed using the published patch oligonucleotide library. This library targets promoters within 700 bp of the TSS of 90 genes that are commonly mutated in breast and/or colon cancer ("CAN genes"). Four control loci are also included and we added 19 additional cancer-associated loci targeted within 600 bp of the TSS. Bisulfite patch PCR was performed using 500 ng of DNA from NSC and GBM L0 spheroid cultures probed with 0 U or 100 U M.CviPI. Sample specific 5-bp barcodes were incorporated during the final amplification step, then all reactions were pooled, purified and sequenced using one-eighth of a plate on a 454 FLX Life Sciences sequencer. After removing sequences with bisulfite conversion efficiencies of <95% and sequencing reads <100 bp, we obtained 22,356 unique sequences that all aligned to 104 of the 113 targeted loci (92% of targets), indicating a high sensitivity of the technique. Mean coverage of each promoter was 215 reads (range of 1-1018 reads; median, 99 reads) and the sequencing depth of 87% of the targeted promoters was within 10-fold of the median. Consistent with published bisulfite patch PCR results, we observed a significant inverse correlation between amplicon length and read coverage with MAPit-patch (P<0.0001; Pearson's correlation) (FIG. 3A).

To determine if target loci were reproducibly amplified in MAPit-patch, the number of reads per locus was plotted for each individual sample and correlation coefficients between all pairs of samples were calculated. The mean correlation coefficient was 0.94, which is comparable to the value of 0.91 obtained by bisulfite patch PCR. As previously reported, these data indicate that the coverage of each promoter is not stochastic between samples, but is reproducible and strongly affected by amplicon length. Thus, chromatin probing with M.CviPI, presence of GC methylation, and AluBI substitution in the MAPit-patch protocol do not affect the performance of bisulfite patch PCR.

To determine if probing chromatin structure with M.CviPI would affect accurate quantification of CG methylation, the fraction of methylated CGs (excluding GCGs in all analyses) at each promoter was calculated and compared between the 0 U and 100 U samples. The fraction of CG methylation correlated significantly (P<0.0001) between M.CviPI-modified and unmodified samples, $R^2=0.99$ (FIG. 3B). To confirm that modification by M.CviPI did not alter the ability of bisulfite patch PCR to amplify methylated and unmethylated molecules with equal efficiency, we examined the DNA methylation profile of the imprinted locus H19 in NSCs. The 0 U and 100 U samples both showed indistinguishable levels of CG methylation (0 U=48%, 100 U=50%) and amplified methylated and unmethylated molecules with equivalent efficiencies (FIG. 3C,D, left panels). In conclusion, MAPit-patch does not introduce bias in quantification of CG methylation nor does it alter the ability of patch bisulfite PCR to equivalently amplify methylated and unmethylated molecules. In addition, MAPit-patch also accurately profiles the expected allele-specific inverse relationship between DNA methylation and chromatin accessibility at the imprinted H19 locus (P=0.0015) (FIG. 3D, right and left panels).

TABLE 3

Target loci and positions relative to the TSS

| Gene | Accession | Length (bp) | TSS from left (bp) | TSS from right (bp) | #HCG | #GCH | #GCG |
|---|---|---|---|---|---|---|---|
| ABCB8 | NM_007188 | 179 | −231 | −53 | 5 | 13 | 3 |
| AOC1 (ABP1) | NM_001091 | 207 | −506 | −300 | 4 | 12 | 1 |
| ACSL5 | NM_016234 | 235 | −588 | −354 | 3 | 11 | 2 |
| MAMDC4 (AEGP) | NM_206920 | 221 | −364 | −144 | 5 | 21 | 1 |
| BCL9 | NM_004326 | 256 | 550 | 295 | 3 | 16 | 2 |
| RNF219 (C13orf7) | NM_024546 | 269 | −446 | −178 | 8 | 6 | 2 |
| JKAMP (C14orf100) | NM_016475 | 287 | −377 | −91 | 28 | 30 | 6 |
| CD93 (C1QR1) | NM_012072 | 172 | −314 | −143 | 8 | 16 | 0 |
| CDH1 | NM_004360 | 187 | 32 | 218 | 15 | 23 | 5 |
| AGAP2 (CENTG1) | NM_014770 | 190 | −452 | −263 | 3 | 9 | 0 |
| CLCN3 | NM_001829 | 163 | −360 | −198 | 11 | 13 | 4 |
| CLEC4C | NM_130441 | 158 | −121 | 37 | 6 | 7 | 4 |
| XIRP1 (CMYA1) | NM_194293 | 173 | −201 | −29 | 4 | 8 | 0 |
| COL19A1 | NM_001858 | 168 | −308 | −141 | 4 | 7 | 0 |
| CSPP1 | NM_024790 | 330 | −584 | −255 | 2 | 10 | 1 |
| CYP1A1 | NM_000499 | 259 | −588 | −330 | 16 | 23 | 7 |
| DBN1 | NM_004395 | 165 | −629 | −465 | 3 | 9 | 0 |
| DPAGT1 | NM_001382 | 182 | −330 | −149 | 6 | 10 | 1 |
| DPYD | NM_000110 | 214 | −409 | −196 | 4 | 12 | 2 |
| DSCAML1 | NM_020693 | 205 | −630 | −426 | 4 | 9 | 3 |
| DTNB | NM_183361 | 189 | −312 | −124 | 14 | 13 | 5 |
| EGFR | NM_005228 | 390 | −405 | −16 | 21 | 28 | 4 |
| EPHB6 | NM_004445 | 172 | −414 | −243 | 10 | 17 | 3 |
| EPM2AIP1 | NM_014805 | 316 | −346 | −78 | 12 | 23 | 4 |
| ERCC6 | NM_000124 | 171 | −127 | 43 | 11 | 18 | 4 |
| FBXW7 | NM_033632 | 204 | −685 | −482 | 16 | 17 | 8 |
| FHIT | NM_002012 | 311 | 140 | 450 | 18 | 17 | 6 |
| GEN1 (FLJ40869) | NM_182625 | 245 | −639 | −395 | 28 | 25 | 3 |
| GALNS | NM_000512 | 242 | −341 | −100 | 18 | 22 | 8 |
| GPR158 | NM_020752 | 315 | −629 | −315 | 20 | 26 | 17 |
| GSTP1 | NM_000852 | 266 | 29 | 294 | 22 | 23 | 15 |

TABLE 3-continued

Target loci and positions relative to the TSS

| Gene | Accession | Length (bp) | TSS from left (bp) | TSS from right (bp) | #HCG | #GCH | #GCG |
|---|---|---|---|---|---|---|---|
| GUCY1A2 | NM_000855 | 313 | −593 | −281 | 11 | 20 | 4 |
| H19 | AK311497 | 177 | −544 | −368 | 7 | 13 | 2 |
| HIST1H1B | NM_005322 | 208 | −490 | −283 | 2 | 10 | 1 |
| ICAM5 | NM_003259 | 178 | −336 | −159 | 8 | 14 | 3 |
| IGFBP3 | NM_000598 | 276 | −446 | −171 | 17 | 17 | 8 |
| ITGAE | NM_002208 | 349 | −685 | −337 | 7 | 19 | 2 |
| KCNQ5 | NM_019842 | 273 | −158 | 114 | 14 | 19 | 7 |
| PRUNE2 (KIAA0367) | NM_015225 | 235 | −519 | −285 | 10 | 25 | 8 |
| CTIF (KIAA0427) | NM_014772 | 220 | −402 | −183 | 9 | 17 | 6 |
| SZT2 (KIAA0467) | NM_015284 | 267 | 32738 | 33004 | 6 | 17 | 0 |
| KIAA0556 | NM_015202 | 353 | −428 | −76 | 21 | 28 | 17 |
| SIK3 (KIAA0999) | NM_025164 | 252 | −658 | −407 | 8 | 11 | 5 |
| FAM171B (KIAA1946) | NM_177454 | 212 | −447 | −236 | 4 | 14 | 1 |
| LAMA1 | NM_005559 | 169 | −297 | −129 | 10 | 12 | 4 |
| MYLK4 (LOC340156) | NM_001012418 | 175 | −234 | −60 | 3 | 5 | 0 |
| LRRFIP1 | NM_004735 | 165 | −546 | −382 | 10 | 11 | 4 |
| MGMT | NM_002412 | 255 | −108 | 147 | 26 | 25 | 10 |
| MLH1 | NM_000249 | 373 | 101 | 284 | 19 | 18 | 4 |
| NF1 | NM_000267 | 198 | −188 | 9 | 13 | 18 | 6 |
| NKX2-5 | NM_004387 | 184 | 2790 | 2973 | 4 | 9 | 6 |
| NOTCH1 | NM_017617 | 282 | −674 | −393 | 28 | 32 | 6 |
| NUP214 | NM_005085 | 201 | −308 | −108 | 5 | 14 | 7 |
| PCDHA9 | NM_014005 | 247 | −476 | −230 | 4 | 9 | 0 |
| PDCD11 | NM_014976 | 246 | −621 | −376 | 13 | 14 | 4 |
| PIK3CA | NM_006218 | 270 | 645 | 376 | 12 | 21 | 3 |
| PLEKHA8 | NM_032639 | 334 | 251 | −82 | 25 | 23 | 15 |
| PPM1E | NM_014906 | 170 | −328 | −159 | 5 | 6 | 5 |
| PRPF4B | NM_003913 | 225 | −385 | −161 | 8 | 8 | 2 |
| RARB | NM_000965 | 222 | 83 | 306 | 10 | 11 | 2 |
| RASSF1 | NM_007182 | 198 | −189 | 9 | 10 | 12 | 9 |
| RP1L1 | NM_178857 | 221 | −466 | −246 | 5 | 13 | 2 |
| SCN3B | NM_018400 | 382 | −696 | −315 | 5 | 20 | 6 |
| EXOC4 (SEC8L1) | NM_021807 | 345 | −621 | −277 | 4 | 10 | 0 |
| SEMA3B | NM_004636 | 316 | −92 | 253 | 8 | 21 | 9 |
| SFRS6 | NM_006275 | 338 | −595 | −258 | 23 | 20 | 12 |
| SH3TC1 | NM_018986 | 157 | −193 | −37 | 6 | 19 | 4 |
| SLC8A3 | NM_182932 | 304 | −564 | −261 | 6 | 17 | 3 |
| SLC9C1 (SLC9A10) | NM_183061 | 195 | −206 | −12 | 2 | 9 | 1 |
| SMAD4 | NM_005359 | 217 | −272 | −56 | 12 | 20 | 9 |
| SORL1 | NM_003105 | 125 | −542 | −418 | 1 | 5 | 2 |
| SOX10 | NM_006941_1 | 213 | 897 | 1111 | 14 | 24 | 8 |
| SULF2 | NM_018837 | 211 | −449 | −239 | 13 | 17 | 8 |
| TAF1 | NM_004606 | 153 | −440 | −288 | 11 | 10 | 1 |
| TIAM1 | NM_003253 | 283 | −467 | −185 | 22 | 29 | 18 |
| TMEM123 | NM_052932 | 383 | −582 | −200 | 9 | 20 | 2 |
| TNN | NM_022093 | 161 | −605 | −445 | 2 | 5 | 1 |
| TP53 | NM_000546 | 154 | −181 | −28 | 3 | 8 | 3 |
| UHRF2 | NM_152896 | 185 | −417 | −233 | 7 | 12 | 3 |
| UQCRC2 | NM_003366 | 163 | −585 | −423 | 8 | 8 | 2 |
| VEPH1 | NM_024621 | 210 | −429 | −220 | 5 | 5 | 0 |
| XDH | NM_000379 | 276 | −340 | −65 | 2 | 15 | 1 |
| ZMYM4 (ZNF262) | NM_005095 | 302 | −394 | −93 | 14 | 23 | 7 |
| ZNF646 | NM_014699 | 202 | −607 | −406 | 6 | 16 | 1 |

EXAMPLE 3

Can Gene Promoter Methylation and Chromatin Accessibility in NSC and GBM L0

The patterns of DNA methylation and chromatin accessibility were examined at each targeted gene promoter to identify loci exhibiting tumor-specific epigenetic features. To integrate DNA methylation and chromatin accessibility information, these analyses were conducted on the NSC and GBM L0 samples treated with 100 U M.CviPI. We first quantified the fraction of methylated CGs at each promoter for which we obtained at least 10× sequencing coverage in both samples (71 promoters). Promoters exhibiting ≤20% CG methylation were classified as "unmethylated," those with ≥80% methylation were classified as "methylated," and those with 21-79% CG methylation were considered to have "variable" methylation. Overall, we observed that both NSC and GBM L0 had a similar distribution of promoters by methylation status (FIG. 4A). For each promoter, we calculated the fraction of accessible GCs. As expected, GC accessibility was inversely correlated with CG methylation for both samples (FIG. 4B,C). Interestingly, though, a similar decrease in GC accessibility was observed among promoters that were methylated and variably methylated as compared to unmethylated.

Figure 5:
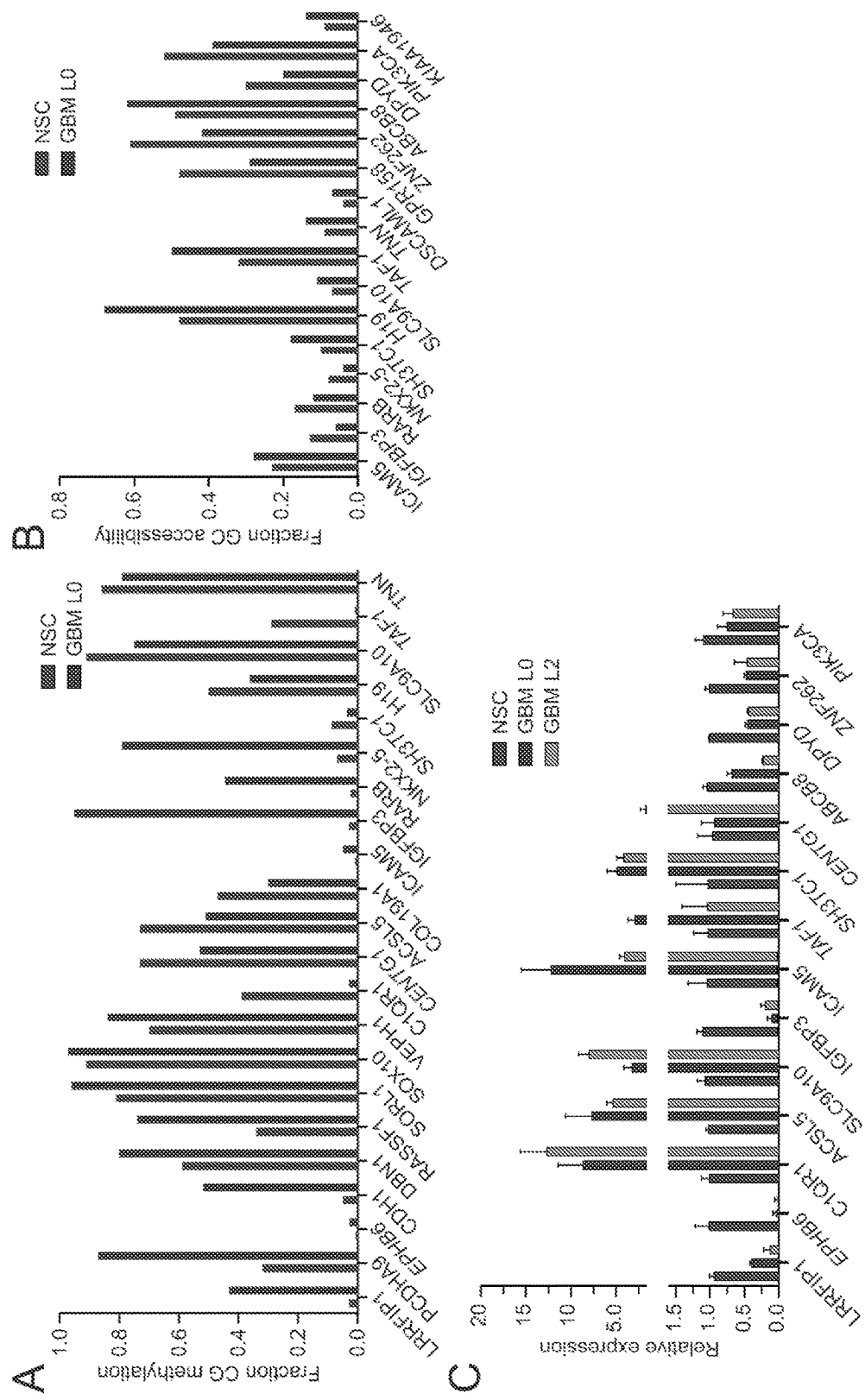

MAPit-patch identified thirteen promoters with differential CG methylation (DMR, differentially methylated region), seven with differential GC accessibility (DAR, differentially accessible region), and nine with both differential CG methylation and GC accessibility (DMAR, differentially methylated and accessible region) (FIG. 5A,B). These genes exhibited reproducible differences (P<0.01; NSC 0 U M.CviPI versus GBM 0 U and NSC 100 U versus GBM 100 U) and no statistically significant differences in CG methylation between replicates (NSC 0 U versus NSC 100 U and GBM 0 U versus GBM 100 U). We selected 15 promoters (5 DMR, 4 DAR, and 6 DMAR) and measured gene expression in the NSC culture as well as two primary GBM cultures derived from different patients (L0 and L2), using quantitative reverse transcription PCR (qRT-PCR). Ten of fifteen tested promoters exhibited the expected correlations between altered CG methylation, chromatin accessibility, and gene expression (FIG. 5). Two genes (CENTG1 and TAF1) showed no expression change in one GBM culture, but the expected change in the other GBM culture. Finally, three promoters showed unexpected changes in gene expression (ICAM5, NKX2-5, and ABCB8; NKX2-5 expression data not graphed due to 6,500 and 2,800-fold increases in GBM L0 and GBM L2, respectively, compared to NSC). For ICAM5, the increase in expression correlates with the increase in GC accessibility rather than the small site-specific increase in CG methylation. These results indicate that the differential epigenetic features identified by MAPit-patch are reflective of differential gene expression in most cases. Importantly, most of the genes that are differentially expressed between NSC and GBM L0 were also differentially expressed in GBM L2. This indicates that these differentially methylated and/or accessible genes, though known to be associated with colon and/or breast cancer, may also be generally affected in GBMs.

EXAMPLE 4

Figure 11:
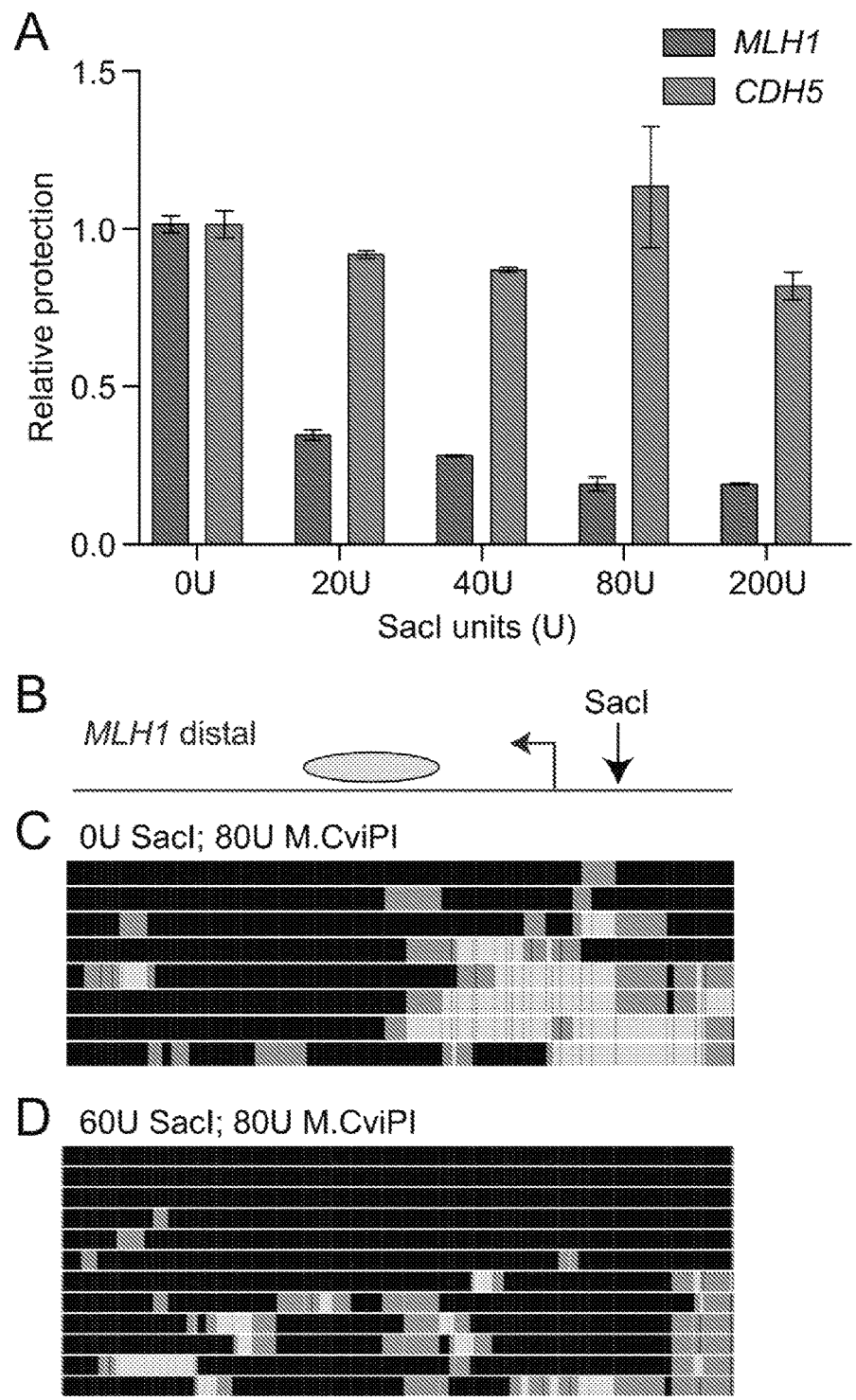

Heterogeneity in Chromatin Accessibility and DNA Methylation at Multiple can Gene Promoters To identify epigenetic heterogeneity, we examined the CG methylation and GC accessibility patterns in the target gene promoters that sequenced with ≥20× coverage (54 promoters from NSC; 67 promoters from GBM L0). Promoters were divided into quintiles and classified as follows: 1) accessible (≥80% molecules accessible); 2) mostly accessible (79-61% molecules accessible); 3) half accessible (60-40% molecules accessible); 4) mostly inaccessible (39-20% molecules accessible); and 5) inaccessible (≤19% molecules accessible) (FIG. 6A). The distribution of promoter amplicons among the five different accessibility classes was similar for both NSC and GBM L0 (FIG. 6B). To provide independent assessment that MAPit-patch accurately assesses the degree of accessibility characteristic of each class of promoters, we performed quantitative restriction enzyme accessibility assays (FIG. 6C; assay optimization in FIG. 11). We then identified four promoters that contain a SacI site within 350 bp of a TSS and for which we obtained ≥20× coverage by MAPit-patch. After incubation of nuclei with SacI, accessibility was quantitatively measured by QPCR with convergent primers spanning each SacI site. The accessibility profiles of all four promoters in FIG. 6C corresponded well with those determined by MAPit-patch (Table 1). Confirmation of accessibility by this independent, quantitative approach indicates that the heterogeneous accessibility patterns identified by MAPit-patch reflect biological diversity in chromatin accessibility, not only among the interrogated promoters but also across the cohort of molecules for each promoter. CG methylation was inversely correlated with GC accessibility for both NSC and GBM L0 samples (FIG. 6D,E). The stepwise trend of increased CG methylation observed as GC accessibility decreases between chromatin classes suggests a non-random distribution of promoters into these five classes that is linked to its epigenetic state. Also note the heterogeneous distribution of CG methylation levels within the inaccessible class of promoters. The absence of high CG methylation within accessible or mostly accessible promoters coupled with the lack of GC accessibility observed in variably methylated promoters (FIG. 4) suggests that loss of chromatin accessibility precedes accumulation of DNA methylation.

Figure 6:
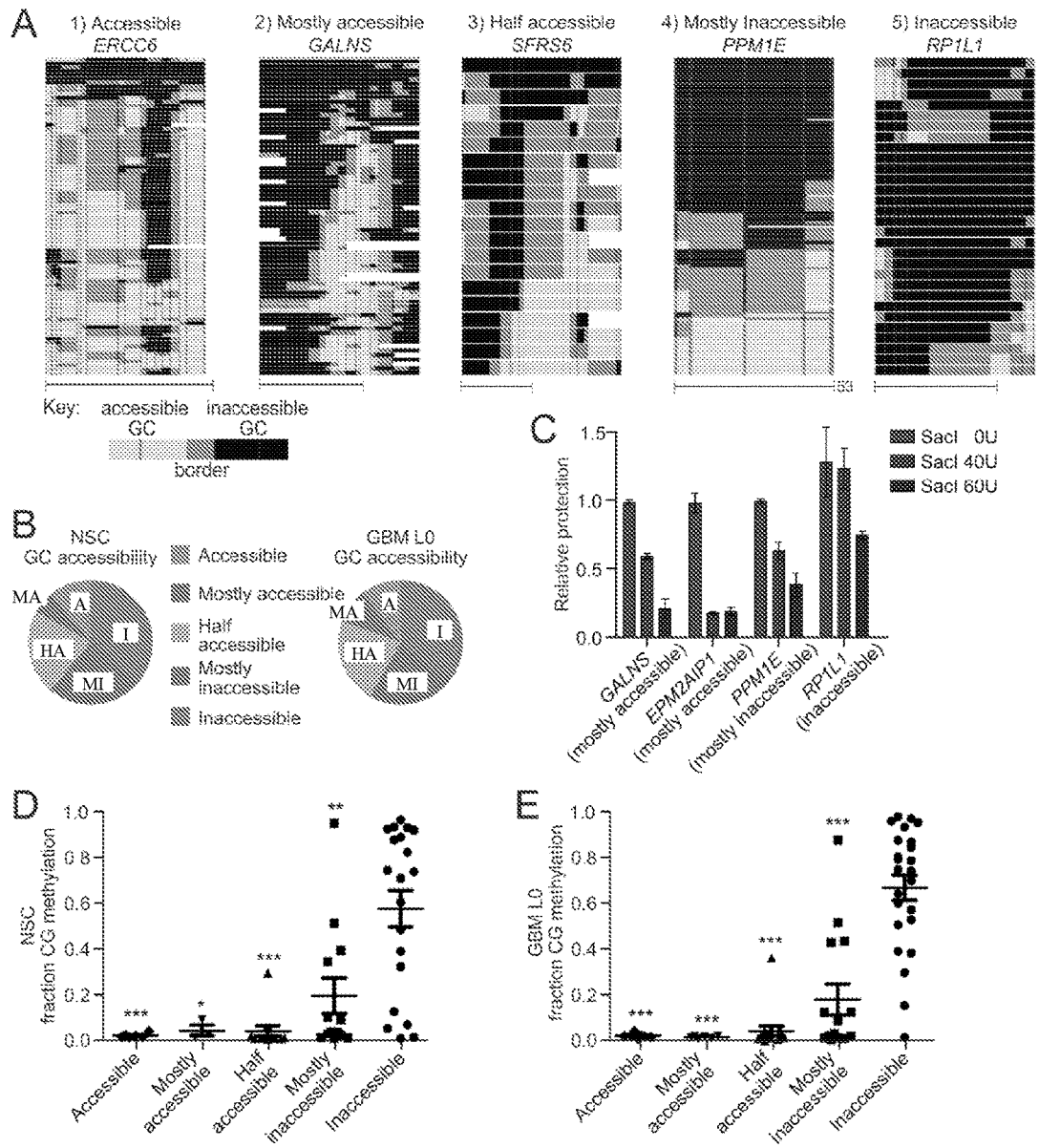

Analyzing epigenetic features in spheroid cells, above we classified CG methylation into three states (FIG. 4) and chromatin accessibility into five states (FIG. 6). Integrating these features yields fifteen possible configurations. However, upon parsing the promoters according to combined levels of DNA methylation and chromatin accessibility, we observed that only 10 of the 15 potential states were represented. Parsing the differentially methylated promoters (DMR+DMAR) into these classes shows, in NSC, enrichment for promoters that are variably methylated and inaccessible (3.0% vs. 28.6; P=0.0108; Table 4, left, compare gray cells). In contrast, DMR+DMARs from GBM L0 exhibited an enrichment for methylated and inaccessible promoters (4.4% vs. 31.8; P=0.0043; Table 4, right, compare gray cells). These data show that, in contrast to genes that are not epigenetically altered, most genes identified as differentially methylated between GBM L0 and NSC were initially variably methylated and inaccessible in NSC.

Figure 7:
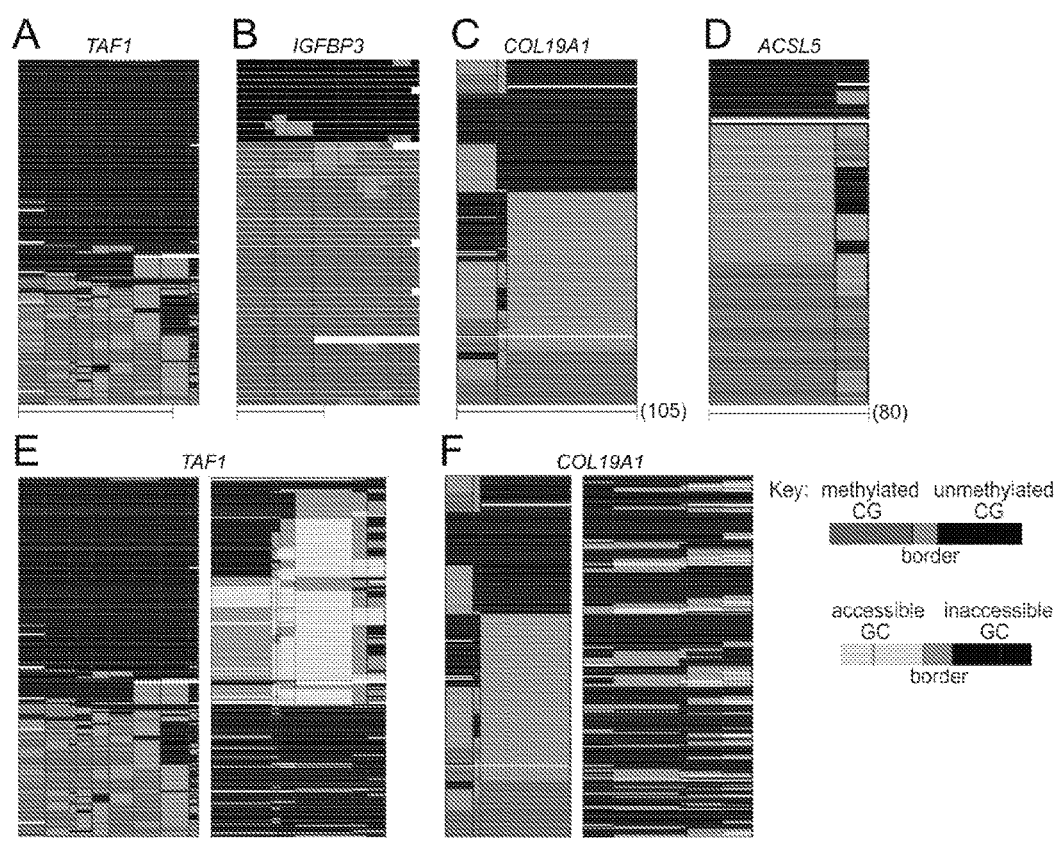

Upon examining the DNA methylation and chromatin accessibility patterns of the variably methylated promoters, we observed two different patterns of variability. At some promoters, the majority of molecules were densely methylated or mostly unmethylated, whereas a subgroup of molecules show the opposing profile (FIG. 7A,B). Alternatively, there are promoters that show a more random distribution of CG methylation across all molecules (FIG. 7C,D). Interestingly, for promoters that show a bimodal distribution of dense and sparse CG methylation, GC accessibility is often restricted to the sparsely methylated molecules (FIG. 7E). In contrast, at promoters with a more random distribution of CG methylation, there is no apparent preference for accessed GC sites (FIG. 7F). It should be noted that all the amplicons displaying a seemingly random distribution of CG methylation (12 in GBM L0) were in regions with low CG site density (data not shown). The occurrence of both methylated-inaccessible and unmethylated-accessible molecules at a single locus has previously been described for imprinted and other monoallelically expressed genes. We also observed this at the imprinted H19 locus (P=0.01, FIG. 12), TAF1 (P=0.0001, FIG. 7E) and CLEC4C (P=0.001, FIG. 12).

TABLE 4

Integration of DNA methylation and chromatin accessibility. Promoters were parsed into each of 15 potential classes of integrated CG methylation and GC accessibility. The percentage of promoters in each integrated epigenetic state is listed. The upper table shows the class distribution of promoters that were not statistically different between NSC (left) and GBM (right). The lower table shows the class distribution of promoters that were differentially methylated (DMRs and DMARs from Table 1 and 3, respectively, ≥20× coverage) from NSC (lower left) and GBM (lower right). Gray shading highlights epigenetic classes that are enriched in DMRs plus DMARs compared to all other promoters (i.e., bottom panel vs. upper panel).

| NSC | Unmethylated | Variable | Methylated | GBM | Unmethylated | Variable | Methylated |
|---|---|---|---|---|---|---|---|
| Inaccessible | 12.1 | 3.0 | 12.1 | Inaccessible | 4.4 | 15.6 | 4.4 |
| Mostly Inaccessible | 21.2 | 0.0 | 3.0 | Mostly Inaccessible | 22.2 | 0.0 | 2.2 |
| Half | 24.2 | 0.0 | 0.0 | Half | 26.7 | 0.0 | 0.0 |
| Mostly accessible | 6.1 | 0.0 | 0.0 | Mostly accessible | 11.1 | 0.0 | 0.0 |
| Accessible | 18.2 | 0.0 | 0.0 | Accessible | 13.3 | 0.0 | 0.0 |
| NSC (DMR + DMAR) | Unmethylated | Variable | Methylated | GBM (DMR + DMAR) | Unmethylated | Variable | Methylated |
| Inaccessible | 4.8 | 28.6 | 19.0 | Inaccessible | 0.0 | 27.3 | 31.8 |
| Mostly Inaccessible | 9.5 | 14.3 | 0.0 | Mostly Inaccessible | 4.5 | 13.6 | 0.0 |
| Half | 14.3 | 4.8 | 0.0 | Half | 9.1 | 4.5 | 0.0 |
| Mostly accessible | 4.8 | 0.0 | 0.0 | Mostly accessible | 4.5 | 0.0 | 0.0 |
| Accessible | 0.0 | 0.0 | 0.0 | Accessible | 4.5 | 0.0 | 0.0 |

EXAMPLE 5

A Subpopulation of Drug-Tolerant Cells is Associated with Increased Promoter Nucleosome Occupancy Next, we wanted to determine if any epigenetic subpopulations we observed in GBM L0 were associated with disease-relevant phenotypes. The divergent MLH1/EPM2AIP1 promoter was unmethylated and mostly accessible in GBM at both patch-targeted loci. There was, however, a subpopulation of molecules that were almost completely inaccessible in both the proximal and distal promoter regions (FIG. 8A-F). The protein product of MLH1 is involved in DNA mismatch repair and is considered a tumor suppressor. Genetic or epigenetic inactivation of MLH1 is common in colon and endometrial cancer. Importantly, it is known that loss of Mlh1 protein expression renders cells insensitive to treatment with DNA alkylating agents such as temozolomide (TMZ) (Taverna et al. 2000), which is the frontline chemotherapeutic treatment for GBM. We hypothesized that the subpopulation of MLH1 promoter copies with inaccessible chromatin observed in GBM may reflect a cellular subpopulation that does not express Mlh1 and may therefore be tolerant to TMZ.

Figure 13:
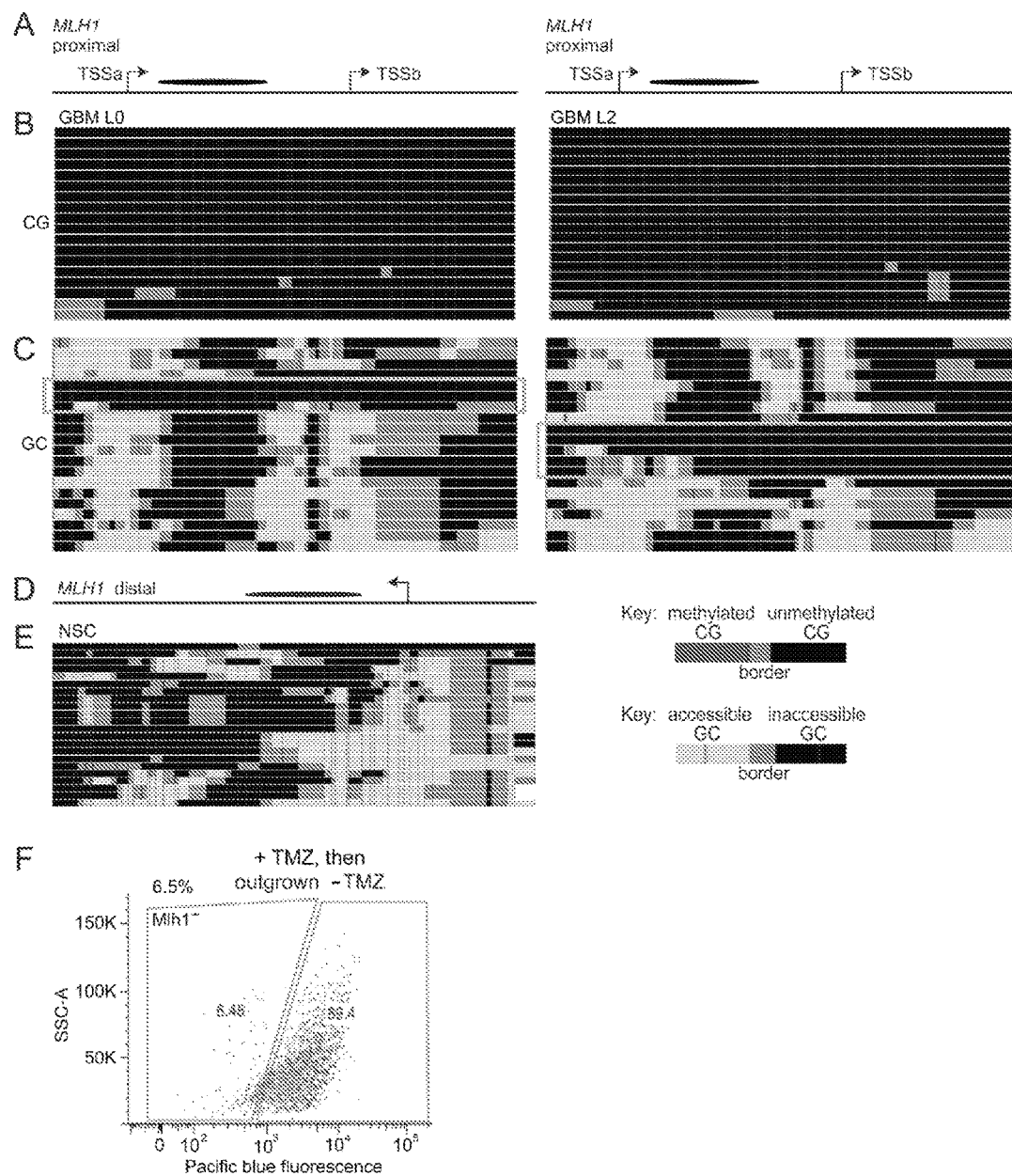

First, we conducted MAPit-BGS to confirm that identification of this inaccessible subpopulation by MAPit-patch was reproducible. As before, we observed that the epigenetic status of MLH1 was unmethylated and mostly accessible, with an inaccessible subpopulation at both the proximal (FIG. 13A-C) and distal promoter regions (FIG. 8D-F). This was observed in GBM L0 (FIG. 8E) as well as in GBM L2 (FIG. 8F), but not in NSCs (FIG. 2B and FIG. 13D,E). Notably, this inaccessible subpopulation was specific to MLH1 and was not observed at the completely accessible promoter of the PMS2 gene, which encodes the mismatch repair binding partner of Mlh1 (FIG. 8G-I). Immunostaining for Mlh1 followed by flow cytometry showed that both GBM lines contained a subpopulation of Mlh1-negative or low-expressing cells (FIG. 8J-L).

To determine if the Mlh1-low or Mlh1-negative phenotype was associated with copies of MLH1 promoter chromatin that were inaccessible, GBM cells were treated with TMZ for 4 days to counterselect cells expressing Mlh1 protein. Flow cytometry of immunostained cells confirmed dose-dependent enrichment for Mlh1-negative/low cells upon treatment with TMZ (FIG. 9A-C). Surviving TMZ-tolerant cells were then assayed for accessibility of distal MLH1 promoter chromatin by MAPit-BGS or SacI digestion and found to be enriched for inaccessible chromatin (P<0.0001) (FIG. 9F; 9H, middle). An aliquot of TMZ-tolerant cells from the same experiment was outgrown in the absence of TMZ for 10 additional passages and assayed for chromatin accessibility. Compared to the starting TMZ-tolerant cells (FIG. 9F; 9H, middle), the outgrown cells exhibited a significant (P<0.0001) increase in accessibility of distal MLH1 promoter chromatin to M.CviPI and SacI (FIG. 9G; 9H, right) and also re-expressed Mlh1 protein (FIG. 13F). This supports our hypothesis that chromatin inaccessibility, and by extension increased nucleosome occupancy, reflects decreased Mlh1 expression despite the absence of DNA methylation.

EXAMPLE 6

Expression of DNA a Methyltransferase in Live Cells Identifies Dynamic Regions of Chromatin MAPit-patch using delivery of a DNA methyltransferase probe in live cells identifies accessible and inaccessible promoters. HCT116 colorectal cancer cells were transiently transfected with vector pLenti CMV/TO GFP-Zeo (Addgene plasmid 17431) containing separate genes encoding M.CviPI (with C-terminal Myc tag) and green fluorescent protein (GFP), both optimized for human codon preferences and expression driven by the strong, constitutive cytomegalovirus promoter. Cells were harvested and subjected to fluorescence-activated cell sorting to collect cells expressing GFP, and by extension, M.CviPI. Genomic DNA was extracted, processed, sequenced, and data analyzed according to the MAPit-patch protocol. Inverse correlation between GC accessibility and endogenous CG methylation in the overall set of MAPit-patch amplicons analyzed (FIG. 15A), as well as hypomethylated and highly accessible GALNS promoter (FIG. 15B, left) and hypermethylated and relatively inaccessible CLEC4C promoter (FIG. 15B, right). The inverse correlation between GC accessibility and endogenous CG methylation indicates that delivery of M.CviPI to live cells accurately identifies accessible and inaccessible chromatin, thus validating the use of DNA methyltransferases as probes of chromatin structure when expressed in live mammalian cells.

Figure 17:
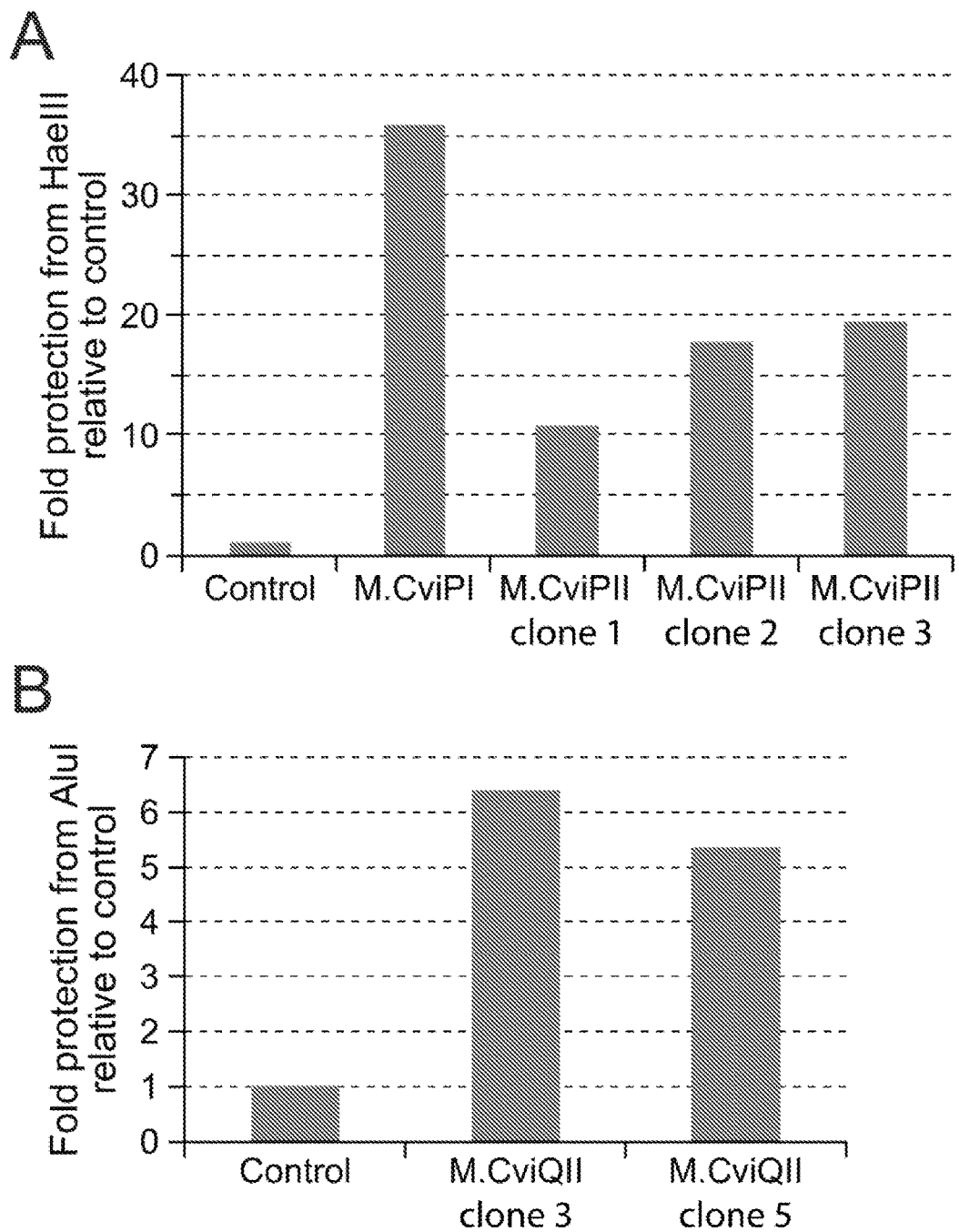

MAPit-patch using delivery of a DNA methyltransferase probe in live cells may be used to identify regions of dynamic occupancy by DNA-binding factors. The example (FIG. 16A) depicts four single molecules (upper) and the overall consensus view (lower) of chromatin accessibility at two different hypothetical loci. In the case where a nucleosome (blue oval) is highly dynamic (left), i.e., occupies several distinctly different positions, on average, molecules will exhibit accessibility over a broader region. By contrast, in the case where a nucleosome is well positioned, i.e., occupies a fairly constant position, the central region of the nucleosome will be protected against exogenous methylation. We compared chromatin accessibility data at promoters exhibiting either dynamically moving nucleosomes, for example at the CLCN3 promoter (FIG. 16B), or a fairly well-positioned DNA-binding factor, for example at the ERCC6 promoter (FIG. 16C). Data were obtained from probing either nuclei with purified M.CviPI in the presence of methyl donor cofactor (S-adenosyl methionine) for 15 min (left) versus in live cells with 24 hrs transfection of pLenti CMV/TO M.CviPI-Myc (right). Note that at the less dynamic ERCC6 locus, probing either in nuclei or in live cells yields similar results with a constant protected region, in contrast, CLCN3 locus exhibits increased overall chromatin accessibility in live cells compared with nuclei, suggesting this is a more dynamic locus. Note that two additional DNA methyltransferases: M.CviPII (recognition sequence CCD, first C modified, where D is A, G or T) and M.CviQII (recognition sequence RAG, where R is A or G) may also be delivered in live cells to methylate accessible target sites (FIG. 17).

EXAMPLE 7

Discussion of the Results Obtained in Example 1 to Example 6

Integrated determination of epigenetic features is important for understanding how epigenetic mechanisms contribute to tumorigenesis and how to effectively target them for cancer treatment. Single-molecule level technologies that preserve the heterogeneity inherent to human tumors are essential to fully understand the contribution of these factors to disease progression and resistance to treatment. We have described a novel deep sequencing approach, termed MAPit-patch, which simultaneously determines chromatin structure and DNA methylation with single-molecule resolution, thus preserving sample heterogeneity. The method is highly scalable and affordable which should facilitate screening multiple tissue samples. Also, the targeted (rather than genome-wide) approach is within reach for transitioning these technologies for clinical application where assessment of particular disease biomarkers is required. Using MAPit-patch, we have shown that epigenetic heterogeneity at a given locus is commonly observed. Furthermore, our results indicate that in addition to DNA hypomethylation or hypermethylation, changes in chromatin accessibility alone are associated with tumor-specific alterations in gene expression. Finally, we have shown for the first time that a small cellular subpopulation of cells with inaccessible chromatin (not DNA methylation) at tumor-suppressive genes may impact disease-relevant phenotypes (i.e., drug tolerance) in GBM. These results show that epigenetic heterogeneity may underlie some of the phenotypic diversity observed in human GBM and has broad implications for molecular profiling of tumors in general.

MAPit-patch achieves synergistic advances by combining and retaining all the key features of single-molecule MAPit methylation footprinting and interrogation of DNA methylation by bisulfite patch PCR. MAPit is the only method currently available for single-molecule level determination of chromatin accessibility, which is essential for understanding the biology of heterogeneous cellular populations. Notably, combined DNA methylation and chromatin accessibility data is more informative than either single feature in determining the expression potential of a promoter. Thus integrating detection of these features not only decreases experimental effort and cost of assaying each feature separately, but also allows for a more comprehensive assessment of a promoter's potential for gene expression.

MAPit constrains the number of restriction enzymes suitable for the back-end analysis of DNA methylation by bisulfite patch PCR. Enzymes need to be insensitive to both CG and GC methylation and have a 4-bp recognition sequence, so that fragments are in the size range that can be efficiently PCR amplified in preparation for deep sequencing. Additionally, the enzyme should cut efficiently and be inactivated by heat so that purification after digestion is not required. Additional enzymes besides AluBI that meet these parameters include MseI and DpnII.

The ability to use low input quantities of DNA is another benefit of bisulfite patch PCR and successful amplification of targeted loci with it was reported that as little as 20 ng of DNA has been reported (Varely and Mitra 2010). However, we observed an increase in the number of duplicate molecules sequenced when the amount of input DNA was decreased from 500 ng to 250 ng (data not shown). Nonetheless, 500 ng is a lower input requirement than alternate bisulfite sequencing approaches that require 5-20 µg of DNA.

We identified a number of genes that were differentially methylated and/or accessible and differentially expressed between NSC and GBM. It should be noted that the majority of promoters exhibiting tumor hypermethylation and/or hypo-accessibility regulate genes with tumor-suppressive functions. These included: IGFBP3 (insulin-like growth factor binding protein), a tumor suppressor gene frequently hypermethylated in multiple cancer types (Shen and Glazer 1998; Shen et al. 1999; Santosh et al. 2010); EPHB6 encodes a receptor tyrosine kinase involved in suppressing metastasis, frequently hypermethylated (Yu et al. 2010), LRRFIP1 encodes a DNA binding protein that inhibits NF-kB signaling; loss of expression which is associated with chemoresistance (Suriano et al. 2005; Li et al. 2009), PCDHA9 encodes protocadherin alpha, important for maturation of specific types of neurons, commonly hypermethylated (Dallosso et al. 2009; Katori et al. 2009) and DPYD encodes dihydropyrimidine dehydrogenase, which metabolizes chemotherapeutic agents thus sensitizing cells to treatment and is frequently mutated in multiple cancers (Amstutz et al. 2011). Interestingly, ICAM5 (encodes a transmembrane glycoprotein important for neural cell-to-cell interactions) has been associated with tumor-promoting functions such as tumor invasion and is overexpressed in breast and head and neck squamous cell carcinoma (Maruya et al. 2005). ICAM5 is, however, hypermethylated in colon cancer (Mokarram et al. 2009). We observed that ICAM5 is hypermethylated and shows increased expression in GBM compared to NSC (FIG. 5A,C). This promoter may be subject to site-specific methylation events that inhibit repressor binding, thereby increasing gene expression, as reported for other genes (Renaud et al. 2007; Nabilsi et al. 2009; Lai et al. 2010). Similarly, NKX2-5, encoding a homeobox-containing transcription factor with suspected tumor-promoting function (Nagel et al. 2008), was observed to be hypermethylated (FIG. 5A) and expressed in GBM L0 (expression data not graphed, 6,550-fold increase in GBM L0 and 2,820-fold increase in GBM L2 compared to NSC). NKX2-5 was initially included as a control gene that is usually methylated and the amplicon for NKX2-5 is located in the gene body rather than the promoter. In contrast to promoter methylation, gene body methylation is generally associated with active gene expression.

In contrast to hypermethylated and/or hypo-accessible tumor suppressor promoters, hypomethylation and/or hyper-accessibility was observed at known or suspected tumor-promoting genes. These include: COL19A1, which encodes an embryonic fibril-associated collagen, overexpressed in glioma (Sumiyoshi et al. 1997); TAF1, encoding a TBP-associated factor with histone acetyltransferase and ubiquitin-conjugating activity, which is overexpressed in prostate tumors and is hypomethylated in uterine tumors (Tavassoli et al. 2010; Maekawa et al. 2011); C1QR1 encodes inflammatory mediator CD93 that is overexpressed in GBM-associated vasculature (Dieterich et al. 2012); CENTG1, the protein product which is a GTPase that enhances PI3-kinase function, is a known oncogene in GBM and is hypomethylated in salivary tumors (Knobbe et al. 2005; Maekawa, Yagi et al. 2011) and ACSL5, which encodes acetyl-coA synthase that enhances glioma cell survival (Mashima et al. 2009). Finally, ABCB8, encoding an ATP-binding cassette transporter implicated in mediating drug resistance (Elliott and Al-Hajj 2009), was observed to be hyper-accessible, but exhibited decreased gene expression in GBM compared to NSC. Though chromatin accessibility is generally associated with active expression, there are cases where DNA binding of activating factors can decrease accessibility to increase gene expression, i.e., footprints at activator binding sites (Gal-Yam et al. 2006). Conversely, increased accessibility at ABCB8 may reflect loss of activator binding.

These results suggest that differential chromatin accessibility may serve as an additional epigenetic feature that can identify differentially expressed genes in tumor cells. The identification of hypomethylation/hyper-accessibility at tumor-promoting genes and hypermethylation/hypo-accessibility at tumor-suppressive genes suggests that these epigenetic features are not random, but represent biologically relevant events. Finally, the fact that many differentially methylated/accessible genes were previously observed to be genetically dysregulated in GBM supports the validity of this approach to identify GBM-relevant epigenetic perturbations.

Interestingly, most of the genes that were identified as differentially methylated between GBM L0 and NSC were classified as variably methylated in NSC (Table 4, lower). It has been reported that loci that exhibit variability in methylation status between different types of normal tissues are more often aberrantly methylated in tumors. The proposed explanation is that these regions exhibit the greatest amount of epigenetic plasticity and will therefore be more susceptible to perturbations during tumorigenesis. Our results suggest that this same phenomenon may be observed within a given sample, whereby loci that are variably methylated within the cellular population in a normal tissue (rather than across different tissue types) are more amenable to aberrant hypomethylation or hypermethylation in tumors. However, assessment of additional loci in several normal and tumor samples are necessary to support this premise. We were also surprised that many of the differentially methylated genes were hypomethylated rather than hypermethylated in GBM L0 compared to NSC. This could be due to the fact that target selection was based on loci that are aberrantly expressed in breast and/or colon cancer. These loci may be normally repressed in neural tissues and there may be a loss-of-imprinting phenomenon occurring in GBM L0. This is supported by the epigenetic patterns observed at H19 where local depletion of DNA methylation and gain of chromatin accessibility is observed on a subset of methylated molecules in GBM L0 but not in NSC (FIG. 12 compared to FIG. 3D). Alternatively, more tumor-promoting genes may have been represented in the target selection library than tumor-suppressive genes, which would also account for more occurrences of hypomethylation.

Using the MAPit-patch method of the current invention, we showed that deep sequencing coverage at candidate loci could identify epigenetically distinct cellular subpopulations within a given NSC or GBM spheroid culture. We observed that the levels of heterogeneity in chromatin accessibility were highly similar in NSC and GBM L0 cells (FIG. 6B). Both cell types were cultured under conditions that prevent differentiation and maintain cellular plasticity. When NSCs are transferred to growth conditions that promote attachment to a solid surface and are supplemented with appropriate factors, they differentiate to neurons, astrocytes, and oligodendrocytes (Siebzehnrubl et al. 2011). Similarly, when spheroid-cultured GBM cells are injected into nude mice, they recapitulate the morphological, phenotypic and molecular heterogeneity of the initial tumor (Deleyrolle et al. 2011). Thus, the extensive epigenetic heterogeneity observed within these cellular populations may reflect a common feature of progenitor-type cells.

Additionally, we found that a subpopulation of molecules with inaccessible chromatin at the MLH1 promoter was associated with a cellular subpopulation of Mlh1-negative/low cells. Tumors with genetic or epigenetic inactivation of MLH1 commonly exhibit microsatellite instability, which is not commonly observed in human GBM. This is probably because only a small percentage of GBM cells are negative for Mlh1, which is consistent with reports of low-grade microsatellite instability in GBM (Szybka et al. 2003; Martinez et al. 2005). We subsequently showed that this Mlh1-negative/low subpopulation with inaccessible chromatin is enriched upon treatment with TMZ. These results are significant for several reasons. First, although a biomarker exists to predict sensitivity to TMZ treatment (MGMT promoter methylation), a biomarker for TMZ resistance in GBM remains undiscovered. While Mlh1 and Mgmt are both involved in DNA mismatch repair, Mlh1 functions upstream of Mgmt, and senses rather than repairs DNA lesions. As such, aberrant expression of Mlh1 would presumably supersede the effects of aberrant Mgmt expression in affecting sensitivity to TMZ. Second, two previous studies have shown, by immunohistochemistry, that subpopulations of Mlh1 negative cells exist in primary human GBM. One study showed that Mlh1-negative cells were enriched in recurrent tumors after TMZ treatment (Stark et al. 2010). The second study showed that cells lacking Pms2 rather than Mlh1 were enriched in recurrent tumors (Felsberg et al. 2011). Thus loss of mismatch repair protein expression appears to be associated with clinical relapse of GMB and further studies to test these genes as biomarkers of treatment resistance is of high interest. Importantly, DNA methylation was tested and excluded as the mechanism driving MLH1 silencing in these studies. This is consistent with our results which show that aberrant chromatin inaccessibility, but not DNA methylation, is associated with Mlh1-negative GBM cells. This is relevant because studies evaluating epigenetic biomarkers often exclusively query DNA methylation. Our results suggest that chromatin accessibility may also be a useful feature to identify disease biomarkers. Furthermore, DNA methylation is considered a more stable mark of gene silencing than chromatin inaccessibility and consequently, more difficult to reverse pharmacologically. Thus identifying differential chromatin accessibility may yield important prognostic insight and increase approaches to therapeutic intervention.

Upon expanding TMZ-tolerant cells, we show that these cells repopulate to exhibit a more accessible chromatin state at MLHJ. One interpretation is that the inaccessible chromatin state we observed is transiently enriched upon TMZ treatment. This supports the finding that Mlh1-negative cells were not enriched in recurrent human tumors following TMZ treatment (Felsberg et al. 2011). It is also in agreement with a previous report that the drug-tolerant phenotype in cancer cells is transiently obtained and relinquished in a chromatin-dependent manner (Sharma et al. 2010). The transient nature of MLH1 chromatin inaccessibility also suggests that it would be amenable to therapeutic reversal. Modification of the timing for TMZ administration or combination treatment with epigenetic agents may help overcome TMZ tolerance and dampen disease recurrence. Though less likely, we cannot rule out the possibility that the mostly accessible chromatin profile observed in the expanded cells may reflect preferential expansion of a small number of cells with accessible chromatin that survived drug treatment. Additional studies are required to identify the source of cells with accessible chromatin that are present upon expansion of TMZ-tolerant cells.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Amstutz U, Froehlich T K, Largiader C R. 2011. Dihydropyrimidine dehydrogenase gene as a major predictor of severe 5-fluorouracil toxicity. Pharmacogenomics 12(9): 1321-1336.
2. Chan S H, Zhu Z, Van Etten J L, Xu S Y. 2004. Cloning of CviPII nicking and modification system from chlorella virus NYs-1 and application of Nt.CviPII in random DNA amplification. Nucleic Acids Res 32(21): 6187-6199.
3. Dallosso A R, Hancock A L, Szemes M, Moorwood K, Chilukamarri L, Tsai H H, Sarkar A, Barasch J, Vuononvirta R, Jones C, et al. 2009. Frequent long-range epigenetic silencing of protocadherin gene clusters on chromosome 5q31 in Wilms' tumor. PLoS Genet 5(11): e1000745.
4. Darst R P, Nabilsi N H, Pardo C E, Riva A, Kladde M P 2012. DNA methyltransferase accessibility protocol for individual templates by deep sequencing. Methods Enzymol 513: 185-204.
5. Deleyrolle L P, Harding A, Cato K, Siebzehnrubl F A, Rahman M, Azari H, Olson S, Gabrielli B, Osborne G, Vescovi A, et al. 2011. Evidence for label-retaining tumour-initiating cells in human glioblastoma. Brain 134 (Pt 5): 1331-1343.
6. Deleyrolle L P, Reynolds B A. 2009. Isolation, expansion, and differentiation of adult mammalian neural stem and progenitor cells using the neurosphere assay. Methods Mol Biol 549: 91-101.
7. Delmas A L, Riggs B M, Pardo C E, Dyer L M, Darst R P, Izumchenko E G, Monroe M, Hakam A, Kladde M P, Siegel E M, et al. 2011. WIF1 is a frequent target for epigenetic silencing in squamous cell carcinoma of the cervix. Carcinogenesis 32(11): 1625-1633.
8. Dieterich L C, Mellberg S, Langenkamp E, Zhang L, Zieba A, Salomaki H, Teichert M, Huang H, Edqvist P H, Kraus T, et al. 2012. Transcriptional profiling of human glioblastoma vessels indicates a key role of VEGF-A and TGFβ2 in vascular abnormalization. J Pathol 228(3): 378-390.
9. Elliott A M, Al-Hajj M A. 2009. ABCB8 mediates doxorubicin resistance in melanoma cells by protecting the mitochondrial genome. Mol Cancer Res 7(1): 79-87.
10. Esteller M. 2007. Cancer epigenomics: DNA methylomes and histone-modification maps. Nat Rev Genet 8(4): 286-298.
11. Fang G, Munera D, Friedman D I, Mandlik A, Chao M C, Banerjee O, Feng X, Losic B, Mahajan M C, Jabado O J, et al. 2012. Genome-wide mapping of methylated adenine residues in pathogenic *Escherichia coli* using single-molecule real-time sequencing. Nat. Biotechnol. 30(12): 1232-1239.
12. Felsberg J, Thon N, Eigenbrod S, Hentschel B, Sabel M C, Westphal M, Schackert G, Kreth F W, Pietsch T, Loffler M, et al. 2011. Promoter methylation and expression of mgmt and the DNA mismatch repair genes MLH1, MSH2, MSH6 and PMS2 in paired primary and recurrent glioblastomas. Int J Cancer 129(3): 659-670.
13. Fuks F. 2005. DNA methylation and histone modifications: Teaming up to silence genes. Curr Opin Genet Dev 15(5): 490-495.
14. Gal-Yam E N, Jeong S, Tanay A, Egger G, Lee A S, Jones P A. 2006. Constitutive nucleosome depletion and ordered factor assembly at the GRP78 promoter revealed by single molecule footprinting. PLoS Genet 2(9): e160.
15. Hansen K D, Timp W, Bravo H C, Sabunciyan S, Langmead B, McDonald O G, Wen B, Wu H, Liu Y, Diep D, et al. 2011. Increased methylation variation in epigenetic domains across cancer types. Nat Genet 43(8): 768-775.
16. Herman J G, Baylin S B. 2003. Gene silencing in cancer in association with promoter hypermethylation. N Engl J Med 349(21): 2042-2054.
17. Jiang C, Pugh B F. 2009. Nucleosome positioning and gene regulation: Advances through genomics. Nat Rev Genet 10(3): 161-172.

18. Katori S, Hamada S, Noguchi Y, Fukuda E, Yamamoto T, Yamamoto H, Hasegawa S, Yagi T. 2009. Protocadherin-alpha family is required for serotonergic projections to appropriately innervate target brain areas. J Neurosci 29(29): 9137-9147.

19. Kelly T K, Liu Y, Lay F D, Liang G, Berman B P, Jones P A. 2012. Genome-wide mapping of nucleosome positioning and DNA methylation within individual DNA molecules. Genome Res 22(12): 2497-2506.

20. Kilgore J A, Hoose S A, Gustafson T L, Porter W, Kladde M P. 2007. Single-molecule and population probing of chromatin structure using DNA methyltransferases. Methods 41(3): 320-332.

21. Knobbe C B, Trampe-Kieslich A, Reifenberger G. 2005. Genetic alteration and expression of the phosphoinositol-3-kinase/Akt pathway genes PIK3CA and PIKE in human glioblastomas. Neuropathol Appl Neurobiol 31(5): 486-490.

22. Lai A Y, Fatemi M, Dhasarathy A, Malone C, Sobol S E, Geigerman C, Jaye D L, May D, Shah R, Li L, et al. 2010. DNA methylation prevents CTCF-mediated silencing of the oncogene BCL6 in B cell lymphomas. J Exp Med 207(9): 1939-1950.

23. Li Y, Li W, Yang Y, Lu Y, He C, Hu G, Liu H, Chen J, He J, Yu H. 2009. MicroRNA-21 targets LRRFIP1 and contributes to VM-26 resistance in glioblastoma multiforme. Brain Res 1286: 13-18.

24. Maekawa R, Yagi S, Ohgane J, Yamagata Y, Asada H, Tamura I, Sugino N, Shiota K. 2011. Disease-dependent differently methylated regions (D-DMRS) of DNA are enriched on the X chromosome in uterine leiomyoma. J Reprod Dev 57(5): 604-612.

25. Martinez R, Schackert H K, Appelt H, Plaschke J, Baretton G, Schackert G. 2005. Low-level microsatellite instability phenotype in sporadic glioblastoma multiforme. J Cancer Res Clin Oncol 131(2): 87-93.

26. Maruya S I, Myers J N, Weber R S, Rosenthal D I, Lotan R, El-Naggar A K. 2005. ICAM-5 (telencephalin) gene expression in head and neck squamous carcinoma tumorigenesis and perineural invasion! Oral Oncol 41(6): 580-588.

27. Mashima T, Sato S, Sugimoto Y, Tsuruo T, Seimiya H. 2009. Promotion of glioma cell survival by acyl-CoA synthetase 5 under extracellular acidosis conditions. Oncogene 28(1): 9-19.

28. Mokarram P, Kumar K, Brim H, Naghibalhossaini F, Saberi-Firoozi M, Nouraie M, Green R, Lee E, Smoot D T, Ashktorab H. 2009. Distinct high-profile methylated genes in colorectal cancer. PLoS One 4(9): e7012.

29. Nabilsi N H, Broaddus R R, Loose D S. 2009. DNA methylation inhibits p53-mediated survivin repression. Oncogene 28(19): 2046-2050.

30. Nagel S, Meyer C, Quentmeier H, Kaufmann M, Drexler H G, MacLeod R A. 2008. MEF2C is activated by multiple mechanisms in a subset of T-acute lymphoblastic leukemia cell lines. Leukemia 22(3): 600-607.

31. Pardo C, Hoose S A, Pondugula S, Kladde M P. 2009. DNA methyltransferase probing of chromatin structure within populations and on single molecules. Methods Mol Biol 523: 41-65.

32. Pardo C E, Can I M, Hoffman C J, Darst R P, Markham A F, Bonthron D T, Kladde M P. 2011. Methylviewer: computational analysis and editing for bisulfite sequencing and DNA methyltransferase accessibility protocol for individual templates (MAPit) projects. Nucleic Acids Res 39(1): e5.

33. Pardo C E, Darst R P, Nabilsi N H, Delmas A L, Kladde M P. 2011. Simultaneous single-molecule mapping of protein-DNA interactions and DNA methylation by MAPit. Curr Protoc Mol Biol Chapter 21: Unit 21 22.

34. Piao J H, Odeberg J, Samuelsson E B, Kjaeldgaard A, Falci S, Seiger A, Sundstrom E, Akesson E. 2006. Cellular composition of long-term human spinal cord- and forebrain-derived neurosphere cultures. J Neurosci Res 84(3): 471-482.

35. Pujadas E and Feinberg A P. 2012. Regulated noise in the epigenetic landscape of development and disease. Cell 148(6): 1123-1131.

36. Renaud S, Loukinov D, Abdullaev Z, Guilleret I, Bosman F T, Lobanenkov V, Benhattar J. 2007. Dual role of DNA methylation inside and outside of CTCF-binding regions in the transcriptional regulation of the telomerase hTERT gene. Nucleic Acids Res 35(4): 1245-1256.

37. Renbaum P, Abrahamove D, Fainsod A, Wilson G G, Rottem S, Razin A. 1990. Cloning, characterization, and expression in *Escherichia coli* of the gene coding for the CpG DNA methylase from *Spiroplasma* sp. strain MQ1 (M.SssI). Nucleic Acids Res 18: 1145-1152.

38. Santosh V, Arivazhagan A, Sreekanthreddy P, Srinivasan H, Thota B, Srividya M R, Vrinda M, Sridevi S, Shailaja B C, Samuel C, et al. 2010. Grade-specific expression of insulin-like growth factor-binding proteins-2, -3, and -5 in astrocytomas: IGFBP-3 emerges as a strong predictor of survival in patients with newly diagnosed glioblastoma. Cancer Epidemiol Biomarkers Prev 19(6): 1399-1408.

39. Schreiber S L and Bernstein B E. 2002. Signaling network model of chromatin. Cell 111(6): 771-778.

40. Sharma S V, Lee D Y, Li B, Quinlan M P, Takahashi F, Maheswaran S, McDermott U, Azizian N, Zou L, Fischbach M A, et al. 2010. A chromatin-mediated reversible drug-tolerant state in cancer cell subpopulations. Cell 141(1): 69-80.

41. Shen L, Dean N M, Glazer R I. 1999. Induction of p53-dependent, insulin-like growth factor-binding protein-3-mediated apoptosis in glioblastoma multiforme cells by a protein kinase Cα antisense oligonucleotide. Mol Pharmacol 55(2): 396-402.

42. Shen L and Glazer R I. 1998. Induction of apoptosis in glioblastoma cells by inhibition of protein kinase c and its association with the rapid accumulation of p53 and induction of the insulin-like growth factor-1-binding protein-3. Biochem Pharmacol 55(10): 1711-1719.

43. Shmelkov S V, Jun L, St Clair R, McGarrigle D, Derderian C A, Usenko J K, Costa C, Zhang F, Guo X, Rafii S. 2004. Alternative promoters regulate transcription of the gene that encodes stem cell surface protein AC133. Blood 103(6): 2055-2061.

44. Siebzehnrubl F A, Vedam-Mai V, Azari H, Reynolds B A and Deleyrolle L P. 2011. Isolation and characterization of adult neural stem cells. Methods Mol Biol 750: 61-77.

45. Song C X, Yi C, He C. 2012. Mapping recently identified nucleotide variants in the genome and transcriptome. Nat Biotechnol 30(11): 1107-1116.

46. Stark A M, Doukas A, Hugo H H, Mehdorn H M. 2010. The expression of mismatch repair proteins MLH1, MSH2 and MSH6 correlates with the Ki67 proliferation index and survival in patients with recurrent glioblastoma. Neurol Res 32(8): 816-820.

47. Sumiyoshi H, Inoguchi K, Khaleduzzaman M, Ninomiya Y, Yoshioka H. 1997. Ubiquitous expression of the α1(XIX) collagen gene (Col19a1) during mouse embryogenesis becomes restricted to a few tissues in the adult organism. J Biol Chem 272(27): 17104-17111.

48. Sun Y, Kong W, Falk A, Hu J, Zhou L, Pollard S, Smith A. 2009. CD133 (prominin) negative human neural stem cells are clonogenic and tripotent. PLoS One 4(5): e5498.
49. Suriano A R, Sanford A N, Kim N, Oh M, Kennedy S, Henderson M J, Dietzmann K, Sullivan K E 2005. GCF2/LRRFIP1 represses tumor necrosis factor alpha expression. Mol Cell Biol 25(20): 9073-9081.
50. Swinton D, Hattman S, Crain P F, Cheng C S, Smith D L and McCloskey J A. 1983. Purification and characterization of the unusual deoxynucleoside, α-N-(9-β-D-2'-deoxyribofuranosylpurin-6-yl)glycinamide, specified by the phage Mu modification function. Proc. Natl. Acad. Sci. USA 80(24), 7400-7404.
51. Szybka M, Bartkowiak J, Zakrzewski K, Polis L, Liberski P, Kordek R. 2003. Microsatellite instability and expression of DNA mismatch repair genes in malignant astrocytic tumors from adult and pediatric patients. Clin Neuropathol 22(4): 180-186.
52. Tavassoli P, Wafa L A, Cheng H, Zoubeidi A, Fazli L, Gleave M, Snoek R, Rennie P S. 2010. TAF1 differentially enhances androgen receptor transcriptional activity via its n-terminal kinase and ubiquitin-activating and -conjugating domains. Mol Endocrinol 24(4): 696-708.
53. Varley K E, Mitra R D. 2010. Bisulfite patch PCR enables multiplexed sequencing of promoter methylation across cancer samples. Genome Res 20(9): 1279-1287.
54. Wolff E M, Byun H M, Han H F, Sharma S, Nichols P W, Siegmund K D, Yang A S, Jones P A, Liang G. 2010. Hypomethylation of a LINE-1 promoter activates an alternate transcript of the met oncogene in bladders with cancer. PLoS Genet 6(4): e1000917.
55. Xu M, Kladde M P, Van Etten J L, Simpson R T. 1998. Cloning, characterization and expression of the gene coding for a cytosine-5-DNA methyltransferase recognizing GpC. Nucleic Acids Res 26(17): 3961-3966.
56. Yang X, Noushmehr H, Han H, Andreu-Vieyra C, Liang G, Jones P A. 2012. Gene reactivation by 5-aza-2'-deoxycytidine-induced demethylation requires SRCAP-mediated H2A.Z insertion to establish nucleosome depleted regions. PLoS Genet 8(3): e1002604.
57. You J S, Kelly T K, De Carvalho D D, Taberlay P C, Liang G, Jones PA. 2011, Oct. 4 establishes and maintains nucleosome-depleted regions that provide additional layers of epigenetic regulation of its target genes. Proc Natl Acad Sci USA 108(35): 14497-14502.
58. Yu J, Bulk E, Ji P, Hascher A, Tang M, Metzger R, Marra A, Serve H, Berdel W E, Wiewroth R, et al. 2010. The EPHB6 receptor tyrosine kinase is a metastasis suppressor that is frequently silenced by promoter DNA hypermethylation in non-small cell lung cancer. Clin Cancer Res 16(8): 2275-2283.

We claim:

1. A method of simultaneously determining the methylation state and chromatin structure of target loci, the method comprising:
   a) treating a sample of genetic material with at least one DNA methyltransferase to to methylate accessible chromatin GC sites;
   b) digesting the DNA methyltransferase-treated genetic material with a composition comprising at least one enzyme insensitive to DNA methylation at both CG and GC sites to produce digested genetic material comprising DNA strands harboring at least one target locus, wherein the at least one enzyme comprises AluBI or MseI;
   c) ligating a U-1 oligonucleotide to a 5' end and a U-2 oligonucleotide to a 3' end of a denatured DNA strand harboring at least one target locus to form a U-1- and U-2-containing DNA strand;
   d) treating the U-1- and U-2-containing DNA strands with bisulfite to produce bisulfite-treated DNA strands;
   e) amplifying the bisulfite-treated DNA strands using polymerase chain reaction (PCR) with a U-1 primer and a U-2 primer to produce one or more PCR products;
   f) sequencing the one or more PCR products, and
   g) analyzing the sequences to determine the methylation state and the chromatin structure of the target loci.

2. The method of claim 1, wherein ligating comprises contacting the DNA strand harboring the at least one target locus in conditions that allow hybridization of complementary DNA with a set of oligonucleotide molecules, wherein the set of oligonucleotide molecules comprises:
   1) an upstream patch oligonucleotide or plurality of upstream patches (patch-1) each having a DNA sequence, from 3' to 5' end, comprising: a sequence that hybridizes with the U-1 oligonucleotide and a sequence that hybridizes with a region at the 5' end of one of the target loci, and 2) a downstream patch oligonucleotide or plurality of downstream patches (patch-2) each having a DNA sequence, from 5' to 3' end, comprising: a sequence that hybridizes with the U-2 oligonucleotide and a sequence that hybridizes with a region at the 3' end of one of the target loci.

3. The method of claim 2, wherein the contacting step occurs in the presence of the U-1 oligonucleotide, the patch-1, the U-2 oligonucleotide, the patch-2, and DNA ligase.

4. The method of claim 1, further comprising: (i) purifying the DNA methyltransferase-treated genetic material prior to the digesting step; (ii) purifying the digested material comprising DNA strands harboring target loci prior to the ligating step; or (iii) subjecting the U-1- and U-2-containing DNA strands to at least one DNA exonuclease, or purifying the U-1- and U-2-containing DNA strands, or both, prior to the treating step; or a combination of two or more of (i), (ii), and (iii).

5. The method of claim 1, wherein:
   1) the U-1 primer further comprises: (i) a sample-specific barcode; or (ii) a first adapter sequence specific for a sequencing platform; or a combination of (i) and (ii); and
   2) the U-2 primer further comprises: (i) a sample-specific barcode; or (ii) a second adapter sequence specific for the sequencing platform; or a combination of (i) and (ii).

6. The method of claim 1, wherein the at least one DNA methyltransferase enzyme methylates cytosine at position C5.

7. The method of claim 1, wherein the U-1 oligonucleotide has one or more modifications at its 5' and/or 3' end that render the U1 oligonucleotide resistant to exonucleases.

8. The method of claim 7, wherein the modification comprises adding up to 10 phosphorothioate modifications to the 5' and/or 3' end of the U-1 oligonucleotide.

9. The method of claim 1, wherein the U-2 oligonucleotide has one or more modifications at its 3' and/or 5' end that render the U2 oligonucleotide resistant to exonucleases.

10. The method of claim 9, wherein the modification comprises adding a phosphate to the 5' end and a carbon spacer to the 3' end and/or up to 10 phosphorothioate modifications to the 3' and/or 5' end of the U-2 oligonucleotide.

11. The method of claim 1, wherein the sequencing step implements a multiplex sequencing platform.

12. A method of determining the differences in the chromatin structure and methylation state of target loci between a first group of cells and a second group of cells, the method comprising:
   a) determining the methylation state and chromatin structure of the target loci in the first group of cells by treating the first group of cells according to the method of claim 1,
   b) determining the methylation state and chromatin structure of the target loci in the second group of cells by treating the second group of cells according to the method of claim 1, and
   c) comparing the methylation state and chromatin structure obtained in steps a and b to determine the differences in the chromatin structure and methylation state of the target loci between the first group of cells and the second group of cells.

13. A method of identifying genes associated with a condition, the method comprising:
   a) determining the methylation state and chromatin structure of promoters and/or other loci of a set of sequences in normal cells by treating the normal cells according to the method of claim 1,
   b) determining the methylation state and chromatin structure of the promoters and/or other loci of the set of sequences in cells suffering from the condition by treating the cells suffering from the condition according to the method of claim 1, and
   c) comparing the methylation state and chromatin structure of promoters and/or other loci of the genes in the normal cells and the cells suffering from the condition to identify genes associated with the condition.

14. The method of claim 13, wherein the condition is cancer.

15. A method of identifying cells suffering from a disease in a group of cells by determining the methylation state and chromatin structure of target loci known to be associated with the disease by treating the group of cells according to the method of claim 1 and identifying cells as suffering from the disease by comparing the methylation state and chromatin structure of the target loci known to be associated with the disease with the methylation state and chromatin structure of the target loci in normal cells.

16. The method of claim 15, wherein the disease is cancer.

* * * * *